(12) United States Patent
Palmenberg et al.

(10) Patent No.: US 7,947,493 B2
(45) Date of Patent: May 24, 2011

(54) COMPOSITIONS AND METHODS FOR REGULATING MRNA TRANSCRIPTION AND TRANSLATION

(75) Inventors: Ann C. Palmenberg, Madison, WI (US); Aleksey G. Aminev, Fitchburg, WI (US); Rachel P. Groppo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 716 days.

(21) Appl. No.: 10/888,143

(22) Filed: Jul. 9, 2004

(65) Prior Publication Data

US 2005/0019808 A1    Jan. 27, 2005

Related U.S. Application Data

(60) Provisional application No. 60/485,681, filed on Jul. 9, 2003.

(51) Int. Cl.
C12N 15/00 (2006.01)
C12N 15/10 (2006.01)
C12N 15/11 (2006.01)
C12N 15/34 (2006.01)

(52) U.S. Cl. .................. 435/320.1; 435/69.1; 435/91.4; 536/23.1; 536/23.7; 536/24.1

(58) Field of Classification Search .................. None
See application file for complete search history.

(56) References Cited

U.S. PATENT DOCUMENTS 6,440,718 B1 * 8/2002 Probst ......................... 435/235.1

OTHER PUBLICATIONS

Lee and Pack, Utilization of *Escherichia coli* Tac Promoter in *Bacillus subtilis*, Biotechnology Letters vol. 12 No. 12 925-930 (1990).*
Roos et al, Polyprotein Processing of Theiler's Murine Encephalomyelitis Virus; Journal of Virology, Dec. 1989, vol. 63, (12) p. 5344-5353.*
Pevear et al, Analysis of the Complete Nucleotide Sequence of the Picornavirus Theiler's Murine Encephalomyeltitis Virus Indicates That it is closely related to Cardioviruses, J Virology, 1987, vol. 61 (5), pp. 1507-1516.*
Yarovoi et al, Human cell lines expressing hormone regulated T7 RNA polymerase localized at distinct intranuclear sites, Gene 275 (2001) 73-81.*

Aminev, A.G., "Cardiovirus 2A protein induces the synthesis of modified . . . ," Meeting talk and poster for Am Society for Virology Annual Meeting Jul. 21, 2001, Madison, WI.
Aminev, A.G., "Cardiovirus 2, 3CD and 3BCD localize to nuclei and induce . . . ," Meeting talk and poster for Europic Picornavirus Meeting May 17, 2002, Cape Cod, MA.
Aminev, A.G., "Cardiovirus and Rhinovirus 2A, 3CD and 3BCD localize to nuclei . . . ," Meeting poster for XIIth International Congress of Virology, Jul. 27, 2002, Paris, France.
Aminev, A.G., et al., "Encephalomyocarditis viral protein 2A localizes to nucleoli and inhibits cap-dependent mRNA translation," Virus Research (2003) 95:45-57.
Aminev, A.G., et al., "Encephalomyocarditis viral (EMCV) proteins 2A and 3BCD localize to nucleoli and inhibit cellular mRNA . . . ," Virus Research (2003) 95:59-73.
Binder, J.J., et al., "Genetic stability of attenuated mengovirus vectors with duplicate primary cleavage sequences," (2003) Virology 312:481-494.
Duque, H., et al., "Phenotypic characterization of three phylogenetically conserved stem-loop motifs in the mengovirus 3' untranslated region," J. Virol. (2001) 75:3111-3120.
Hahn, H., et al., "Deletion mapping of the encephalomyocarditis virus primary cleavage site," J. Virol. (2001) 75:7215-7218.
Hall, D.J., et al., "Cleavage site mutations in the encephalomyocarditis virus P3 region lethally abrogate the normal processing cascade," J. Virol. (1996a) 70:5954-5961.
Hall, D.J., et al., "Mengo virus 3C proteinase: Recombinant expression, intergenus substrate cleavage and localization in vivo," Virus Genes (1996) 13:99-110.
IRES Bicistronic Expression Vectors, for the rapid and efficient production of stable mammalian cell lines, CLONTECHniques Oct. 1996 Abstract.
Palmenberg, A.C., et al., "Alignments and comparative profiles of picornavirus genera," Molecular Biology of Picornaviruses (Semler and Wimmer Eds.) (2001) 149-158.
Palmenberg, A.C., "Cardiovirus 2A localizes to nucleoli, upregulates rRNA . . . ," Meeting talk and poster for S. Europic Picornavirus meeting May 17, 2002, Cape Cod, MA.
Svitkin, Y.V., et al., "Rapamycin and wortmannin enhance replication of a defective encephalomyocarditis virus," J. Virol. (1998) 72:5811-5819.

* cited by examiner

*Primary Examiner* — Maria Marvich
(74) *Attorney, Agent, or Firm* — Quarles & Brady LLP; Sara D. Vinarov

(57) ABSTRACT

The invention relates to compositions, specifically novel nucleic acid constructs encoding a cardiovirus 2A polypeptide operably linked to suitable promoters. Also, disclosed are methods whereby the nucleic acid constructs are introduced into cells or cell free systems to regulate cellular mRNA transcription and cap-dependent or internal ribosomal entry site (IRES)-dependent mRNA translation.

6 Claims, 16 Drawing Sheets

FIG 13

COMPOSITIONS AND METHODS FOR REGULATING MRNA TRANSCRIPTION AND TRANSLATION

CROSS-REFERENCE TO RELATED APPLICATIONS

This application claims the priority benefit of U.S. Provisional Application Ser. No. 60/485,681, filed Jul. 9, 2003, incorporated by reference herein.

STATEMENT REGARDING FEDERALLY SPONSORED RESEARCH OR DEVELOPMENT

This invention was made with government support under grant AI-17331 awarded by the National Institutes of Health. The United States Government has certain rights in this invention.

BACKGROUND OF THE INVENTION

The picornavirus family, which includes encephalomyocarditis viruses (EMCV) have a genome which is composed of a single-stranded, positive sense RNA of about 7,500 to 8,300 nucleotides (Belsham et al., 1996). Picornavirus RNA is functionally monocistronic and, upon infection, is translated into a single polyprotein that is processed to yield structural and nonstructural virus proteins (Rueckert, R. R., 1996).

Picornaviral proteins and their precursors take their names (L, P1, P2, P3) from their sequential locations within the polyprotein. The leader or "L" proteins are present only in cardio- and aphthoviruses. The EMCV and Mengovirus leaders are about 7 kD in molecular weight. The four P1 peptides are the capsid proteins, 1A, 1B, 1C and 1D (EMCV: 8, 28, 25, and 30 kD). Those fragments derived from a common precursor stay together as a protomer unit throughout particle morphogenesis (Arnold et al., 1987; Grigera et al., 1985; Palmenberg, 1982). The middle portion of the polyprotein contains peptides 2A, 2B and 2C (EMCV: 16, 17, and 36 kD). Protein 2C is an ATPase (Pfister et al., 2000). In the entero- and rhinoviruses, 2C is also the genetic locus of the guanidine resistance marker, a compound that affects the initiation of RNA synthesis (Anderson-Sillman et al., 1984; Pincus et al., 1986).

However, the 2C protein is not a polymerase, and its contribution to the replication cycle remains unclear. The P3 peptides, 3A, $3B^{VPg}$, $3C^{pro}$, and $3D^{pol}$ (EMCV: 10, 2, 22, and 51 kD) are more closely associated with genome replication. Preparations of $3D^{pol}$ can catalyze the elongation of nascent RNA chains in primer-dependent reactions, an activity that identifies this enzyme as a central element of viral polymerase complexes (Flanegan and Baltimore, 1977). Protein 3B is VPg, the peptide covalently linked to the 5' end of the genome (Pallansch et al., 1980). VPg sequences are rich in basic, hydrophilic amino acids and have only one tyrosine residue (the attachment site) at position 3 from the amino end of the peptide. Initiation of positive- and negative-strand RNA synthesis requires VPg, perhaps as free protein or as part of a larger donor peptide (Morrow et al., 1984). Protease $3C^{pro}$ is the central enzyme in the viral cleavage cascade. After a co-translational primary break, catalyzed by a peptide cassette near the COOH-end of 2A (Hahn and Palmenberg, 2001), nearly all subsequent, or secondary cleavages within cardiovirus polyproteins, are affected by $3C^{pro}$ (Palmenberg, 1989).

Furthermore, infection with most picornaviruses is characterized by a strong inhibition of host cell protein synthesis at a time when virus-species proteins are efficiently produced (Ehrenfeld, E., 1996). Enteroviruses and rhinoviruses inhibit host translation, at least partially, by inactivation of eukaryotic translation initiation factor 4F (eIF4F), which binds to the cap structure of cellular mRNAs. eIF4F is composed of three polypeptides: eIF4E, eIF4A, and eIF4G. eIF4E is the cap-binding subunit (Sonenberg, N., 1996). Picornavirus RNAs are naturally uncapped and translate by a cap- and eIF4E-independent mechanism, by which the ribosomes bind to an (IRES internal ribosome entry site) (Agol, V. I., 1991).

Enteroviruses and rhinoviruses disrupt eIF4F through cleavage of the eIF4G subunit by 2Apro. This cleavage has been reported to be direct (Haghighat, et al., 1996) or indirect (Wyckoff et al., 1992). eIF4G cleavage does not preclude but, rather, stimulates cap-independent initiation of viral protein synthesis, since the cap-binding subunit, eIF4E, remains associated with the N-terminal cleavage product (Borman et al., 1997). The C-terminal cleavage fragment of eIF4G interacts with eIF4A and eIF3 to support IRES-dependent, but not cap-dependent, translation initiation (Borman et al., 1997).

In strong contrast to enteroviruses and rhinoviruses, it is widely known that no cleavage of eIF4G occurs following infection of cells with cardioviruses. Encephalomyocarditis virus, "EMCV" (NBCI Accession No. M81861), Mengovirus (NBCI Accession No. L22089), or Theilovirus (NBCI Accession Nos. M16020, M20562, and M20301) are examples of cardioviruses. It has been learned that these viruses have relatively efficient translation of their coding RNA in cell free systems. It has also been learned that there are various techniques for culturing and producing the natural cardioviruses.

Also, it is widely known that the 2A protein of EMCV is not similar to the enterovirus and rhinovirus 2Apro and does not possess protease consensus motifs or detectable proteolytic activity (Lloyd et al., 1988). Therefore, it is believed that cardiovirus infection does not induce eIF4G cleavage, and the encoded L and 2A proteins are not proteases. Furthermore, the genome sequences from EMCV, Mengo and the Theiler's viruses, which are known to encode 2A proteins (about 150 amino acids) do not share recognizable sequence similarity with any other viral or host proteins, including the 2As from other picornavirus species.

It has long been assumed that the shutoff of host cell protein synthesis after EMCV infection results from the ability of viral RNA to efficiently compete with capped cellular mRNAs for some limiting component of the translational machinery (Lawrence et al., 1974). Recently, it was suggested that EMCV causes the shutoff of host translation by dephosphorylation and activation of a suppressor of cap-dependent translation, 4E-BP1 (eIF4E-binding protein 1) (Gingras et al., 1996). However, to date no definitive mechanism has been established with respect to how EMCV causes the shutoff of host translation. Accordingly, it would be desirable to identify viral proteins involved in mRNA transcription and translation so as to enable the design of nucleic acid constructs which can be used to inhibit virally infected cells.

BRIEF SUMMARY OF THE INVENTION

The invention describes the construction and the use of nucleic acid constructs assembled from genomes of viruses in the genus Cardiovirus. The compositions and methods of the invention are largely based upon the discovery that cardiovirus protein 2A, when expressed in mammalian cells, by any of a variety of genetically engineered methods, and in the absence of any other viral proteins or genes, will localize to the nucleoli of cells, bind to ribosomes, and consequently bring about a reduction in cap-dependent translation, but not IRES-dependent translation in these cells. Therefore, in accordance with this novel finding, two important observations were made: 1) the ability of protein 2A to inhibit cap-dependent mRNA translation; and 2) the ability of protein 2A in combination with 3BCD to inhibit cellular mRNA transcription, but not rRNA transcription.

Accordingly, in a broad sense the present invention provides novel compositions in the form of nucleic acid constructs, wherein the constructs have either a polynucleotide sequence encoding a 2A cardiovirus polypeptide operably linked to at least one DNA-dependent RNA polymerase promoter or to at least one IRES sequence. These constructs can be used to inhibit cellular mRNA transcription and cap-dependent translation.

More specifically, in one aspect, the present invention provides for nucleic acid constructs having a 2A sequence in the presence of at least one IRES-driven gene, wherein the gene could be any polynucleotide encoding a protein. The construct(s) may be introduced into the eukaryotic cells as a single tricistronic cDNA; as two or more mono-cistronic cDNAs or as 2A-fusion genes. The construct(s) may also be used in combination, rather than as single cDNAs; or as RNA; and as mixed combinations of DNA and RNA.

In another aspect, the present invention provides for nucleic acid constructs having a 2A sequence introduced as a toxic translational or transcriptional element in cells or cell-free systems. The construct(s) may be introduced into the eukaryotic cells as DNA, RNA or as a polypeptide.

In another aspect, the present invention provides for nucleic acid constructs having a cardiovirus 2A sequence introduced into the eukaryotic cells as a mutant 2A sequence resulting in altered cellular regulatory activities. The construct(s) may be introduced into the eukaryotic cells as having mutations in the 2A nuclear localization signal (NLS) sequence or at the carboxyl terminal 2A primary cleavage sequence.

In another aspect, the present invention provides for nucleic acid constructs having a cardiovirus 2A sequence is introduced into the eukaryotic cells in combination of other cardiovirus genes (e.g., L, 1A, 2C, 3A, 3B, 3C, and 3D) such that the 2A sequence is expressed from non-replicating cDNA or RNA; or the 2A sequence is expressed from self-replicating cDNA or RNA.

In another aspect, the invention provides methods for down-regulating or inhibiting mRNA transcription and/or cap-dependent translation by inhibiting pol-II activity through introducing suitable 2A construct(s) described herein into cells or cell-free systems.

In another aspect, the invention provides methods for inhibiting mRNA transcription in a virally-infected cell by introducing into a cell at least one nucleic acid construct having a combination of a cardiovirus 3BCD and a 2A sequence.

In yet another aspect, the invention provides kits comprising at least one nucleic acid construct comprising a cardiovirus polynucleotide sequence encoding a 2A polypeptide.

Also, a reporter gene may be positioned downstream of the 2A sequence, the IRES sequence, or both in any of the nucleic acid constructs described herein.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE SEVERAL VIEWS OF THE DRAWINGS

FIG. 13 shows a spectrum of nuclear labeling by P3-region precursors. Point mutations were engineered into $pEC_4$ plasmids, abrogating the encoded $3C^{pro}$ cleavage sites in the P2 and P3 regions of the genome. RNA transcripts from each construction, and from the parental sequence ($pEC_4$) were transfected into HeLa cells, and at 6 hrs (PT), the samples were fixed, stained with mAb-3D, and visualized by confocal microscopy as described in Methods.

Figure 1:
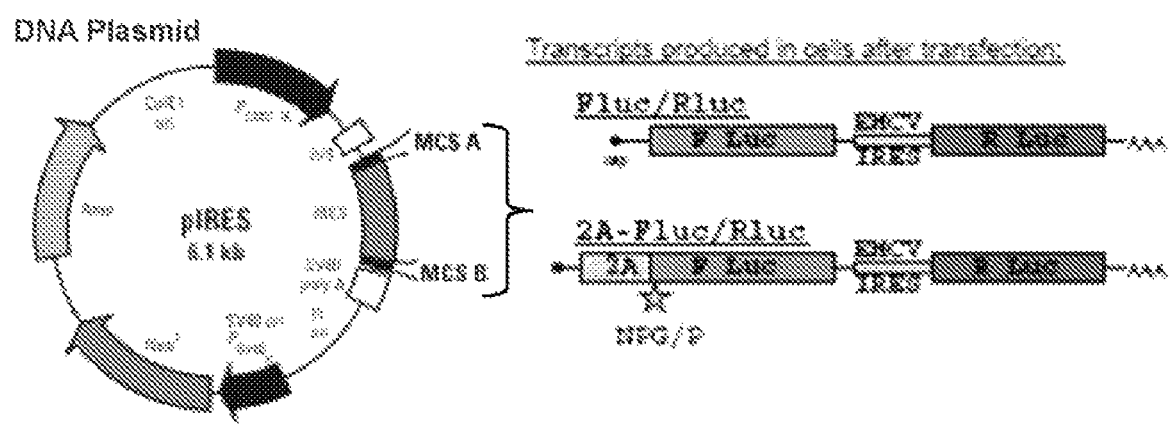
FIG. 1 is a diagram representing bicistronic luciferase vectors. Fluc/Rluc and 2A-Fluc/Rluc plasmids were created by cloning the wild-type EMCV IRES into he pIRES vector (Clontech). The IRES element is located upstream of multiple cloning site B (MCS B) and after a spacer element following multiple cloning site A (MCS A). The Renilla luciferase (Rluc) open reading frame (Promega) was then cloned into MCS B such that the first amino cid of Rluc coincides with the initiating methionine of the EMCV ORF. Either firefly luciferase (Fluc) or 2A-Fluc (from the plasmid pME-NPGP-luCM) was then cloned into the MCS A. Transcripts made from the above constructs contain a 5' cap which directs translation of the first ORF. The second ORF is translated as a result of the IRES located upstream. The 2A-Fluc/Rluc construct encodes a functional primary cleavage cassette in between the 2A and Fluc proteins, thereby resulting in two separate proteins from a single ORF.

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In accordance with the invention, Applicants have described and enabled the construction and use of a variety of different nucleic acid constructs hereinbelow. The various embodiments are categorized into the following four general types of nucleic acid constructs. In this first series of constructs the 2A sequence is provided in the presence of an IRES-driven gene. The construct(s) may be introduced into the eukaryotic cells as a single tricistronic cDNA; as two or more mono-cistronic cDNAs or 2A-fusion genes, to be used in combination, rather than as single cDNAs; or as RNA; and as mixed combinations of DNA and RNA. In the second series of constructs the 2A sequence is introduced as a toxic translational or transcriptional element in cells or cell-free systems. Applicants note that those skilled in the art of cell-free protein expression are well aware of the various cell-free systems available for use in expressing the 2A constructs of the invention. Suitable cell-free systems encompassed within the scope of this invention include wheat germ, xenopus, rabbit reticulocyte, and S-30.

The construct(s) may be introduced into the eukaryotic cells as DNA, RNA or as protein. In the third series of constructs the 2A sequence is introduced into the eukaryotic cells as a mutant 2A sequence resulting in altered cellular regulatory activities. The construct(s) may be introduced into the eukaryotic cells as having mutations in the 2A nuclear localization signal (NLS) sequence or at the carboxyl terminal 2A primary cleavage sequence. In the fourth series of constructs the 2A sequence is introduced into the eukaryotic cells in combination of other cardiovirus genes, such that the 2A sequence is expressed from non-replicating cDNA or RNA; or the 2A sequence is expressed from self-replicating cDNA or RNA.

Applicants note that so far no definitive mechanism has been established for how 2A alone and in combination with 3BCD function. However, it is believed that during cardiovirus infection, the 2A protein is found to be associated with ribosomes as part of a unique host-translational shut-off mechanism that probably involves the synthesis or modification of "toxic" ribosomes. Moreover, it is believed that 2A expression within cells can bring about a 10-20 fold reduction of host mRNA transcription as well, by a mechanism that may involve inhibition of the cellular DNA Polymerase II enzyme. The DNA Polymerase II, however, does not shut off translation directed by mRNAs containing internal ribosomal entry sites (IRESs), such as that encoded by the parental virus, EMCV. Furthermore, it is believed that the 2A protein does not appear to shut off cellular transcription by DNA polymerase I or III enzymes that lead to the synthesis of new ribosomes and tRNA. Furthermore, it is believed that when the 2A protein is introduced into cells, IRES-dependent translation is significantly enhanced because it appears that the host cannot manufacture competing mRNAs, and of those host mRNAs in the cell, the ribosome preference is directed towards IRES-containing mRNAs. Accordingly, it appears that the 2A protein is capable of acting as an IRES enhancer protein that can down-regulate host cap-dependent protein translation and boost IRES-dependent translation.

The following examples are provided as further non-limiting illustrations of particular embodiments of the invention.

Figure 4:
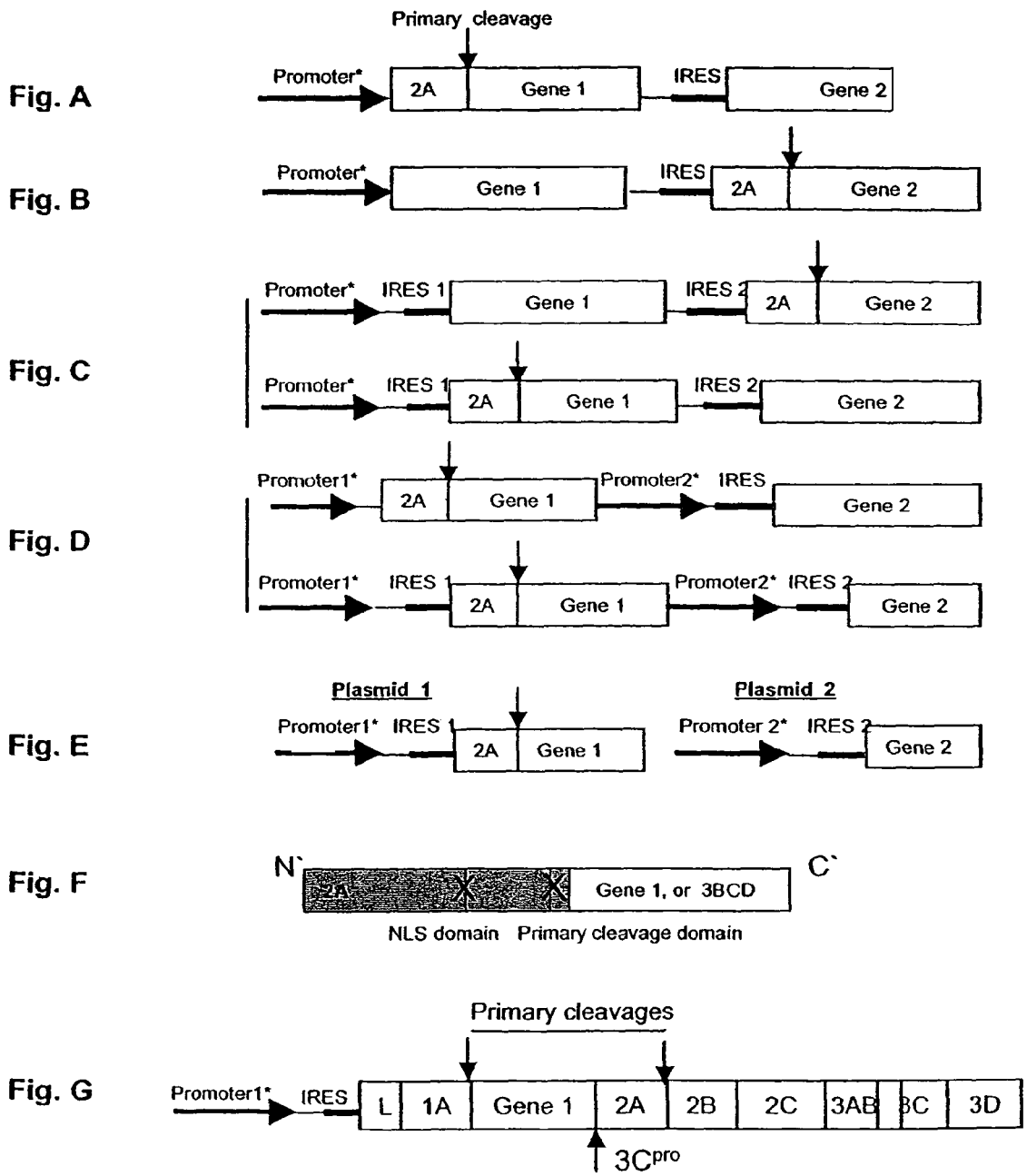
FIGS. 4A-G represent various monocistronic, bicistronic, and tricistronic 2A sequence cDNA constructions (i.e., 2A fusion genes). "Gene1" and "Gene2" denote any reporter gene or other desired gene of interest to be expressed. "2A" denotes the cardiovirus sequence encoding protein 2A, along with its COOH terminal autocatalytic primary cleavage motif. "Promoter" designates any DNA-dependent RNA polymerase promoter that will produce mRNA transcripts from the cDNA. This includes pol-I, pol-II, or pol-III variants which may express in a constitutive (e.g., $CMV_{1E}$) or inducible manner (e.g., $CMV_{min}$).

In the first embodiment, the 2A sequence is provided in the presence of an IRES-driven gene. In this embodiment, the construct(s) may be introduced into eukaryotic cells from a single DNA. For example, FIG. 4A shows transfection or transformation of eukaryotic cells (e.g., HeLa, COS, 3T3, or any suitable commercial eukaryotic expression system) with a single tricistronic cDNA (or plasmid) that begins with a pol-2 promoter sequence (e.g., CMV, SV40), followed by a 2A sequence, fused in-frame to a reporter gene (gene1), followed by an EMCV IRES-driven second reporter gene, or gene of interest (gene2). Upon transcription in the nucleus from the (constitutive or inducible) promoter sequence, the capped mRNA will function defacto in a bicistronic manner, allowing cap-dependent translation of 2A-gene1, and cap-independent translation of gene2. The 2A protein will release from the fusion, co-translationally and work to down-regulate subsequent mRNA transcription, and translation of all cap-dependent mRNAs in the cell (including host mRNAs, and 2A-gene1). The IRES-dependent translation of gene 2 will proceed unabated, and in the absence of competition from other cellular mRNAs.

By "reporter gene", applicants refer to a foreign polynucleotide or cDNA that when expressed yields a polypeptide that is readily detectable, either by providing a colorimetric signal under certain environmental conditions or some other signal well known to those of ordinary skill in the art, as described below.

Furthermore for example, FIG. 4B is essentially the same as FIG. 4A except the 2A polypeptide is expressed as a self-cleaving entity from a 2A-gene2-fusion construction. In this embodiment, the cap-dependent expression of gene1 could be used as an indication of transformation efficiency (e.g., a GFP gene or luciferase gene), while gene2 produces the desired recombinant protein.

This embodiment also encompasses a construct where the IRES element that is driving the expression of gene2 (or 2A-gene2), could be derived from any other cap-independent protein expression system, such as another type-II IRES, a type-I IRES, the IRES from hepatitis C, or another virus, or even a naturally occurring cellular IRES.

Another construct envisioned by this embodiment is where the transcriptional promoter is not pol-2 dependent (e.g., pol-I or pol-III-dependent), but still produces capped mRNAs that are exported to the cytoplasm, and translated there.

Also encompassed by this embodiment is an example where both gene1 and gene2, either one of which may be fused to 2A, are driven by two different, non-competitive IRES sequences. In this case, 2A will down regulate host mRNA synthesis, but the expression of both cDNA genes will proceed, because they are not affected by 2A.

It is encompassed within the scope of this embodiment that the construct(s) may be introduced into eukaryotic cells from multiple DNAs. For example, the constructions described in FIG. 4A, could also be introduced into cells as two or more mono-cistronic cDNAs or 2A-fusion genes, to be used in combination, rather than as a single cDNA. Alternatively, one cDNA could have multiple promoter sequences (FIG. 4D), which would likewise lead to the expression of 2 or more transcripts.

In yet another example, shown in FIG. 4E the cells could be stably transformed with a cDNA encoding an inducible pol-II promoter (e.g., CMV), followed by a 2A gene, or 2A gene, fused to a reporter. As long as these cells are not induced and 2A is not expressed, the cells will grow normally. After transfection with a second cDNA encoding a constitutive pol-I promoter linked to a an EMCV IRES-driven gene2, and induction of the first cDNA, the expressed 2A protein would then down regulate cap-dependent translation, yet still allow substantial protein expression of the IRES-driven gene2.

In this embodiment, the construct(s) may also be introduced into eukaryotic cells from RNA. Nearly all constructions in 1A and 1B above could also be introduced into cells by transfection with RNA instead of transformation with DNA. The advantage of an RNA method would be the elimination of a cellular transcriptional promoter sequences from any of the constructs, and in some embodiments, a consequent lack of capping requirements on the introduced RNAs.

Also, within the scope of the invention is that cells could be transfected with a tricistronic mRNA synthesized in vitro using T7 polymerase and a cap analogue. The RNA could be of the form: cap, 2A-gene1 fusion, EMCV IRES, gene 2. Alternatively, as in FIG. 4B above, the 2A gene could be expressed as a self-cleaving fusion with gene2.

In yet another aspect of this embodiment it is encompassed that the cells could be transfected with multiple mRNAs, each encoding a different IRES-driven gene. At least one of these RNAs must encode 2A, as an IRES-driven or cap-driven gene, or as part of a self-releasing 2A fusion protein.

Also, in this embodiment, it is encompassed that the construct(s) may also be introduced into eukaryotic cells from combinations of DNA and RNA. Applicants note that all constructions described in FIGS. 4A-C above, involving multiple cDNAs or RNAs, and could be introduced in mixed combinations.

In this embodiment, it is envisioned that the cells could be stably transformed with a cDNA encoding an inducible pol-II promoter (e.g., CMV), followed by a 2A gene, or 2A gene fused to a reporter. Subsequent transfection with an mRNA encoding an IRES-driven gene2, followed by induction of gene1, would result in expression of 2A (via a pol-II produced capped mRNA), 2A-dependent down regulation of pol-II transcription and cap-dependent translation, yet there would be continued expression of IRES-dependent gene2. The net result would be a higher expression level of the gene2 product per cell, than if this RNA were transfected without parallel 2A expression.

In the second embodiment, it is within the scope of the invention to have the 2A sequence is introduced as a toxic translational or transcriptional element in cells or cell-free systems. For example, the 2A protein by itself, and in the absence of any other viral or cellular proteins is toxic to cells because it will induce a down regulation of pol-II dependent mRNA transcription, and an inhibition of the translation of capped (cellular) mRNA. In all above described examples (section 1), the introduction of 2A was used as an aid to enhance translation expression from IRES-driven genes that were introduced in tandem (or in timely sequence) with 2A. However, the singular introduction of 2A into cells will also target them into an apoptotic or necrotic death cycle.

In this embodiment, it is envisioned that the 2A gene can be introduced as DNA. For example, the 2A gene is introduced into any cell-targeting delivery system as a freestanding gene, or as the amino-terminal segment in a fusion protein gene, to be released autocatalytically during translation. In a preferred construction, 2A expression itself could be driven by an IRES (to increase the expression level, but this is not a requirement). Induction, mRNA transcription and translation of 2A protein would lead to 2A-induced shutoff of all cellular translation and pol-II transcription, leading eventually to cell death in any cell that expressed 2A. Specific targeting (e.g.,) of tumor cells, by delivery of 2A-encoding cDNAs would result in their necrotic death.

Also, it is envisioned that the cells may be stably transformed with a plasmid cDNA encoding an IRES-2A gene sequence (or just the 2A gene), under the control of an inducible promoter sequence (e.g., CMV). Cells could be propagated or amplified in the absence of 2A induction, but after induction, all cells carrying this gene would undergo 2A-mediated apoptotic or necrotic death within (about) 24 hrs).

Another example of this embodiment is that a 2A gene may be introduced simply as RNA. Here the 2A gene transcripts (capped or driven by any IRES segment) would be introduced into cells by transfection, or by any RNA gene-vector delivery system. Expression of 2A would result in targeted cell death.

Also, encompassed within this embodiment is that 2A may be introduced to a cell as a protein: For examine from eukaryotic cells will express proteins from capped or IRES-driven mRNAs. The introduction of recombinant 2A protein into such extracts would result in the expression of proteins only from the IRES-driven mRNAs. This method could result in lower background levels of endogenous (capped) protein expression in such extracts or act as a timing switch between capped and IRES-driven protein expression.

In another example, injection or electroporation on of recombinant 2A protein into cells would be toxic for those cells and kill them.

In the third embodiment, the 2A sequence is introduced as Mutant 2A sequences having altered cellular activities. In this embodiment, the introduction (or synthesis) of 2A protein in cells has two effects: a reduction of cap-dependent translation (in the cytoplasm) and a reduction of pol-II dependent mRNA transcription within the nucleus. The inhibition of pol-II requires transport of 2A into the nucleus via a nuclear localization signal (NLS) encoded within the protein. The cytoplasmic translational inhibition activity of 2A does not require nuclear transport, or the activity of the NLS. Neither the cytoplasmic nor the nuclear activities require the endogenous, autocatalytic activities of 2A.

In this embodiment, a 2A NLS mutation is introduced into the cells, such as is shown in FIG. 4F. Recombinant mutation of the 2A NLS sequence (putative: YHKRIRPFRLP fragment, SEQ ID NO. 16) at one or more locations will result in a 2A that remains in the cytoplasm and retains its ability to inhibit cap-dependent translation, but such mutations will not allow translocation of the protein to the nucleus, or inhibition of pol-II transcription.

Furthermore, it is encompassed within the scope of the invention that the mutation may be located in the 2A primary cleavage sequence, such as is shown in FIG. 4F. For example, recombinant mutation of the carboxyl terminal 2A segment responsible for co-translational, autocatalytic cleavage would result in a 2A that no longer had this property. When expressed as any of the above described fusion proteins, the endogenous 2A NLS would still transport the fusion protein into the nucleus. Specific examples could include replacement of the terminal Asn-Pro-Gly sequence with an Ala-Pro-Gly sequence, and then fusion of this gene with a gene for the EMCV protease 3C, 3CD or 3BCD. The effect of adding these proteins to 2A, and using the 2A NLS to transport both to the nucleus would result in a fast and efficient turnoff of pol-II activity, but not that of pol-I or pol-III.

In the fourth embodiment, it is encompassed that the 2A can be used in combination with other cardiovirus genes. One example enables the expression of 2A from non-replicating cDNA or RNA. Specifically, it is possible the 2A induced shutoff of pol-II transcription and cap-dependent translation could be further enhanced or made to occur even more rapidly if one or more additional EMCV viral proteins were added to the expression systems, as shown above.

In this embodiment, it is envisioned that the tricistronic or bicistronic cDNA or RNA constructions described above with the gene1 sequence could be replaced with an EMCV gene encoding protein 3BCD, a known form of the viral protease that is capable of targeting the nucleus. This would (by itself) bring about a faster rate of pol-II inhibition, via a mechanism that amplifies the parallel 2A-mediated inhibition of the same enzyme. The combination of these inhibitory two viral activities should hasten cellular transcriptional shutoff, and consequently, the switch from cap-dependent to IRES-dependent translational activity for the enhanced expression of any IRES-driven foreign gene (i.e. gene2).

In another example, it is encompassed that the 2A expressed from self-replicating cDNA could be introduced into cells. Specifically, picornaviral replicon sequences have been described, in which the viral capsid sequences of a viral cDNA are replaced with a reporter gene, or gene encoding a desired expression protein. In particular, replicons which use two 2A-encoded primary cleavage sequences to release the protein product of the added gene have been described (Binder, J. J., Hoffman, M. A., and Palmenberg, A. C. (2003) Virology, 312(2):481-94.

Thus, as used here the term "replicon(s)" includes, but is not limited to, self-replicating recombinant positive strand RNA molecules. The term "positive strand" as used herein includes, but is not limited to an RNA strand that directly encodes a protein. Replicons can be constructed by deleting all or part of capsid coding sequences and retaining all coding and non-coding sequences necessary for replication. Retention of genomic replication sequences allows the expression of viral and/or heterologous gene products in appropriate cells. For example, the CRE, found in the Mengo virus VP2 gene, is essential for replication. Also, the term "expression" or any variation thereof as used herein includes, but is not limited to, giving rise to or encoding the production of a protein or part of a protein.

Furthermore, in accordance with the invention, replicons can be prepared by several approaches as described in detail below. For example, one approach, the appropriate DNA sequences are transcribed in vitro using a DNA-dependant RNA polymerase, such as bacteriophage T7, T3, or SP6 polymerase. In another approach, replicons can be produced by transfecting animal cells with a plasmid containing appropriate DNA sequences and then isolating replicon RNA from the transfected cells.

Applicants note that as used herein, the term "transfection" includes, but is not limited to, the introduction of DNA or RNA into a cell by means of electroporation, DEAE-Dextran treatment, calcium phosphate precipitation, liposomes (e.g., lipofectin), protein packaging (e.g., in pseudo-viral particles), protamine condensation, or any other means of introducing DNA or RNA into a cell.

Also, in this embodiment, it is envisioned that an EMCV or Mengo replicon cDNA sequence linked to an upstream pol-II promoter, such as for example, a constitutive or inducible CMV promoter sequence, and also and encoding an exogenous reporter gene or expression gene of interest (e.g., human interferon), would be transfected into cells. The constitutive (or induced) transcription of this sequence would produce an mRNA, exported to the cytoplasm where it would undergo translation, producing the 2A protein, and all the other viral proteins from the P2-P3 region that were necessary and sufficient for transcript amplification in an RNA-RNA replication cycle. The endogenous, heterologous gene would thus be amplified, and its expression, as driven by the viral IRES inherent in the replicon sequence, would not be shut off by subsequent 2A activities. The combination of a DNA-based gene-introduction system, transcript amplification by RNA replication, and 2A-induced cap-dependent mRNA shutoff, should result in huge levels of targeted gene expression, relative to any other known method (see FIG. 4G).

Furthermore, the present invention provides for kits, wherein the kits are composed of at least one of the novel nucleic acid constructs described hereinabove. More preferably, it is envisioned that a kit of the invention will include at least one nucleic acid construct having either a polynucleotide sequence encoding a 2A polypeptide operably linked to a DNA-dependent RNA polymerase promoter or to an IRES sequence.

APPLICABILITY OF THE INVENTION

Applicants envision that the nucleic acid constructs described by the present invention may be suitable for use in a wide variety of potential applications. For example, the constructs can be used to express heterologous proteins in eukaryotic or animal cells or an animal host by inserting sequences coding for heterologous polypeptides into the constructs and introducing the constructs into the animal cells or the animal host. Host cells used for this application are preferably human but can be from dog, cat, pig, cow, chicken, mouse, or horse.

It is envisioned that the replicon constructs can be introduced into the host by several means, including intramuscular injection, gold particle-coated gene gun delivery, protein-packaged injection (e.g., packaged in pseudo-viral particles), protamine-condensed injection, or liposome-encapsulated injection. For example, a Mengo virus-derived construct allows the transient expression of a toxic protein or a proapoptotic protein in a solid tumor by direct injection, thus providing a form of anti-tumor gene therapy. Thus, the novel constructs can be used to down-regulate mRNA cellular transcription and/or cap-dependent translation in eukaryotic cells.

In addition, recombinant replicon constructs of the invention can be used in vitro or in vivo in order to express conveniently detected reporter protein, as described in detail below. These constructs can be used to monitor RNA replication and RNA delivery, thereby allowing for optimization of animal cell transfection or RNA delivery into an animal host. Finally, these constructs can for example, be used to increase protein expression to conduct further studies on protein characterization, protein production, or protein localization.

It is further envisioned that the constructs of the invention could be used to induce an immune response against the encoded heterologous protein in an animal recipient. Thus, the constructs of the instant invention along with a pharmaceutically acceptable carrier can comprise a vaccine. Possible pharmaceutical carriers include, but are not limited to, sterile liquids, such as water, oils, including petroleum oil, animal oil, vegetable oil, peanut oil, soybean oil, mineral oil, sesame oil, saline solutions, aqueous dextrose, glycerol solutions, liposomes, gold particles, and protamine or any other protein or molecule able to condense the RNA. It is noted that the suitably designed constructs of the invention can also, for example, be injected in the form of naked RNA. The term "naked" as used herein includes, but is not limited to, an RNA molecule not associated with any proteins.

EXAMPLES

Example 1

Protein 2A Inhibition of Cap-Dependent mRNA Translation

Materials and Methods
Viruses and Cells
Recombinant vMwt (Mengo), vMC$_0$ (Mengo) and vEC$_9$ (*encephalomyocarditis*) have been described (Hahn and Palmenberg, 1995; Martin et al., 1996) (species *encephalomyocarditis* virus, genus Cardiovirus, family Picornaviridae). Mutant derivatives vE-2A$_{\Delta58}$ and VE-2A$_{\Delta120}$ have deletions in the 2A coding-region relative to vEC$_9$ that remove 58 and 120 amino acids, respectively (Svitkin et al., 1998). The 19 amino acid COOH-terminal primary cleavage cassette (PCC) is intact and functional in both of these deleted viruses (Hahn and Palmenberg, 2001). Viruses were cultured in HeLa, L-929 or BHK-21 cells, at 37° C. under 5% CO$_2$-air, using RPMI-1640 medium supplemented with penicillin, streptomycin and 10% fetal bovine serum as described (Rueckert and Pallansch, 1981). Typically, subconfluent cell monolayers ($5\times10^6$ cells per 6 cm plate) were infected with virus at a multiplicity (m.o.i.) of 10 plaque-forming units (PFU) per cell.

Recombinant Proteins

Isolation of recombinant Mengo 3C$^{pro}$ and 3D$^{pol}$ from *E. coli* has been described (Hall and Palmenberg, 1996; Duque and Palmenberg, 1996). For convenience, the base numbering systems of Meng-M (#L22089), and EMCV-R (#M81861) are used in all cloning descriptions. To isolate recombinant Mengo 2A protein, the gene (429 b) from pMC$_0$ (b 3462-3890) was amplified by PCR. One primer contained an engineered Nde I site, an ATG codon, and 19 nucleotides derived from the 5' end of the 2A coding region. The second primer contained nucleotides complementary to the 3' end of 2A region, the complement of a TAG codon, and a Bam HI site. The amplicon was subcloned into pET-41b (Novagen), transformed into *E. coli* (strain BL21-DE3-pLysS, Novagen), and the bacteria were amplified in 2xYT broth (37° C.), supplemented with kanamycin (15 mg/ml) and chloramphenicol (30 mg/ml). After induction (5 hrs, with 1 mM isopropylthio-β-D-galactoside), the cells were pelleted and then resuspended in buffer A (1/10 volume, 50 mM Tris-HCl pH 8.5, 1 mM EDTA, 1 mM DTT, 10% glycerol, 1% deoxycholate), lysed by freeze-thaw and subject to centrifugation (27,000×g, 15 min). The pellet was washed twice (buffer A). The inclusion bodies were collected by centrifugation (12,000×g, 5 min), then resuspended in buffer B (0.1% Triton X100, 100 mM NaCl, 6M urea, 50 mM Tris-HCl, pH 8.0, 1 mM PMSF). Insoluble material was removed (12,000 g, 5 min), and the supernatant was dialyzed against TE buffer (10 mM Tris-HCl pH 8.0, 1 mM EDTA, 0.1% Triton X100), then concentrated (Centricon-10, Amicon).

Recombinant Mengo 2B protein (b 3891-4343) was produced in *E. coli* from a pET-41b plasmid (Novagen) that had been engineered to contain the pMC$_0$ 2B gene (450 b), in a manner similar to that described above, except the 2B-specific primers used Nde I and Bam HI sites. Recombinant Mengo 2C protein (b 4344-5318) was also produced from pET-41b, but as a fusion protein that linked a GST-His-Stag segment to the N-terminus of the viral sequence (2C-specific primers, had added Nco I and Bam HI sites). The 2C-containing protein was isolated from disrupted cells and purified by fractionation on a His-column (Novagen). EMCV-R proteins 3A and 3AB (b 5391-5654 and b 5391-5714 respectively) were expressed using procedures similar to those described for 2A and 2B, except the vector, pET-11a (Novagen), was used. Bacteria harboring these plasmids were grown in M9 media supplemented with glucose (0.2%) and rifampicin (1 mM, Sigma). The 3A and 3AB-containing inclusion bodies were resuspended in buffer B1 (0.5% Triton X100, 500 mM NaCl, 50-mM Tris-HCl, pH 8.0, 1 mM PMSF) before clarification and dialysis.

EMCV Replicons

Mengo replicons which express active firefly luciferase after RNA transcript transfection of HeLa cells have been described (Duque and Palmenberg, 2001). A similar EMCV-based replicon (pE-luc) was created by replacing an Spe I to Ava I fragment of pEC$_9$ (b 2426-3509 in 1C-1D coding region) (Hahn and Palmenberg, 1995) with an in-frame firefly luciferase gene (from plasmid pGL2, Novagen), proceeded by an autocatalytic primary cleavage cassette (PCC) derived from the pMC$_0$ 2A-2B junction (84 b of 2A, 30 b of 2B). Translation of T7 RNA transcripts from this replicon produced a full-length, active luciferase enzyme with 10 additional viral amino acids at the N-terminus (from the Mengo PCC), and 29 additional viral amino acids at the C-terminus (from EMCV 1D). A derivative, pE-luc-2A$_{\Delta58}$, deleted 174 bases (b 3777-3951) encoding 58 amino acids (Beretta et al., 1996) from the middle of the EMCV 2A gene. A second derivative, pE-luc-Δ3D$^{pol}$, had a 555 base deletion (b 7177-7732) that effectively removed the active site of viral 3D$^{pol}$ (Eco47 III to Mlu I fragment) Proteins directed by these transcripts were inactive for viral RNA synthesis. Luciferase assays in extracts from transfected HeLa cells were as described (Duque and Palmenberg, 2001).

Eukaryotic 2A Expression Vectors

The Mengo 2A and 2AB genes were engineered into vectors designed to evaluate protein expression in HeLa cells after RNA transcript transfection. The vectors were based on plasmid pCITE-4b (Novagen), which contains an EMCV IRES under the control of a T7 polymerase promoter. Appropriate viral amplicons encoding 2A or 2AB were derived from pMC$_0$ using the Nde I and Bam HI-containing primers described above. Gel-purified fragments were ligated into pCITE DNA that had been digested with these enzymes. When translated in reticulocyte extracts (Shih et al., 1979), T7 transcripts from pCITE-2A and pCITE-2AB produced viral proteins of the expected size and immunogenicity, and the PCC within 2AB cleaved to near completion (results not shown).

The Mengo 2A gene was also engineered into a DNA transformation vector (P$_{min\ CMV}$), where protein expression was under the control of an inducible, minimal cytomegalovirus promoter (pTRE2hyg, Clontech). PCR reactions included one primer with a Bam HI segment linked to a 5' fragment of the EMCV IRES, and another primer complementary to the 3' end of the 2A gene, linked to an Mlu I segment to amplify the IRES-2A sequence from within pCITE-2A. The amplicon was used to replace the Bam HI-Mlu I fragment of pTRE2hyg. When transformed into HeLa cells and induced by tetracycline (2 µg/ml, according to manufacturer's instructions), pIRES-2A produced (capped) transcripts that directed 2A translation under control of the EMCV IRES.

The EMCV 2A gene and derivative 2A$_{\Delta58}$ were engineered into bicistronic, luciferase-containing plasmids under the control of the immediate early promoter sequence of cytomegalovirus (P$_{CMV\ IE}$). Commercial plasmid pIRES (Clontech), was used to link this constitutive CMV promoter to a firefly luciferase gene, followed by an intact EMCV IRES and a multiple cloning site (MCS). The 2A and 2A$_{\Delta58}$ segments from pEC$_9$ and pEC$_9$-2A$_{\Delta58}$ were amplified using flanking primers containing Xba I or Not I sequences, then ligated into the pIRES MSC, after digestion with appropriate enzymes. The pIRES-luc (control), pIRES-luc-2A and pIRES-luc-2A$_{\Delta58}$ plasmids (5 µg) were transformed into HeLa cells ($5\times10^6$ per plate) with transfectin (Qiagen), then incubated (37° C., 5% CO$_2$-air) in the presence of neomycin, following manufacturer's instructions. Luciferase assays in extracts from transformed cells were as described (Duque and Palmenberg, 2001).

Antibodies

Murine monoclonal antibodies (mAbs) raised against recombinant Mengo 3D$^{pol}$ and capsid protein 1CD were generously supplied by Dr. H. Duque, Dr. V. Frolov and Dr. O. Frolova (Duque and Palmenberg, 1996). Murine monoclonal and polyclonal antibodies to Mengo 2A, 2B, 2C (GST-HIS-Stag fusion), 3A, 3AB, and 3C$^{pro}$ were developed from recombinant proteins (above) according to described methods (Duque and Palmenberg, 1996; Hall and Palmenberg, 1996). To raise anti-3B antibodies, a water-solubilized synthetic peptide (GPYNETARVKPKTLQLLDIQ) SEQ. ID. NO. 1, corresponding to the complete EMCV 3B$^{VPg}$ protein (b 5655-5714) was conjugated with KLH (keyhole limpet hemocyanin) and used to immunize mice (40 µg, over 6 doses, during 18 weeks). Antibody reagents raised against each viral protein were tested for high-titer ELISA reactivity with the corresponding recombinant protein. The antibody subtypes (Ig) produced by each line (hybridoma or ascites) were identified with commercial test kits (Sigma). Goat polyclonal antibodies to nucleolar-specific proteins, B23 and C23, were purchased (Santa-Cruz Biotechnology, Inc.)

Immunodetection of Proteins

Western assays used cells harvested at appropriate times post infection (PI). The cells were washed with phosphate-buffered saline, lysed by freeze-thaw (3×), and the clarified supernatants were fractionated by SDS-PAGE, then blotted onto polyvinylidene fluoride membranes (Immobilon-P, Millipore) as described (Duque and Palmenberg, 2001). Bands with positive reactions against the appropriate antibodies (typically, 1:2,000 dilution of ascites), were visualized by chemiluminescence (ECL kit, Amersham Pharmacia Biotech, Inc.), after secondary reactions with appropriate anti-mouse antibodies, conjugated with horseradish peroxidase (1:2,000 dilution, Amersham Biosciences). Mobility shift assays with viral proteins by non-denaturing 4% PAGE were similar to those described (Kiessig et al., 2001; Stern and Frieden, 1993). Briefly, recombinant 2A protein (30 ng), and nuclear extracts or whole cell lysates from HeLa cells (20 µl, Promega) were co-incubated in buffer (20 mM HEPES, pH 8.0, 100 mM KCl, 1 mM EDTA, 5 mM MgCl$_2$, 0.1% Triton X100 and 1 mM DTT) for 1 hour at 30° C. The samples were fractionated by non-denaturing PAGE (20° C., TBE buffer, 200 V), transferred to membranes, and the bands were visualized by Western assay (Ab-B23 or mAb-2A), using ECL (anti-goat or anti-mouse secondary antibodies, respectively).

Immunofluorescence Microscopy

HeLa or L-929 cell monolayers were grown on coverslips to 50-70% confluence then infected (10 PFU/cell), transfected (1.5 µg RNA per 5×10$^6$ cells) or transformed (5 µg DNA per 5×10$^6$ cells) as described above. At appropriate intervals (37° C. under 5% CO$_2$-air), the cells were rinsed with phosphate-buffered saline, fixed with paraformaldehyde, permeabilized (0.3% Triton X-100), then incubated (1 hr, 20° C.) with the desired primary antibody (1:2000 dilution in blocking solution), as described (Amineva et al., 2003). After reaction with a corresponding secondary antibody, the slips were mounted (Vectashield mounting medium, Vectorlab) and label location was visualized by laser-scanning confocal microscopy. Image capture used MCR 1024 LaserSharp software (Bio-Rad, Inc.). For double-label experiments, primary antibodies raised in different species (e.g., mouse and rabbit) were selected, and the samples were developed with appropriate, corresponding secondary antibodies (1:100 dilution) conjugated with fluorescein isothiocyanate (FITC) or Texas Red (Santa Cruz Biotechnology, Inc.). RNA labels incorporated fluorescein-12-UTP (Sigma) into permeabilized cells before the paraformaldehyde fixation step, as described previously (Aminev et al., 2003; Amineva et al., 2003). A fluorescent-tagged wheat germ agglutinin (WGA, Molecular Probes, Inc.) was used to highlight and identify Golgi and nuclear membrane locations. SYTOX stain (Molecular Probe Inc.) was used to localize dsDNA within cells. Rabbit polyclonal serum against ribophorin II.

Results and Discussion

Recombinant Viral Proteins

In accordance with the present invention applicants have described the cloning and isolation of recombinant Mengo 3C$^{pro}$ and 3D$^{pol}$, and the characterization of murine monoclonal antibodies raised against these proteins (Duque and Palmenberg, 1996; Hall and Palmenberg, 1996). Using similar procedures, the Mengo genes for 2A, 2B, 2C, 3A and 3AB were cloned into bacterial expression vectors. The 2C gene was linked to a GST-His-Stag fragment in a construction which facilitated subsequent protein solubility and isolation, but the other proteins were synthesized as unmodified, non-fusion sequences. Most of the expressed material was produced in inclusion bodies which were readily solubilized by detergent and dialysis. A typical yield was about 100 mg of protein per liter of culture. After verification of protein size and purity by SDS-PAGE, the preparations were inoculated into mice. To complete the panel, a synthetic peptide with the Mengo 3B$^{VPg}$ sequence was inoculated in parallel. Animals which seroconverted to their respective proteins (ELISA) were exsanguinated (polyclonal sera) and their spleens were used to develop hybridomas producing monoclonal antibodies and subsequent high-titer ascites (Duque and Palmenberg, 1996). Each reagent was tested for ELISA reactivity with its recombinant protein and also in Western assays with lysates from Mengo-infected HeLa cells, so the precursor recognition capacity could be characterized. As an example, five IgG-producing hybridoma lines were generated to 2A (5A12, 5F5, 4D10, 3A6, 1C7), each of which reacted strongly with recombinant protein in ELISA, immunoprecipitated its targets from infected cell lysates, and stained infected cells by confocal microscopy. But only two of these 2A mAbs (5A12 and 5F5) also gave positive signals in Western assays with infected lysates. When used at appropriate concentrations (typically, 1:2,000 dilution of ascites), only a few mAbs within the entire panel of new reagents showed any reactivity with cellular proteins. Nevertheless, care was taken in every experiment to include uninfected cell samples for the identification of spurious signals.

Figure 5:
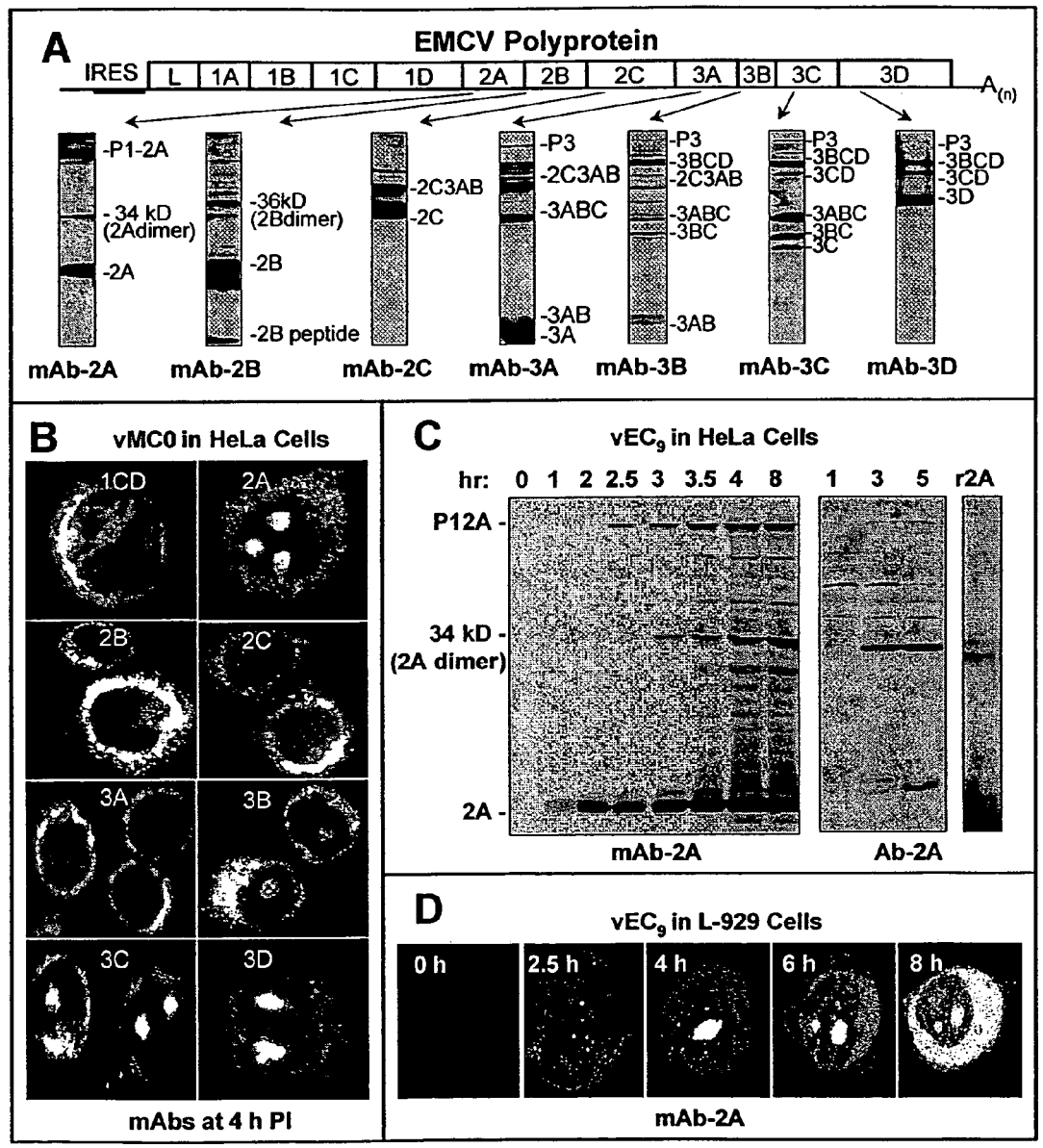
FIGS. 5A-D profile the various recombinant viral proteins. Panel A shows results from an antibody activity experiment. A map of the EMCV genome shows the protein order within polyprotein reading frame. HeLa cells infected with $vEC_9$ (m.o.i. of 10) were harvested (4 hr PI), and analyzed for viral protein content in Western assays with mAbs to 2A (5A12), 2B (3G3), 2C (9H11), 3A (3D2), $3B^{VPg}$ (2E4), $3C^{pro}$ (1D12), and $3D^{pol}$ (H. Duque). Panel B shows results from cell staining experiments. The same mAb panel (and mAb-1CD from V. Frolov), was used to stain infected cells for visualization by confocal laser microscopy using an anti-mouse, FITC-conjugated secondary antibody. Panel C shows results from protein 2A accumulation experiments. Infected HeLa cells were harvested at the indicated times, fractionated by SDS-PAGE, then probed by Western analyses using mAb-2A (5A12) or Ab-2A (murine polyclonal serum). Recombinant 2A (r2A) is included as a marker. Panel D shows L-292 cells were infected with vMwt (m.o.i. of 10), and harvested at the indicated times for confocal microscope visualization, using the above mAb-2A.

The Western profiles of selected mAbs are shown in FIG. 5A. Although cardiovirus precursor identification is well characterized for this gel system (Palmenberg and Rueckert, 1982; Parks et al., 1986), in all cases, the band assignments were confirmed by stripping and reprobing the blots with various combinations of mAbs (results not shown). Kinetic analyses of viral proteins synthesized in EMCV-infected cells will be published in detail elsewhere (Aminev and Palmenberg, manuscript in preparation), but to summarize, the mAbs proved quite adept at detecting "missing-link" precursors, like 2C3AB, 2C3A, 3BCD, 3BC and 3ABC. Moreover, some mAbs also detected the surprising presence of stable populations of dimers or other multimers for 2A (16.7 kD, pI of 9.2) and 2B (16.5 kD, pI of 7.9). An infection time course (FIG. 5C) indicated that by 3 h PI, nearly 10% of the 2A signal migrated as a P1-2A capsid precursor and another 10% migrated in the position of a 34 kD complex on SDS-PAGE. This complex was not reactive to mAbs against the flanking proteins 1D or 2B (results not shown), and was therefore not derived from a previously undescribed precursor. A gel fractionating the recombinant 2A protein (FIG. 5C, r2A lane) also had the 34 kD band, consistent with its identification as an SDS-resistant dimer form. Notably, the Mengo 2A sequence does not encode cysteine, but it does predict a helix-loop-helix domain, similar to a type that commonly mediates dimerization among certain transcription factors (Murre et al., 1989), or dimerization of the herpesvirus MEQ protein (Liu et al., 1997). Recombinant 2B protein (results not shown), or 2B from infected cells, likewise had a 36 kD form that probably also represented dimers.

Protein 2A Localizes to Nucleoli

Figure 6:
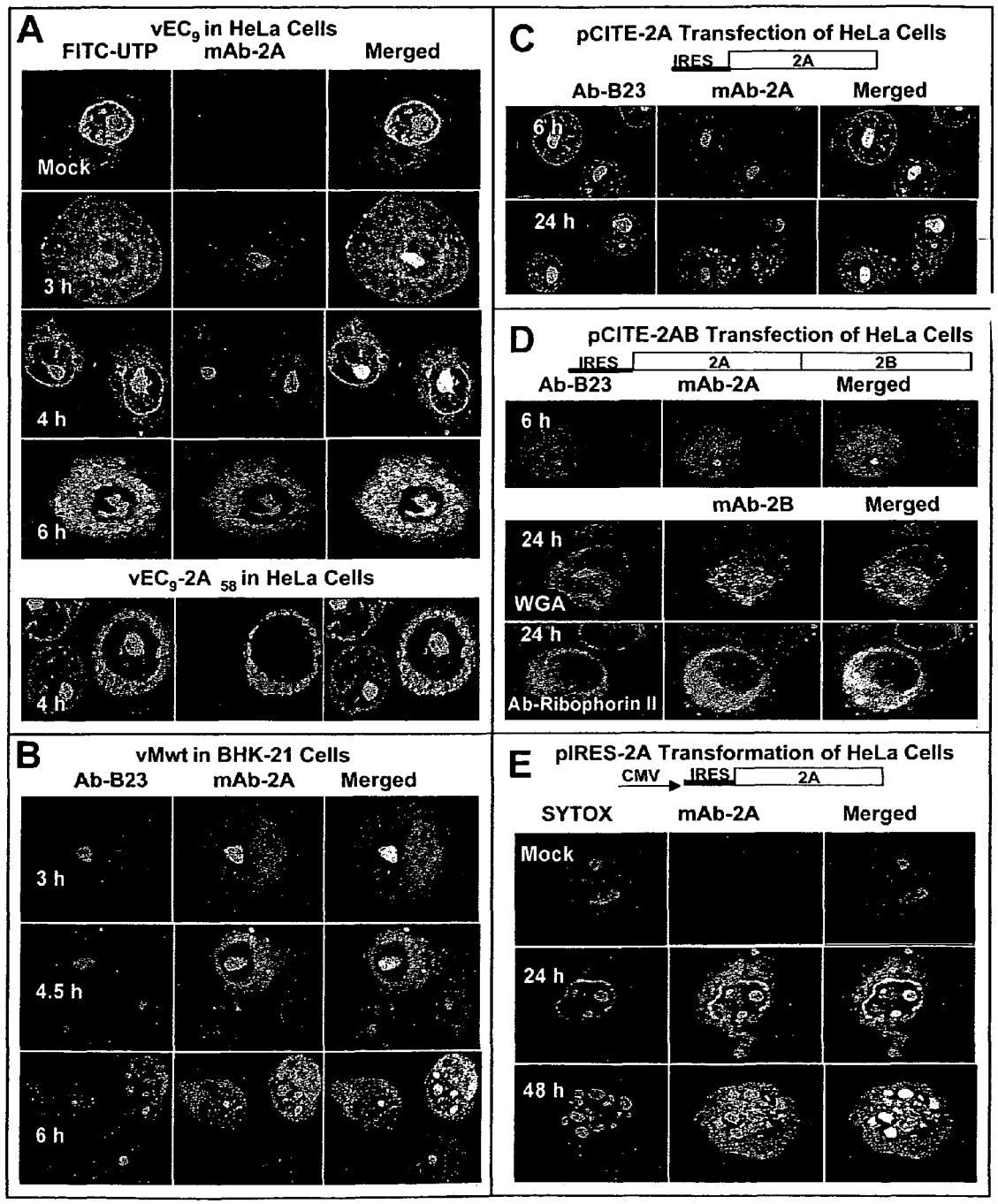
FIGS. 6A-E show the localization of protein 2A to the nucleoli. Panel A provides results from RNA synthesis experiments. HeLa cells were infected with $vEC_9$ or $vEC_9$-$2A_{\Delta58}$. After 2, 4 or 6 hrs, the cells were pulse-labeled with FITC-conjugated UTP, and 30 min later, they were fixed and stained with mAb-2A. The secondary anti-mouse antibody was conjugated to Texas Red. Panel B shows that BHK-21 cells were infected with vMwt as in Panel A, then co-stained with Ab-B23 (goat) plus mAb-2A then visualized with appropriate secondary antibodies. Panel C provides results from cell transfections with a 2A transcription vector. Transcript RNAs from pCITE-2A were transfected into HeLa cells as described in Methods. At the indicated times, cells were fixed and stained with mAb-2A and Ab-B23, as indicated. Panel D provides results from cell transfections with a 2AB transcription vector. Transcript RNAs from pCITE-2AB were treated as in Panel C. The cells were fixed and stained with mAb-2A, mAb-2B, Ab-B23, Ab-ribophorin II, or WGA, as indicated. Panel E shows results from HeLa cells transformed with pIRES-2A cDNA, induced by tetracycline, harvested at the indicated times, and stained similar to Panel C, except that SYTOX was used to visualize DNA.

Having identified the cohort of viral precursors (or multimers) that gave rise to immunogenic signals, the next step was to identify within cells, their preferred location. The replication of infectious picornaviruses is a cytoplasmic process. Indeed, infectious poliovirus can be completely synthesized in cell-free extracts (Molla et al., 1991), and this virus will replicate in enucleated cells (Detjen et al., 1978). Electron microscopy studies with poliovirus (using mAbs to 2C and $3D^{pol}$) have confirmed repeatedly that genome translation and replication take place in cytoplasmic foci where the smooth and rough endoplasmic reticulum (ER) are in near conjunction (Bienz et al., 1983; Bienz et al., 1992; Egger et al., 2000; Bienz and Egger, 1995). Our first microscopy experiments with cardiovirus mAbs were in agreement with these findings, in that signals from capsid proteins (1CD) and nonstructural proteins 2B, 2C and 3A (FIG. 5B) colocalized with ribophorin II and WGA markers for the ER and Golgi (e.g., FIG. 6D). Signals from 2A, $3B^{VPg}$, $3C^{pro}$ and $3D^{pol}$, also colocalized with the ER. However, these proteins showed additional, unmistakable targeting to nucleoli as well (FIG. 5B). Even at the earliest times of EMCV infection (v$EC_9$), the nucleoli glowed brightly from reactions with mAbs to 2A, $3C^{pro}$, $3D^{pro}$ or $3B^{VPg}$. The same results were evident with vMwt virus in L-929 cells (FIG. 5D) or BHK-21 cells (FIG. 6B). A simple time course of 2A localization during vMwt-infection of L-929 cells (FIG. 5D) indicated the earliest punctate nuclear foci (2.5 hr) were progressively replaced with dense nucleolar signals (4-6 hr), and finally by diffuse cytoplasmic labeling in addition to the nucleolar stains.

Figure 2:
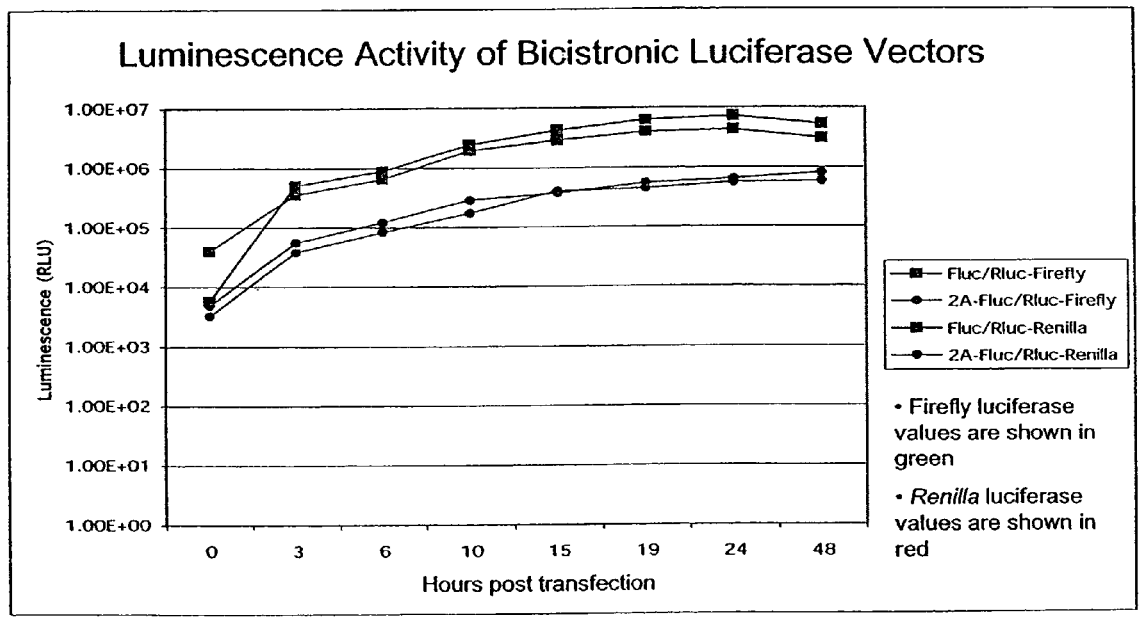
FIG. 2 graphically illustrates relative luminescence of bicistronic luciferase vectors at various times post transfection. HeLa cells were transfected with either Fluc/Rluc or 2A-Fluc/Rluc DNA plasmids in media A without serum, using liposome technique. Cells were allowed to incubate with this mix for 4 hours at 37° C./5% $CO_2$. Media A with serum was then added to the plates. At various times post transfection, cells were harvested, washed twice with PBS and lysed by the addition of 1× passive lysis buffer (Promega). Lysis was continued for 15 minutes at room temperature with shaking. Cell lysates were collected at stored at –20° C. Dual luciferase assay conditions were carried out according t the manufactures protocol (Promega). Values are expressed in relative light units (RLU) per sample.
Figure 3:
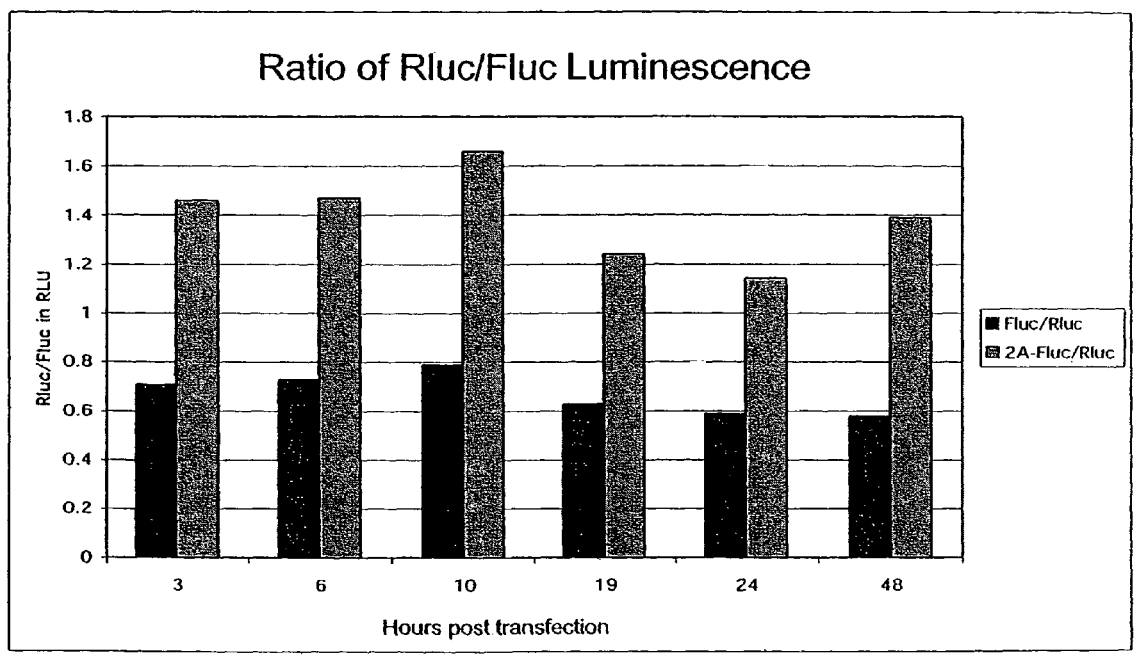
FIG. 3 is a graph illustrating the ratio of the luminescence of Renilla luciferase to Firefly luciferase (from data in FIG. 14) for each of the two bicistronic luciferase constructs at various times post transfection.

FIG. 2A (top 4 panels) shows a HeLa cell infection by v$EC_9$ at 2, 4 and 6 hr PI. This 2A antibody was not reactive to mock-infected cells (top panel), but in infected cells, the signal colocalized with a pulse-labeled FITC-UTP stain that was added to mark the sites of ongoing RNA synthesis. The densest nuclear RNA stains (green) identify transcriptionally active nucleoli and are also the sites where ribosomal chaperone protein B23 (nucleophosmin) was significantly concentrated (FIG. 6B). The panels in FIG. 6B are from vMwt-infected BHK-21 cells taken at 3, 4.5 and 6 hr PI. EMCV productively infects only about 10% of these cells, compared to nearly 100% of HeLa cells (Martin et al., 2000), so the antibody staining also highlights the obvious contrasts between infected and uninfected cells within the same field. In this embodiment, the B23 nucleolar staining (red) is evident in all cells, making the cytoplasmic (green) and nucleolar (yellow) distribution of 2A in the infected cells, all the more apparent. Similar experiments with antibodies against nucleolin C23 protein (Li et al., 1996) had nearly identical patterns (results not shown).

As described above and shown in FIG. 5B, the localization 2A to nucleoli of infected cells was not unique to this protein. Protease ($3C^{pro}$), polymerase ($3D^{pol}$) and VPg ($3B^{VPg}$) antibodies gave similar signals in all infected cells. The P3-region protein reactions are also described herein, but in order to learn whether these signals were co-dependent, it became necessary to express 2A from various genome contexts within cells. Recombinant EMCV with 2A deletions are known to be infectious as long as the COOH-terminal 19 amino acids of 2A (PCC) are left intact to catalyze the primary cleavage of the polyprotein (Hahn and Palmenberg, 2001). Viruses vE-$2A_{A58}$ and vE-$2A_{A120}$, for example, grow well in cells, albeit with small plaque phenotypes because of their inability to shut off host protein synthesis or host mRNA transcription (Svitkin et al., 1998). After infection with these mutants, mAb-2A (5A12) which recognizes a PCC epitope, localized the remaining 2A fragment(s) to the ER, but not the nucleolus, confirming that nuclear targeting required an intact 2A (FIG. 6A, bottom panel). Other viral proteins were not essential to this process because transfection with RNA transcripts linking the 2A gene to a viral IRES (pCITE-2A), also resulted in strong nucleolar signals (FIG. 6C). Similar transcripts expressing 2AB (pCITE-2AB), showed that only the 2A protein became nuclear, while 2B moved to the Golgi (WGA stain) or ER (Ab-ribophorin II) as soon as the fragments were separated by the co-translational activity of the encoded PCC (FIG. 6D). In yet another construction, 2A expressed after tetracycline induction of a cDNA containing a CMV promoter (pIRES-2A) also localized to nucleoli almost immediately after synthesis (FIG. 6E). Interestingly, under these conditions, the cells rounded up and died within 24-48 hrs of induction, presumably from the toxic effects of 2A overexpression (FIG. 6E, bottom panel).

Protein 2A and B23

The sequence and structural elements that allow mammalian proteins to shuttle into nuclei and nucleoli are not very well understood. No cardioviral proteins, including 2A, have canonical nuclear localization signals (NLS), that exactly match the three classical types described for eukaryotic proteins using the importin α or importin β pathways (Michael, 2000; Hicks and Raikhel, 1995). Nor do the viral sequences suggest an obvious small nuclear RNA (snRNA) binding motif that could easily explain their targeting. On the other hand, 2A does have a rather basic amino acid profile (18% H+K+R, pI of 9.23), and contains at least one segment resembling the [KR][KR]$X_{10}$[3 of 5: KRHW] sequence that defines about 50% of known nuclear proteins in eukaryotic cells (Michael, 2000). Moreover, a subset of this segment (FIG. 7) is a reasonable match with the nuclear targeting pattern, common to many yeast ribosomal proteins (YRP, reviewed in (Stuger et al., 2000)). Mammalian r-proteins use a specialized nuclear import pathway that does not involve importin α. The YRP-NLS, which may or may not have a functional analog in mammals, follows the general pattern of $(K/R)_3X_{1-4}$, preceded or followed by Gly or Pro. All known cardioviral 2A proteins have this pattern just upstream of the PCC, although it is deleted in the vE-$2A_{A58}$ virus. Site-directed mutagenesis studies are currently underway to map the function of this region in 2A, and determine whether this small motif is uniquely responsible for nuclear targeting.

The nucleolar signals within 2A are yet another unknown. Nucleoli, of course, are the genome sites where pol-I transcribes dense clusters of rRNA genes into a 45S pre-rRNA. These ribosome factories splice pre-rRNA into 18S, 28S and 5.8S fragments as the 40S and 60S ribosomal subunits are assembled on site. Ribosomal 5S rRNA, synthesized by pol-III, and ribosomal proteins translated in the cytoplasm, are shuttled into complex nucleolar scaffolds as the ribosomes are built (Melese and Xue, 1995). The most curious observation about nucleoli in Mengo-infected cells was that they never shut off their synthesis. Nucleolar antibodies (B23 and C23), viral mAbs (2A), and fluorescein-UTP labels showed progressively brighter foci throughout the infection and continuous rRNA synthesis (FIG. 6A). In contrast, during polio or rhinovirus infection, nucleoli become diffuse and disassembled (Amineva et al., 2003), and in fact, the whole nuclei eventually become physically indistinct, presumably as the virus perverts essential pathways for transport and repair (Waggoner and Sarnow, 1998).

Figure 8:
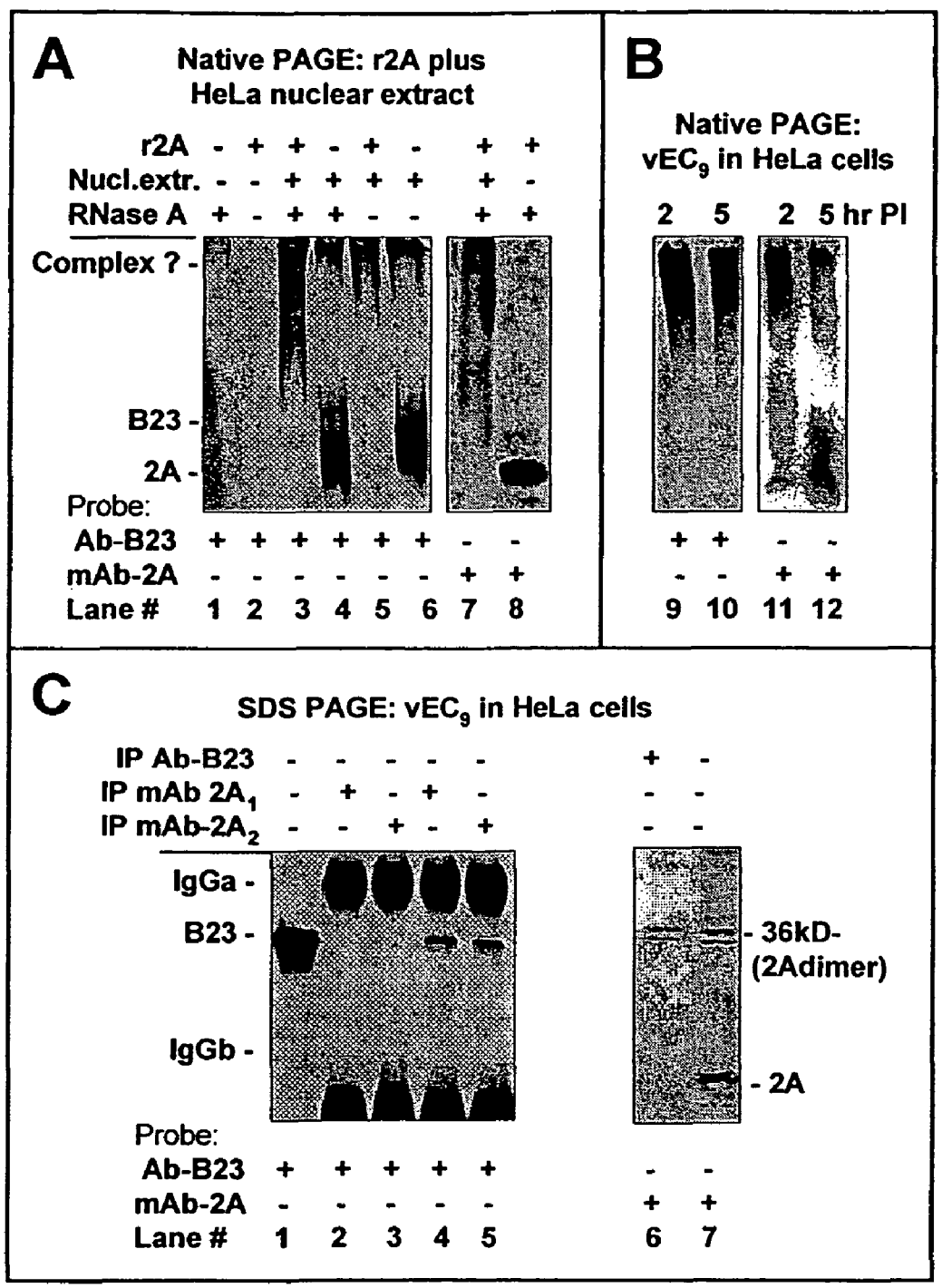
FIGS. 8A-C show the interaction between protein 2A and B23. Panel A provides results from a B23 shift. Electromobility shift assays were as described in the Methods below. The samples were treated with RNaseA (50 µg/ml) as indicated, then fractionated by 4% native PAGE. After blotting onto membranes, the bands were visualized in Western assays using Ab-B23 (lanes 1-6) or mAb-2A (5A12, lanes 7-8). Panel B shows nuclear localization of Protein B23. HeLa cells infected with $vEC_9$ (m.o.i. of 10) were harvested at the indicated times PI, fractionated by 4% native PAGE, and the B23 and 2A reactive bands were visualized in Western assays using Ab-B23 or mAb-2A. Panel C provides results from a series of immunoprecipitation experiments. Infected (lanes 4, 5, 6, 7) or mock-infected (lanes 1, 2, 3) HeLa cell extracts were harvested at 4 hrs PI. Reactive proteins were immunoprecipitated with mAb-$2A_1$ (5A12, lanes 2 and 4), mAb-$2A_2$ (5F5, lanes 3 and 5), or Ab-B23 (lane 6), then fractionated by SDS-PAGE. Lane 7 contains a sample of the infected cell lysate. The bands were stained using Ab-B23 or mAb-2A (5A12) as indicated. Lane 1 contains mock-infected HeLa cell lysate (B23 marker) that was not immunoprecipitated. The mouse, anti-goat secondary antibody used for ECL (lanes 1-5), also reacted with IgG chains from the murine mAb-2A. The rabbit, anti-mouse secondary antibody (lanes 6 and 7), did not have a similar reactivity with the residual (goat polyclonal) Ab-B23 chains.

The requirements for protein accumulation in nucleoli are still unclear, although binding to nucleolar proteins or nucleolar RNAs (rRNA) is probably a common theme (Valdez et al., 1994; Li et al., 1996). In this regard, the close association between B23 and cardiovirus 2A (or the 2A dimer?) by microscopic localization, could not be coincidental (FIG. 6BCD). During HIV infections, B23 interacts with Rev, Rex, and Tat viral proteins and helps to direct them into nucleoli (Szebeni et al., 1997; Stauber and Pavlakis, 1998; Hiscox, 2002; Adachi et al., 1993). As a preliminary test for a similar association we added recombinant 2A to nuclear extracts from uninfected HeLa cells and observed a shift in the B23 immunogenic signal towards the top of the gel when the samples were fractionated under non-denaturing conditions (FIG. 8A). The gel shift required the presence of r2A (lane 3 vs 4, or 5 vs 6), but was not sensitive to treatment with RNaseA (lane 4 vs 6). The slower migrating complexes, whether formed by mixing uninfected extracts with r2A (FIG. 8A), or fractionated from infected cells (FIG. 8B), were co-reactive with antibodies against 2A as well as B23, suggesting a direct interaction, or reaction within a common heterologous complex.

In parallel experiments, two different mAb-2A samples (5A12, 5F5) were tested for their ability to immunoprecipitate B23 from infected cell extracts (FIG. 8C). Both extracted an Ab-B23 reactive band of the same size as authentic B23 (lane 1, marker) from infected cells (lanes 4 and 5), but not from uninfected cells (lanes 2 and 3). The reciprocal experiment showed that Ab-B23 was able to immunoprecipitate 2A dimers from cell extracts after 4 hrs (lane 6) of infection. Although strong evidence for an direct interaction between B23 and 2A or perhaps even a 2A dimer, these collective results could also indicate a mutual participation in one or more complexes of cellular proteins (e.g., ribosomes). Nevertheless, our preferred working hypothesis is that B23 may be required to chaperone 2A into nucleoli during infection in the same manner it chaperones ribosomal proteins or HIV proteins. It is believed that if this hypothesis is true this 2A probably encodes the YRP-type NLS to allow defacto behaviour as a ribosomal protein mimic, thereby facilitating quick and efficient nucleolar transport.

Protein 2A Shuts Off Cap-Dependent Translation

In accordance with the present invention, applicants believe that viruses need such an unusual nuclear function, or nucleolar-targeting protein because RNA viruses live short, intense predominantly cytoplasmic lifecycles. Within 6-8 hrs, they infect, translate, synthesize RNA, package their progeny and exit the cell, all while in direct competition with host for metabolic resources. Preferably, they can simultaneously avoid activating the plethora of host-encoded antiviral defense systems that could trigger an abortive infection. A virus can gain an edge in this competition if it inhibits detrimental cellular responses or effectively sequesters metabolic resources. Picornaviruses do both. Observations dating back at least 40 years report a marked shutoff of host mRNA synthesis following Mengo infection of L-929 cells (Baltimore and Franklin, 1962). Careful measurement of the DNA-dependent RNA polymerase levels (pol-II) in infected cells showed these enzymes were not damaged or denatured, but nonetheless were unable to initiate new mRNA synthesis in the manner of mock-infected cells (Apriletti and Penhoet, 1978; Baltimore and Franklin, 1962). At the same time, there was a strong, parallel shift from cap-dependent (host) to IRES-dependent (viral) translation, during the EMCV infectious cycle (Svitkin et al., 1978). More recently, Nahum Sonenberg's group conducted an elegant series of experiments clearly connecting EMCV 2A to the shutoff of host protein synthesis during viral infection (Svitkin et al., 1998). Those experiments implicated the PI3 kinase-FRAP signaling pathway in this process, but did not determine the precise mechanism by which cap-dependent inhibition was achieved. The 2A proteins of polio- and rhinoviruses are proteases, which, among other duties, cleave translational factor eIF-4G to inactivate the host's cap-binding complex (Krausslich et al., 1987; Haghighat et al., 1996; Liebig et al., 1993). In aphthoviruses, the leader protein carries out similar cleavages (Guame et al., 1998). By inactivating eIF-4G, these viruses effectively prevent host mRNA translation while they themselves continue to translate by virtue of their IRESs. But in EMCV-infected cells, eIF-4G is not cleaved, 2A is not a protease (nor is the leader), and the shut off of host protein synthesis, while clearly evident, is neither as rapid nor as extensive as that caused by polio (Jen et al., 1980).

Figure 9:
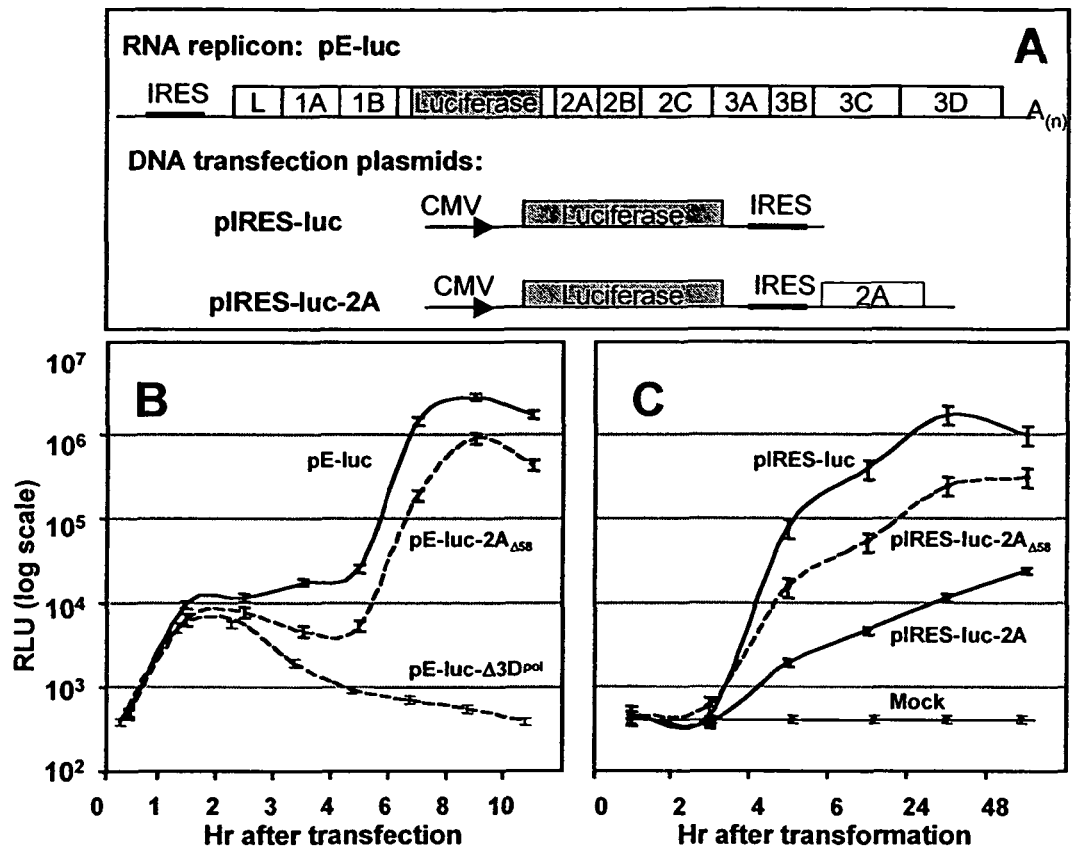
FIGS. 9A-C show that protein 2A has the ability to shut off cap-dependent translation. Panel A: shows nucleic acid construct maps. EMCV-based replicon pE-luc, and transformation plasmids pIRES-luc, pIRES-luc-$\Delta3D^{pol}$, pIRES-luc-2A and pIRES-luc-$2A_{\Delta58}$ are described herein the methods. Panel B provides results from replicon assay experiments. Luciferase activity in RNA transfected HeLa cells was determined as in Methods. All samples (20 µl of lysate) were prepared and assayed in parallel. Panel C provides results transformation assays. HeLa cells were transformed (or mock transformed) with plasmid cDNAs containing constitutively active CMV promoter sequences, as described in Methods. At the indicated times post-transformation, cell extracts were harvested and tested for luciferase activity. All samples (20 µl of lysate) were prepared and assayed in parallel. Error bars indicate the variation in duplicate samples.

To resolve these questions, we are only now in the process of probing cells for specific phenotypes associated with the cardiovirus 2A protein, in the absence of infection. The pIRES-2A cDNA described above, is certainly a useful tool, because of the rapidity and totality with which the induced 2A kills cells. On the other hand, rapid cell death can sometimes make it even harder to tease apart the lethal pathways if there is an inadvertent triggering of unwarranted apoptotic responses. Among our more subtle approaches are new EMCV cDNAs encoding RNA replicons or bicistronic reporter mRNAs. A replicon is a non-infectious viral RNA transcript, where a portion of the capsid-coding region has been replaced by a reporter gene, typically luciferase (FIG. 9A). Reporter activity after transfection is usually sensitive enough to discriminate between input transcript RNA translation (1-4 hr post-transfection) and replicated progeny RNA translation (4-8 hr post-transfection). In the case of EMCV replicons harboring the $2A_{\Delta 58}$ deletion, we found both translational phases were somewhat diminished relative to wild-type (FIG. 9B), indicating that the full-length form of the protein was providing a metabolic boost to the entire replication cycle, even from the earliest times of expression. A wild-type 2A then, capable of nucleolar translocation and host translational shutoff, confers a competitive advantage to its virus or replicon. To determine whether the 2A protein acted alone in this process, special bicistronic cDNAs were engineered, placing a luciferase reporter gene under the translational control of a 5' cap, and linked to a downstream 2A gene under the translational control of an EMCV IRES (FIG. 9A). Consequent transformation of cells resulted in ample expression of luciferase from control cDNAs (pIRES-luc), but co-expression of 2A from the downstream cistron of the same RNA decreased the cap-dependent luciferase activity by nearly 50 fold over the course of 48 hrs (FIG. 9C). Of particular interest was the additional observation that co-expression of $2A_{\Delta 58}$ in place of the wild-type 2A, was also partially inhibitory to cap-dependent translation (about 3 fold reduction in luc activity), even though this protein was excluded from nucleoli, and must necessarily have exerted its residual function(s) only from the cytoplasm. Therefore, in general these observations are consistent with a novel mechanism for virus-induced host protein shut off in cardioviruses, whereby 2A helps to upregulate the synthesis of new, modified ribosomes that have an inherent preference for IRES-dependent viral genome translation over cap-dependent host mRNA translation.

Example 2

Proteins 2A and 3BCD Inhibition of Cellular mRNA Transcription, but not rRNA Transcription Materials and Methods Cells and Viruses Recombinant viruses vMC$_0$ (Mengovirus), vMwt (Mengovirus), vEC$_9$ (EMCV), vEC$_4$ (EMCV) and wild-type HRV-16 (human rhinovirus) have been described (Hahn and Palmenberg, 1995; Martin et al., 1996; Lee et al., 1995), as has EMCV mutant strain vE-2A$_{A58}$ with a deletion in the 2A coding-region relative to vEC$_9$ that removed 58 amino acids (Svitkin et al., 1998). The 19 amino acid COOH-terminal primary cleavage cassette (PCC), was intact and functional in this deleted virus (Hahn and Palmenberg, 2001). Viruses were cultured in HeLa cells at 37° C. under 5% CO$_2$-air, using RPMI-1640 medium supplemented with penicillin, streptomycin and 10% fetal bovine serum as described (Rueckert and Pallansch, 1981). Typically, subconfluent cell monolayers (5×10$^6$ cells per 6 cm petri dish) were infected with virus at a multiplicity of infection (m.o.i.) of 10 plaque-forming units (PFU) per cell (Rueckert et al., 1980).

Cellular Techniques

Subconfluent HeLa monolayers were infected with vEC$_9$ (m.o.i. of 10) as above. At appropriate times post-infection (PI), the cells were collected and fractionated into nuclear, cytoplasmic and membrane components as described (Hu et al., 1998). Briefly, HeLa cells (5×10$^5$) were washed 3 times with cold PBS, scraped into a tube, and pelleted (400×g, 1 min, 4° C.). The cells were resuspended in buffer A (500 µl, 10 mM Tris-HCl, pH 7.8, 5 mM MgCl$_2$, 10 mM KCl, 0.3 mM EGTA, 0.5 mM DTT, 0.3 M sucrose, 10 mM β-glycerol phosphate, 2 mM ZnCl$_2$) and then incubated on ice for 15 min before NP40 detergent was added to 0.5%. The samples were vortexed, and nuclei were harvested after a centrifugation step (7200×g for 20 sec, 4° C.). The cytoplasmic (supernatant) fractions were removed, and the pellets (nuclei) were washed 3 times with buffer A, then resuspended in buffer B (125 µl, 20 mM Tris-HCl, pH 7.8, 5 mM MgCl$_2$, 320 mM KCl, 0.2 mM EGTA, 0.5 mM DDT, 2 mM ZnCl$_2$). After incubation on ice (15 min, 0° C.) and sonication (10 sec), nuclear extracts and membrane fractions were separated by centrifugation (13,500×g, 15 min, 4° C.). The membrane fractions (pellets) were washed 3 times with buffer B and resuspended (125 µl) in the same buffer.

EMCV Replicons

An EMCV-based replicon (pE-luc) replaced the 1CD coding region of pEC$_9$ with an in-frame firefly luciferase gene, proceeded by an autocatalytic primary cleavage cassette (PCC) derived from the pMC$_0$ 2A-2B junction (Aminev et al., 2003). Translation of T7 RNA transcripts from this replicon produced a full-length, active luciferase enzyme with 10 additional viral amino acids at the N-terminus (from the Mengovirus PCC), and 29 additional viral amino acids at the C-terminus (from EMCV 1D). A derivative, pE-luc-Δ3D$^{pol}$, had a 555 base deletion (Eco47 III-Mlu I fragment) that effectively removed the active site of viral 3D$^{pol}$. Proteins directed by these transcripts were inactive for viral RNA synthesis. Luciferase assays in extracts from transfected HeLa cells were as described (Duque and Palmenberg, 2001).

Mutations

Engineered mutations that inactivated the 2C/3A (QG-QV), 3A/3B (QG-QV), 3B/3C (QG-RG), or the 3C/3D (QG-QC) cleavages sites within the polyprotein sequence of vEC$_4$, have been described (Hall and Palmenberg, 1996a). The genome and polyprotein numbering system used here is according to the published sequence of EMCV-R (GenBank #X00463). Site-specific mutations near the N-terminus of the 3D$^{pol}$ gene (putative NLS sequence) and at the 2B/2C cleavage site (QS-QY) were engineered with a 2-step overlapping PCR method similar to that used to create the above cleavage site mutations (Hall and Palmenberg, 1996a). For 3D$^{pol}$ mutation R$_{16}$D, amplicons resulting from primer pairs 573 (CGT ACC Aga taa aAC AGC ACT ACG CCC CAC, SEQ. ID. NO. 2) plus 95 (CCC AGT GGA AAC CGG G, SEQ. ID. NO. 3), and 575 (GTG CTG Ttt tat cTG GTA CGT GAA TAC GG, SEQ. ID. NO.4) plus 576 (CTA CGA CAT CTG TTC TGC GCA TTC C, SEQ. ID. NO. 5) were combined, then reamplified with primer pair 95 plus 576. For 3D$^{pol}$ mutation K$_{17}$E, the primer pairs were 572 (CGT ACC Acg tga aAC AGC ACT ACG CCC CAC, SEQ. ID. NO. 6) plus 95, and 574 (A GTG CTG Ttt cac gTG GTA CGT GAA TAC Gg, SEQ. ID. NO. 7) plus 576. The resultant fragments were digested with Bgl I and Xma I, then ligated into similarly digested pEC$_4$ or pE-luc plasmids to create full-length mutated viral genomes (pEC$_4$-R$_{16}$D and pEC$_4$-K$_{17}$E), or mutated replicons (pE-luc-R$_{16}$D and pE-luc-K$_{17}$E). For 2B/2C cleavage site mutation (QS-QY), the primer pairs were 375 (CAA CAA CAA tat CCC TTG AAA, SEQ. ID. NO. 8) plus 377 (AAC TAC CCG TCA ATG GAC TCT, SEQ. ID. NO. 9), and 376 (TTT CAA GGG ata TTG TTG TTG, SEQ. ID. NO. 10) plus 378 (TTG ATA AAG ATT TCC CTT GCC, SEQ. ID. NO. 11), respectively. These two fragments were mixed then amplified by PCR using primers 377 and 378. The amplicon was digested with Sac I and Sac II, then ligated into similarly digested pEC$_4$ cDNA.

Antibodies

Murine monoclonal antibodies (mAbs) raised against recombinant Mengovirus protein 3D$^{pol}$ (8D10) and structural precursor 1CD were generously supplied by Drs. H. Duque, V. Frolov and O. Frolova (Hall and Palmenberg, 1996b; Lee et al., 1995). Murine monoclonals raised against Mengovirus (or EMCV) proteins 2B, 2C, 3A, 3AB, 3B$^{VPg}$, and 3C$^{pro}$ are described herein. Antibodies (mAb) reactive with HRV-16 protein 3C$^{pro}$ have also been described herein. Rabbit polyclonal antibodies to proteins, B23 (nucleophosmin) and C23 (nucleolin), and actin were purchased (Santa-Cruz Biotechnology, Inc.). Anti-mouse, anti-goat, and anti-rabbit secondary antibodies, conjugated with fluorescein-5-isothiocyanate (FITC) or tetramethylrhodamine-5- (and 6-) isothiocyanate (TRITC) were purchased (Sigma Inc). Western assays used HeLa cell extracts harvested at appropriate times post infection (PI). The cells were washed with phosphate-buffered saline (PBS), lysed by freeze-thaw (3×), and the clarified supernatants were fractionated by SDS-PAGE, then blotted onto polyvinylidene fluoride membranes (Immobilon-P, Millipore) as described (Duque and Palmenberg, 2001). Bands with positive reactions against the appropriate antibodies (typically, 1:2,000 dilution of ascites), were visualized by chemiluminescence (ECL kit, Amersham Pharmacia Biotech, Inc.), after secondary reactions with appropriate anti-mouse, anti-rabbit, or anti-goat antibodies, conjugated with horseradish peroxidase (1:2,000 dilution, Sigma Inc.).

Labeling of Nascent RNA

In situ RNA synthesis was visualized in cells as described previously (Ko et al., 2000). Briefly, the transfected (or infected) HeLa cells were cultured on cover slips, then washed consecutively with PBS (pH 7.4, 2×), with permeabilization buffer (20 mM Tris-HCl, pH 7.4, 5 mM MgCl$_2$, 0.5 mM EGTA, 0.5 mM PMSF), then with the same buffer containing triton X-100 (0.05%), before pulse-labeling was initiated by immersing the slips in reaction buffer (50 mM Tris-HCl, pH 7.4, 100 mM KCl, 5 mM MgCl$_2$, 2 mM MnCl$_2$, 0.5 mM EGTA, 25 U/ml RNasin, 0.5 mM of ATP, CTP, GTP, and 0.2 mM flourescein-12-UTP, Sigma Inc.). After incubation (30 min at 37° C.), the cells were washed (2×, PBS, 25 U/ml RNasin), then fixed (PBS, 10% formaldehyde, 25 U/ml RNasin, 20° C., 20 min). Subsequent cell permeabilization, blocking, antibody reactions, and visualization by confocal immunofluorescence microscopy were as described below.

Immunofluorescence Microscopy

HeLa monolayers were grown on cover slips to 50-70% confluence then infected (m.o.i. of 10), or transfected (1.5 μg RNA per 5×10⁶ cells) (Duque and Palmenberg, 2001) as required. At appropriate intervals (37° C. under 5% $CO_2$-air), the cells were rinsed with PBS, fixed with formaldehyde, permeabilized by 0.3% Triton X-100, then incubated (1 hr, 20° C.) with the desired primary antibody (1:2,000 dilution in blocking solution), as described (Amineva et al., 2003). After reaction with a corresponding secondary antibody, the slips were mounted (Vectashield mounting medium, Vectorlab), and label location was visualized by laser-scanning confocal microscopy. Image capture used MCR 1024 LaserSharp software (Bio-Rad, Inc.). For double-label experiments, primary antibodies raised in different species (e.g., mouse and rabbit) were selected, and the samples were developed with appropriate, corresponding secondary antibodies (1:100 dilution) conjugated with FITC or TRITC. A fluorescent-tagged wheat germ agglutinin (WGA, Molecular Probes, Inc.) was used to highlight and identify Golgi and nuclear membrane locations. SYTOX stain (Molecular Probe Inc.) was used to localize dsDNA within cells. Photography used an 488 nM filter for detection FITC and an 647 nM filter for detection of TRITC or SYTOX.

RNA and Microarray Analyses

Confluent HeLa cell monolayers (3×10⁶ cells per 60 mm plate) were infected (m.o.i. of 10) with $vEC_9$, $vE-2A_{A58}$ or HRV-16, then incubated (37° C., under 5% $CO_2$-air) for 2 or 5 hrs. The total RNA (3 plates per sample) was isolated and purified using RNasy Total RNA Isolation Kits (Qiagen Inc). Quantitative northern assays (dot blots) used DNA primers specific for 5S rRNA (M51545, GCAACCCTACAGAAC-CCGGTG, SEQ. ID. NO. 12), 18S rRNA (M10098, GCCG-GTCCAAGAATTTCACCTCTA, SEQ. ID. NO. 13), 28S rRNA (M27830, GTCGAGGGCTGACTTTCAATA, SEQ. ID. NO. 14), or for the mRNA of glyceraldehyde-3-phosphate dehydrogenase (M33197, CCACGATACCAAAGT-TGTCATGGAT, SEQ. ID. NO. 15), as described previously (Sambrook et al., 1989). The Superscript Choice System (Gibco BRL Life Technologies) was used to convert a sample of each cellular RNA fraction (10 μg) into cDNA using SSII reverse transcriptase with an oligo(dT)-T7 promoter primer. The second strand of cDNA was synthesized in reactions (self-primed) with DNA polymerase I, RNase H, and DNA ligase according to the manufacturer's directions. Biotin-labeled RNA probes were generated from these DNAs using RNA Transcript Labeling Kits (Affymetrix Inc.) with T7 RNA polymerase and biotin-NTPs. After fragmentation by boiling, the labeled-RNAs were hybridized to microarrays (Affymetrix, H-95A) that were developed, scanned and analyzed with GeneChip software (Affymetrix), after staining with R-phycoerythrin streptavidin conjugate (Molecular Probe).

Results and Discussion

Proteins $3B^{VPg}$, $3C^{pro}$ and $3D^{pol}$ Localize to Nucleoli

In accordance with the methods of the invention, applicants have cloned 7 Mengoviral and EMCV proteins into bacterial expression systems and used the material to immunize mice for the isolation of monoclonal antibodies (mAbs). Antibodies (mAbs) against EMCV $3B^{VPg}$ were raised to a synthetic protein. Given the 93.6% average amino acid identity between polyproteins, it was not surprising to find most mAbs in the panel reacted equally well against EMCV (i.e. $vEC_9$) or Mengovirus (i.e. vMwt) proteins, and indeed this was a selection criterion for any mAb used in subsequent cell labeling or Western analyses as described herein. The initial rational for development of these mAbs was to help follow polyprotein precursor fates through the labyrinth of the $3C^{pro}$ processing events in cell-free extracts. Eventually, however, it also seemed like a good idea to pursue some of the precursors temporally and physically within infected cells by immunofluorescence microscopy, using the mAbs as labels. The first images were astounding. Without question, mAbs against four mature viral proteins, 2A, $3B^{VPg}$, $3C^{pro}$ and $3D^{pol}$, lit up nuclear as well as cytoplasmic loci during the entire time course of Mengovirus or EMCV infection (e.g., FIG. 10A). The consequences and mechanism of protein 2A nuclear localization, and the role of this activity in the shutoff of cap-dependent host mRNA translation is discussed hereinabove. Of interest here are the three other viral proteins found in nuclei, and their unanticipated novel role(s) in the viral lifecycle.

Figure 10:
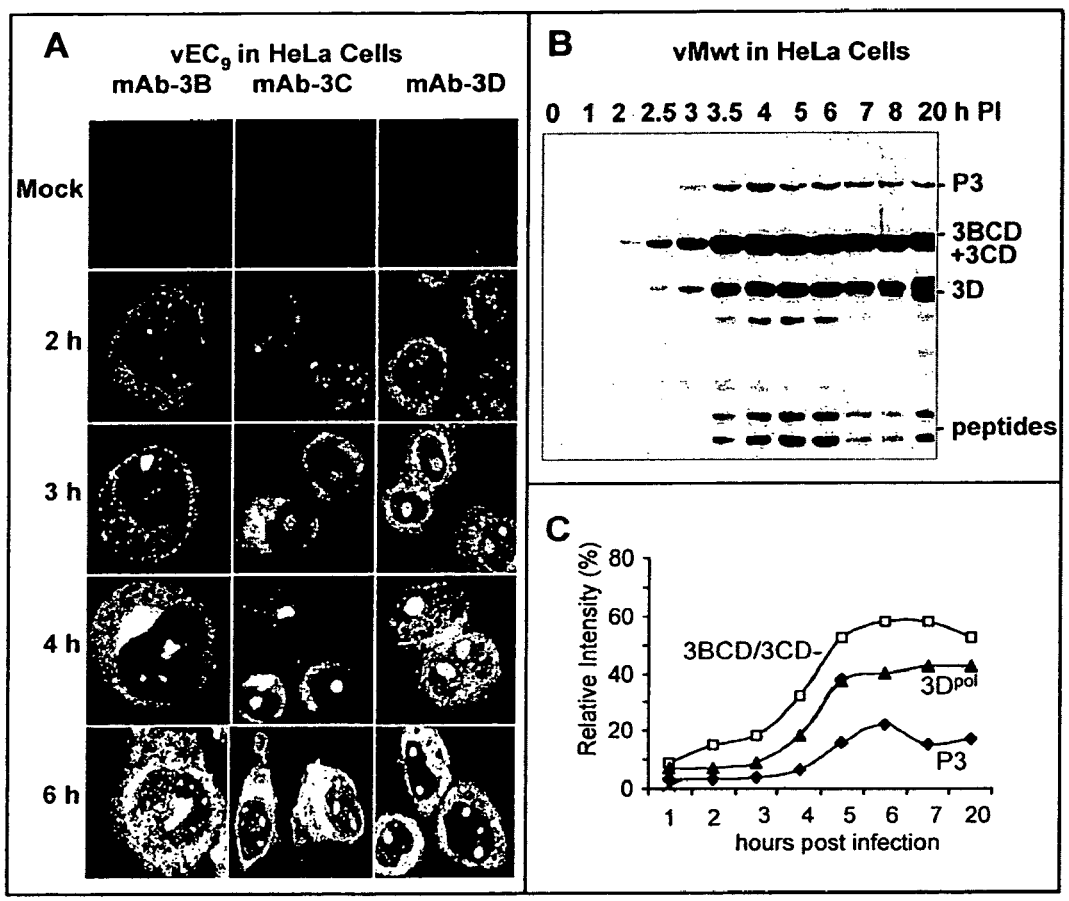
FIGS. 10A-C show localization of P3-region precursor(s) (i.e., 3BCD) in nuclei of infected cells. Panel A shows confocal microscopy images of $vEC_9$-infected HeLa cells (m.o.i. of 10) harvested at the indicated times (2, 3, 4, 6 h) PI, then stained with mAb-3B, mAb-3C, or mAb-3D, and then with FITC-conjugated, anti-mouse antibodies. All images used identical filter settings. Panel B shows HeLa cells infected with vMwt (m.o.i. of 10) were harvested at the indicated times PI, fractionated by SDS-PAGE, then probed in Western analyses with mAb-3D. Panel C shows a densitometry plot. Gel lanes from the Western blot (B) were scanned by densitometry, and the relative band intensity due to each protein was normalized for each lane and plotted.
Figure 11:
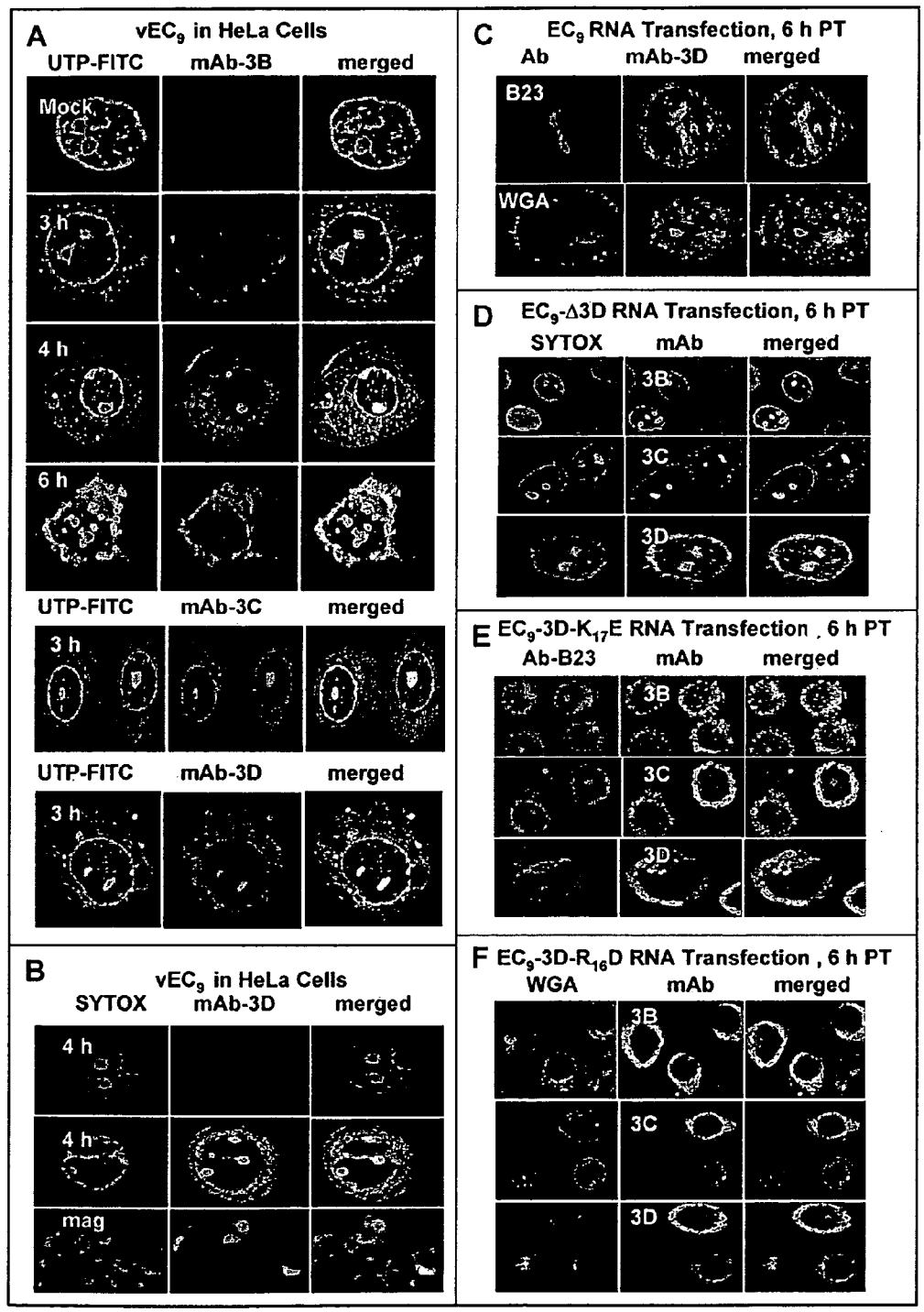
FIGS. 11A-F show $3D^{pol}$ contains a nuclear localization signal and that the P-3 region is involved in nuclear transport. Panel A shows results from HeLa cells that were infected with $vEC_9$. After 3, 4 or 6 hrs, the cells were pulse-labeled with FITC-conjugated UTP, and 30 min later they were fixed and stained with mAb-3B, mAb-3C or mAb-3D. The secondary anti-mouse antibody was conjugated to TRITC. Panel B provides results from chromatin visualization experiments. Samples were similar to A (mAb-3D) except that SYTOX stain was used to visualize chromatin. The bottom triptych is at higher magnification. Panels C-F provides results from transfection experiments. Genome-length RNA transcripts from $pEC_9$ (C), $pEC_9$-$\Delta3D$ (D), $pEC_9$-3D-$K_{17}E$ (E) or $pEC_9$-3D-$R_{16}D$ (F) were transfected into HeLa cells as described in the Methods below. At 6 hrs post transfection (PT), the cells were fixed and stained with WGA (Golgi marker) or Ab-B23 (goat), and with mAb-3B, mAb-3C, or mAb-3D, as indicated. The secondary anti-mouse antibody was conjugated to FITC. The secondary anti-goat antibody was conjugated to TRITC.

From the earliest times after EMCV infection of HeLa cells (or L-929 and BHK-21 cells, not shown), mAbs against $3B^{VPg}$, $3C^{pro}$ and $3D^{pol}$ formed bright, punctate spots in nuclei (FIG. 10A), in addition to broadly diffuse labeling of the Golgi and ER where viral translation and RNA synthesis occur (Kuhn and Wimmer, 1987). Between 2 and 3 hr PI, the nuclear signals, especially when detected with mAb-3C and mAb-3D, became increasingly strong and coalesced unmistakably within nucleoli. EMCV or Mengovirus infection at this m.o.i. (10 PFU/cell) usually kills cells within 6-8 hrs PI, but even at these latest time points, the nucleoli continued to glow brightly against a background of ever increasing cytoplasmic signals. Additional examples of nucleolar localization by these proteins are shown in FIG. 11A. In this experiment, the immunogenic signal(s) (red) were superimposed on UTP labels (green) denoting sites of ongoing active RNA synthesis. Again, the colocalization of the brightest mAb and RNA signals within the nuclei were characteristic of nucleolar targeting by these proteins. All images in this figure were captured with the same filter settings and therefore reflect the progressive accumulation of immunogenic material throughout the infection.

Precursor Identification

Cell labeling by mAbs could not distinguish whether the mature proteins or their precursors (e.g., 3CD, 3BCD, or 3BC) were responsible for nuclear and nucleolar targeting. Nor could they distinguish turnover between the nuclear and cytoplasmic protein pools as the infection progressed, and indeed, kinetic labeling of this sort is not trivial. Rather, as an initial approximation of the process, we instead tried to characterize the repertoire of precursors and mature proteins that could have given rise to the various signals. Infected HeLa cells were lysed, fractionated by SDS-PAGE, then probed in Western assays for reactive bands using each of the P2 or P3 protein mAbs in turn. FIG. 10B shows a typical result for mAb-3D. The same data are presented graphically in FIG. 10C. The earliest detectable $3D^{pol}$-containing proteins included precursors 3BCD (76 kD) and 3CD (74 kD), which run close together on these gels, but can be distinguished by reactivity to mAb-3B. Uncleaved P3, mature $3D^{pol}$, and a variety of smaller (degraded?) 3D-immunoreactive peptides were evident in increasing concentrations from 3-5 hrs PI, the timeframe of maximum viral RNA synthesis and viral protein translation (Jen et al., 1978).

Western assays with mAbs against $3B^{VPg}$ and $3C^{pro}$ using fresh gel blots or membranes that were stripped and reprobed, gave similar results, in that viral precursors dominated the immunogenic signals from infected cells, especially at the earliest times PI (FIG. 11A) (Corsi and Schekman, 1996).

Figure 12:
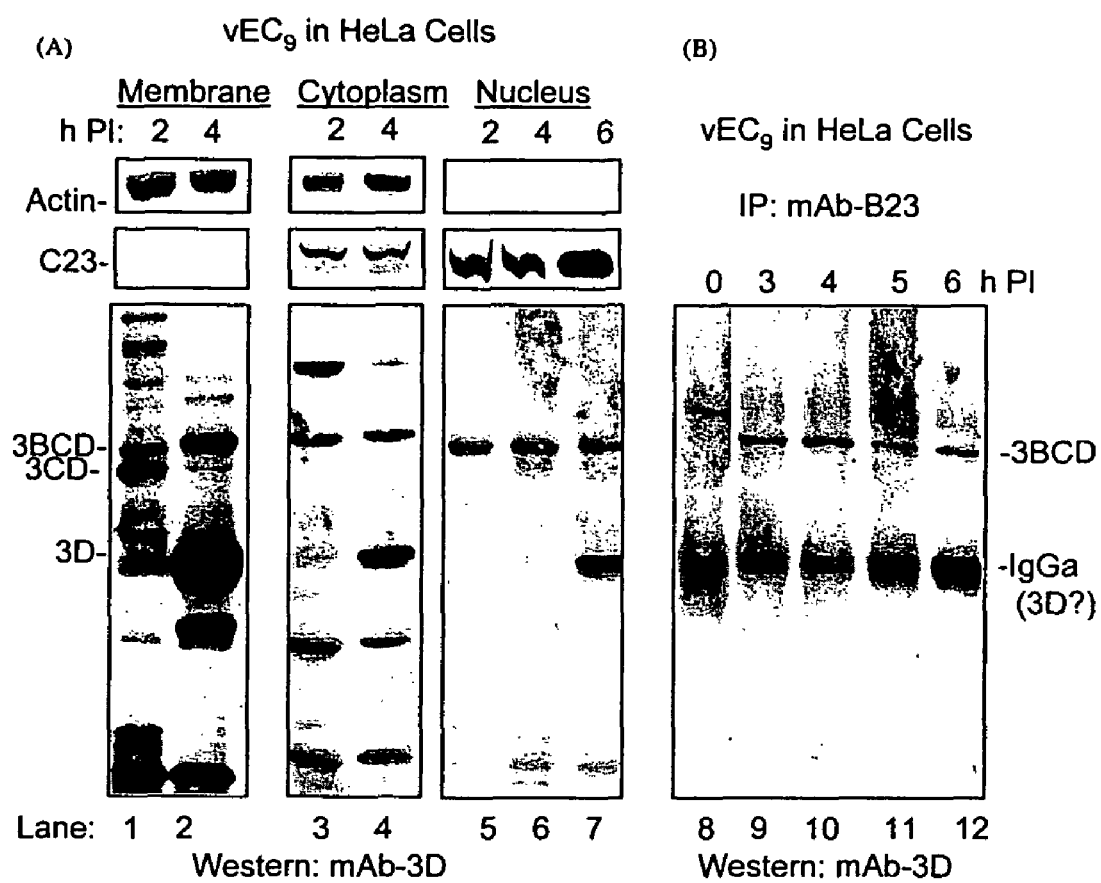
FIGS. 12A-B show the distribution of viral precursor proteins in infected cells. Panel A shows HeLa cells infected with $vEC_9$ were harvested at 2, 4 or 6 hr PI, then fractionated into membrane, cytoplasm or nuclear fractions as described in the Methods below. Samples were fractionated by SDS-PAGE, then probed in Western assays with mAb-3D. Subsequently, the membranes were stripped and reprobed (inserts) using antibodies against actin (cytoplasmic marker) and C23 (nuclear marker). Panel B shows that infected HeLa cells were harvested at the indicated times PI, and nuclear extracts (as in A) were subject to immunoprecipitation with Ab-B23. The reactive material was fractionated by SDS-PAGE, then probed by Western analyses using mAb-3D.

Applicants have found that mAbs proved quite adept at detecting and identifying transient precursors such as 2C3A, 2C3AB, 3BC, 3BCD and 3ABC, and at monitoring their conversion into mature forms, like 3AB, 3CD, 3C$^{pro}$ and 3D$^{pol}$ as described herein. To determine where these protein pools were distributed, infected cells were fractionated in the presence of a mild detergent (NP40) before SDS PAGE and sequential probing with the mAbs (FIG. 12A). In this case, actin and nucleolin (C23) antibodies were included in the experiments (top panels) to verify enrichment by the fractionation protocol. From 2-4 hr PI, cellular, cytoplasmic and membrane samples, confirmed the expected shift from P3-region precursors to a major 3D$^{pol}$ band as the infection progressed and viral RNA synthesis accelerated. Remarkably however, a single P3-region precursor dominated the nuclear fractions at every time point. Protein 3BCD, identified by co-reactions with mAbs against 3B$^{VPg}$, 3C$^{pro}$ and 3D$^{pol}$ was always the strongest, and usually only, P3-derived band in these samples. Sometimes bands of 3CD or 3D$^{pol}$ also became evident as the infection progressed (FIG. 12A, lanes 6 and 7), but clearly, 3BCD was main source of all three P3-region mAb signals in the nuclei of infected cells. The precursor was also present in the cytoplasmic and membrane fractions from the earliest times of infection (2 hr PI), along with many other viral proteins derived from P2 and P3 region cleavage permutations. It was only the nuclei that showed selective enhancement of 3BCD.

Figure 13:
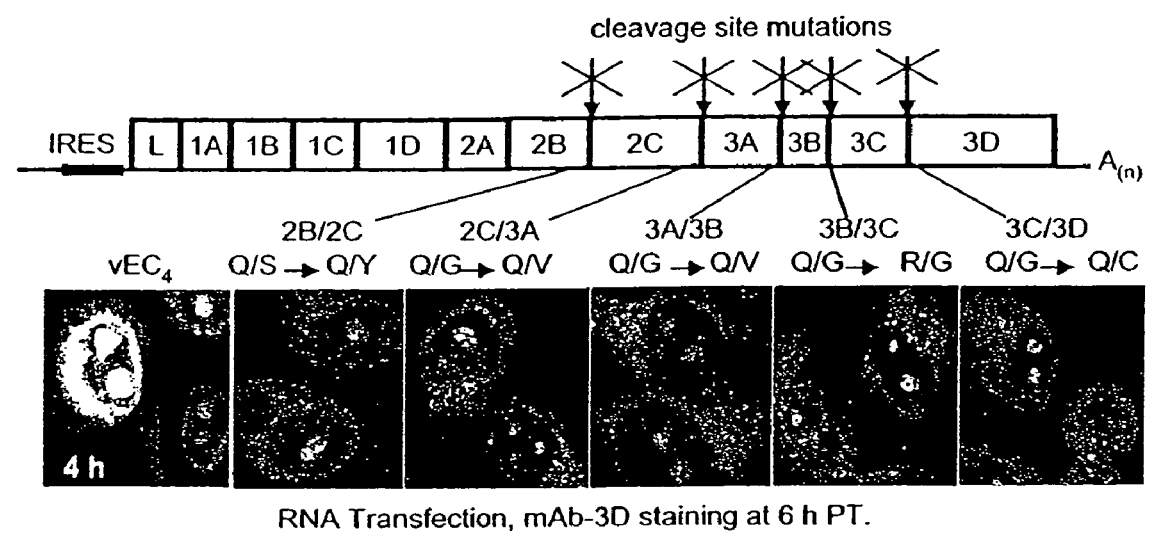

To test the effects of cleavage site mutations on the nuclear localization of 3B$^{VPg}$, 3C$^{pro}$ and 3D$^{pol}$ mAb signals, point mutations were engineered into the codons for each of five processing site in the P2 and P3 regions of vEC$_4$, using alterations known to abrogate 3C$^{pro}$ activity (Parks et al., 1989). The 3A/3B, 3B/3C and 3C/3D mutations are lethal to infectivity (Hall and Palmenberg, 1996a). The 2B/2C and 2C/3A mutations allow weak viral growth, but only of revertant progeny, and all five cleavage site mutations are known to impede viral RNA synthesis (Hall and Palmenberg, 1996a; Parks et al., 1989). None, however, was able to prevent nuclear labeling by 3B$^{VPg}$, 3C$^{pro}$ and 3D$^{pol}$ mAbs, after transfection with genome-length RNA transcripts (FIG. 13). The consistent spectrum of nuclear labeling regardless of the location of blocked cleavage sites is exactly that expected if a large P3-region precursor(s) (i.e. 3BCD), rather than the cleaved, mature viral proteins, were responsible for nuclear localization and mAb reactivity.

3D$^{pol}$ NLS Identification

As reported for the EMCV 2A nuclear signals, mAbs against 3B$^{VPg}$, 3C$^{pro}$ and 3D$^{pol}$ always co-localized with B23 (nucleophosmin) and C23, the ribosomal chaperone proteins (Hingorani et al., 2000; Szebeni et al., 1995). FIG. 11C (top panel) gives an example this unity, using mAb-3D. The 3D$^{pol}$ and B23 signals show extensive overlap in the nucleoli. When vEC$_9$-infected nuclear extracts were immunoprecipitated with Ab-B23, a strong 3BCD band was clearly evident, indicating a direct reaction, or co-interaction within a common complex, probably within nucleoli (FIG. 12B). Although the requirements for protein accumulation in nucleoli are not very well defined, binding to nucleolar proteins or nucleolar RNAs (rRNA or snRNA) is usually a common theme (Valdez et al., 1994; Li et al., 1996), and the close association between B23 and 2A as described herein or 3BCD (FIG. 11C and FIG. 12B), may point to a common mechanism. During HIV infections, for example, B23 interacts with Rev, Rex, and Tat viral proteins and helps direct them into nucleoli (Szebeni et al., 1997; Stauber and Pavlakis, 1998; Hiscox, 2002; Adachi et al., 1993). Within the cardiovirus 2A protein, a short, conserved segment has been identified in the COOH third of the protein that resembles the [KR] [KR]X$_{10[}$3 of 5: KRHW] motif, defining about 50% of known nuclear proteins in eukaryotic cells (Michael, 2000). Moreover, a subset of peptide fragment (KRvRP for EMCV-R) is an exact match for the nuclear targeting pattern, common to many yeast ribosomal proteins bound by B23 (YRP, reviewed in (Stuger et al., 2000). No cardiovirus protein, including 2A, 3B$^{VPg}$, 3C$^{pro}$ or 3D$^{pol}$ has been shown to contain a canonical nuclear localization signal that could otherwise target it, or related precursors, to the more obvious importin-α or importin-β trafficking pathways (Lischka et al., 2003; Dingwall and Laskey, 1991). Such signals do exist in the NH$_2$-terminal third of enterovirus and rhinovirus 3D$^{pol}$ as described herein, but those motifs are not completely reiterated in the cardioviruses, nor in other members of the family (Palmenberg and Sgro, 2001). Instead, much closer to the NH$_2$-terminus of 3D$^{pol}$ of every known picornavirus, is again a YRP motif (PRKtalRP in EMCV-R) of the type bound by B23 (FIG. 14).

Figure 14:
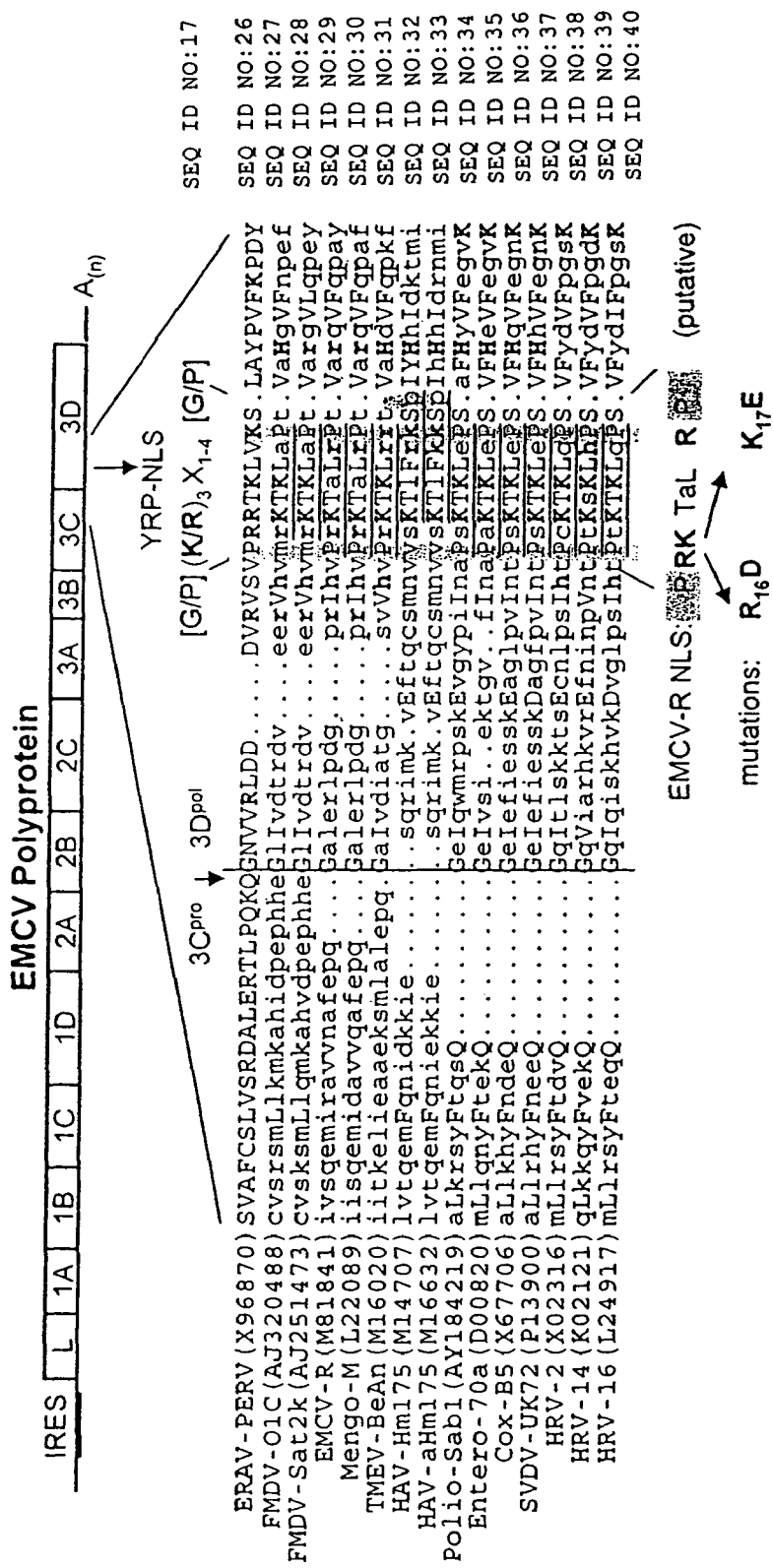
FIG. 14 shows a representative alignment (Palmenberg and Sgro, 2001) of picornavirus sequences near the 3C/3D protein junction. The consensus nuclear localization sequence found in several yeast ribosomal proteins or YRP (Stuger et al., 2000) is indicated, as is the corresponding, putative NLS in EMCV-R (i.e. vEC$_9$). Locations of the point mutations converting two of the YRP motif codons, $R_{16}D$ and $K_{17}E$ mutations are highlighted.
Figure 15:
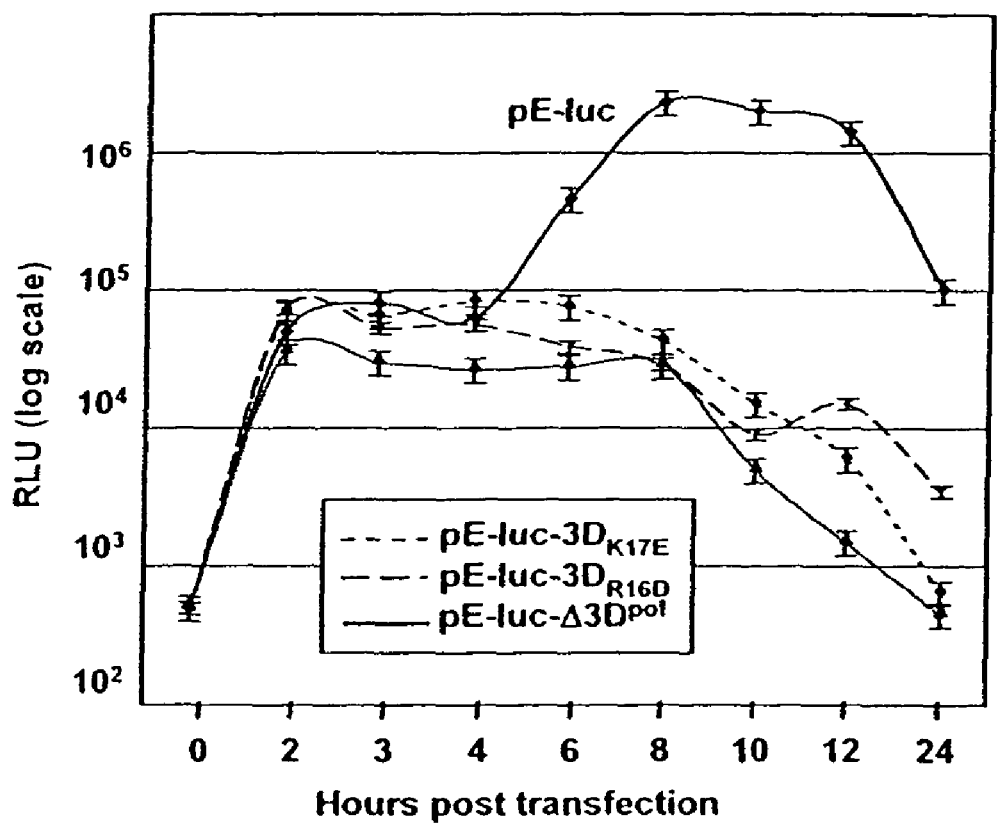
FIG. 15 shows that the replicon transcripts carrying the 3D$^{pol}$ of the family Picornaviridae. Examples are: EMCV-R (Rueckert) strain, Mengovirus, Mus Elberfeld virus, Columbia-SK virus.

To explore whether this region could be involved in nuclear or nucleolar transport of 3BCD, point mutations converting two of the YRP motif codons (R$_{16}$D and K$_{17}$E) were engineered into the 3D$^{pol}$ region of recombinant vEC$_9$ (FIG. 14). Both proved deadly to virus growth, and only a few, small virus plaque were isolated from cells transfected with mutant transcripts (not shown). Replicons transcripts carrying the same mutations were defective in the synthesis of viral RNA (FIG. 15). Although some luciferase was produced (0-3 hr post-transfection) in transfected cells, the rates paralleled that of a replication incompetent sequence (pE-luc-Δ3D), missing 185 amino acids of 3D$^{pol}$. From the resolved poliovirus polymerase structure (Hansen et al., 1997) we anticipated that EMCV mutations and their encompassing YRP-NLS motif could be positioned near the catalytic GDD portion of the protein. Therefore, a replication-defective, lethal phenotype was not unexpected. In addition, the premise that this region could also be involved in nuclear transport, proved true as well. When transfected into cells, the 3B$^{VPg}$, 3C$^{pro}$ and 3D$^{pol}$ immunogenic signals from EC$_9$-3D-R$_{16}$D and EC$_9$-3D-K$_{17}$E were only found in the cytoplasm (FIGS. 11E and 11F), even at 24 hrs post-transfection. None of the P3-region mAb signals (proteins) co-localized with nucleolar B23. In contrast, replication incompetent viral proteins, synthesized from pEC$_9$-Δ3D transcripts (FIG. 11D), which maintained an intact YRP motif, distributed into nuclei just like the wild-type sequences, despite the lack of viral RNA synthesis (FIG. 11C). That all three mAb signals (3B$^{VPg}$, 3C$^{pro}$ and 3D$^{pol}$) appeared or disappeared as a unit with these point mutations, is in accord with our model of a single precursor (3BCD) assuming responsibility for collective nuclear transport, and moreover, that the mutated residues near the end of 3D$^{pol}$ are an essential component of that transport mechanism.

rRNA Transcription

Rhinovirus and enterovirus infections cause rapid shutoff of pol-I (Rubinstein et al., 1992), pol-II (Yalamanchili et al., 1997a; Yalamanchili et al., 1997c) and pol-III transcription (Clark et al., 1991). Pol-II shutoff by Mengovirus infection was first documented more than 40 years ago in experiments that led to the initial characterization of this important cellular enzyme (Baltimore and Franklin, 1962), but the effects of cardioviruses on pol-I and pol-III are less well understood. Cells pulse-labeled with FITC-UTP showed a very different pattern following vEC$_9$ infection (FIG. 11A) than HRV-16 infection as described herein. The nuclei did not become swollen, diffuse or leaky to proteins (e.g., see FIG. 11A). Rather, EMCV-infected cells, or cells transfected with EMCV RNAs, continued to incorporate UTP into brightly glowing, clearly defined nucleoli until the time of cell death or lysis. Consistent with pol-II shutoff, but not pol-I or pol-III, a SYTOX chromatin stain showed massive DNA rearrangements in all areas of the nuclei, except the nucleoli, which were left intact throughout the infection (FIG. 11B). In parallel, B23 (FIG. 11C) and C23 (not shown) condensed within the nucleoli. These proteins are key components in the organization and transcriptional regulation of ribosomal DNA, and their continued or even enhanced presence is another definitive indication of nucleolar integrity and ongoing rRNA synthesis (Okuwaki et al., 2001; Srivastava and Pollard, 1999).

Direct attempts to quantitate the continued pol-I and pol-III synthesis by these nucleoli were complicated by several factors. The first was the surprising observation that the total RNA in EMCV (or Mengovirus)-infected cells, as measured by $OD_{260}$ on a per cell basis, was 25-50% lower than for mock-infected or HRV-16 infected cells (Table 1). The decrease in RNA content was evident as early as 2 hr PI (6% relative to mock), even before the onset of vRNA synthesis. Larger losses were measured by 5 hr PI (22% relative to mock). The shortfall in cellular RNA could be documented by a variety of techniques (not shown), and was not attributed to viral-induced cell lysis, which does not occur until 7-8 hrs PI. Viral mutants with 2A gene deletions (e.g., vE-2A$_{\Delta 58}$), are defective in nucleolar localization and defective in host pro-tein translational shutoff (Svitkin et al., 1998), but found to have even lower RNA contents (63.5% relative to mock infected cells). Another complication with rRNA measurements was the knowledge that the cellular mRNA pool changed dramatically over infection, as did the vRNA pool. Polyadenylated host mRNA usually represents about 1-3% of total RNA in an uninfected cell (Darnell et al., 1990), but after pol-II shutoff by infection, the turnover rate for existing mRNA was unknown. Therefore, OD alone could not be used, even as a rough estimate, of rRNA content.

Measurement of the relative cellular mRNA content was eventually resolved with microarray analyses (FIG. 16, below), but the 5S, 18S and 23S rRNA concentrations, required quantitative slot-blot testing, using labeled cDNA probes, specific for each sequence (Table 1). Again, whether tabulated on a per cell basis or a per ng basis, it was clear the cardiovirus-infected cell samples were missing a great deal of rRNA. Cells infected with vEC$_9$ had 24-27% less of 5S, 18S and 23S rRNA than control samples or HRV-16 infected samples, and there was at least a 39-45% relative loss of all three rRNAs for vE-2A$_{\Delta 58}$. We conclude that despite the continued UTP incorporation in cardiovirus-infected nucleoli, this synthesis did not keep pace with an accelerated rate of ribosome turnover.

TABLE 1

Ribosomal RNA Isolation

|  | mock HeLa | VEC$_9$ 2 hr PI | vEC$_9$ 5 hr PI | vE-2A$_{\Delta 58}$ 5 hr PI | HRV-16 5 hr PI |
|---|---|---|---|---|---|
| Isolated RNA[a] | | | | | |
| Total RNA | 20 µg | 18.8 µg | 15.6 µg | 12.7 µg | 21.7 µg |
| relative to mock | 100% | 94% | 78% | 63.6% | 106% |
| Slot Blot assay[b] | | | | | |
| 5S rRNA | 100% | 83% | 97% | 96% | 105% |
| 18S rRNA | 100% | 87% | 95% | 96% | 101% |
| 23S rRNA | 100% | 88% | 94% | 86% | 95% |
| Slot Blot assay[c] | | | | | |
| 5S rRNA per cell | 100% | 78% | 76% | 61% | 111% |
| 18S rRNA per cell | 100% | 82% | 74% | 61% | 107% |
| 23S rRNA per cell | 100% | 82% | 73% | 55% | 101% |

[a] HeLa cells (15 × 10$^6$) were infected as described in Methods. At 2 or 5 hr PI, the total RNA per sample was isolated, purified then quantitated using a scanning spectrophotometer.
[b] The samples in A were brought to equivalent concentrations (OD$_{260}$), diluted serially, then probed in quantitative Northern assays for reactivity with rRNA-specific radiolabeled probes as described in the Methods herein. The data were captured by phosphoimaging and digitized. The intercept value for the linear regression analysis of each dilution curve is represented as percent of the mock-infected value for that rRNA.
[c] The data in B were corrected for relative concentration in the original, total RNA pools.

mRNA Transcription

Figure 16:
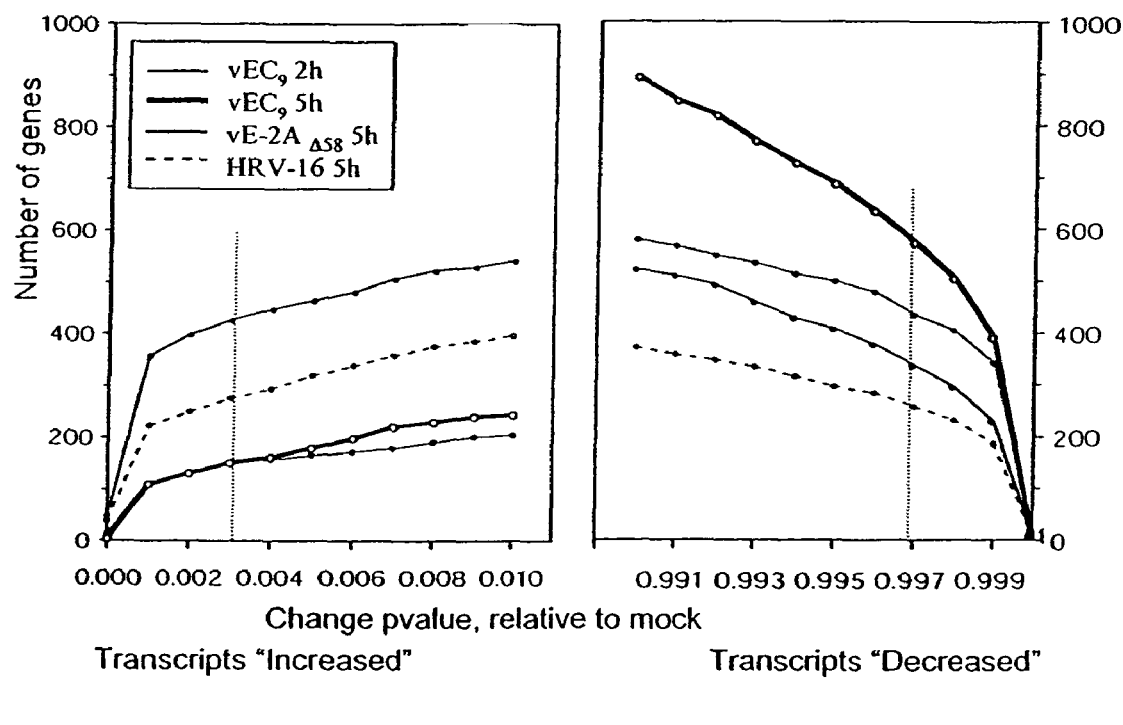

New ribosome synthesis requires proteins in addition to rRNA. It was therefore of interest to learn whether the ribosomal protein genes could have been selectively spared from cardiovirus-induced shutoff of pol-II, or alternatively, whether these proteins were recycled from ribosome turnover. Accordingly, HeLa cells were infected with vEC$_9$, HRV-16, or vE-2A$_{\Delta 58}$. After 2 hrs to 5 hrs PI, the total RNA was isolated from these cells. The poly(A)-containing RNA in equivalent samples (10 µg of total RNA) was copied into cDNA with reverse transcriptase, then probed for transcript content using microarrays (Affymetrix, Hu-95A). Each array used 20 match/mismatch probe pairs to assess whether each of 10,000 human gene transcripts was detected (present) or not detected (absent), and to assign a measure of relative abundance to each transcript according to statistical thresholds (Snedecor et ai., 1980). RNA from mock-infected cells (10 µg, 5 hr PI) was included as a baseline, and when the array data were compared, this was the standard against which statistical calls of "increase", "decrease", or "no change", were assigned to the infected samples (FIG. 16 and Table 2). Confidence in the comparative calls were expressed as a "change p-value" statistic, according to Wilcoxon's signed-rank test (Snedecore et al, 1980). As this value approached 1.0 for any transcript, there was increased confidence of a diminished concentration (turn off) in sample B relative to sample A. Conversely, values approaching 0.0, indicated a significant turn on, or transcript increase in B relative to A. Intermediate values (i.e. 0.005-0.995) designated transcripts that were unchanged between the samples or where the changes could not be called with certainty.

TABLE 2

Altered HeLa Cell Gene Expression During EMCV Infection

| [a] Transcripts activated by 5 hr PI with vEC$_9$ | Receptor proteins | FPRL1 (M84562), transmembrane protein (U19878), frizzled 5 (U43318), IgG FcRIIa (M31932), Interleukin-1 (AJ005835), adenosine receptor (L77730) |
|---|---|---|
| | Oncogens | proto-oncogene (X75042), o-syn (M14333) |
| | Transcriptional regulators | zinc finger (U09368), Stat5b (U48730) |
| | Apoptotic regulators | BAX-delta (U19599) |
| | Growth factors | growth arrest homeobox protein (U68727), CJR11 (U66468), FGF8 (U47011), CGR19 (U66469), nerve growth factor (M57399) |
| | Immune response proteins | PKR (U50648), immunoglobulin A (S71043), ribosomal proteins L-23 (X55954), L38 (Z26876) and S17 (M13932), ribosomal S6 kinase (M60724) |

TABLE 2-continued

Altered HeLa Cell Gene Expression During EMCV Infection

| | Enzymes | tyrosine phosphatase (M25393), N-acetyltransferase (D90042) P1-cre recombinase (X03453), TAP Synthetase (J04423), apolipoprotein (X02162) |
|---|---|---|
| [b] Transcripts inactivated by 5 hr PI with vEC$_9$ | Transcriptional regulators | CREB-binding protein (U47741), CACCC box-binding protein (L04282), histone acetyltransferase, (AF030424), GATA2 (M68891) Gamma inducible interferon IP-30 (J03909). Additionally, all transcripts in "c" below. |
| [c] Transcripts activated by 5 hr PI with vE-2A$_{\Delta 58}$ | Transcriptional regulators | TFII transcription factor (AF015553), transport stimulator (Af020761), basic helix-loop-helix DNA-binding protein (S73885), TATA binding protein-associated phosphoprotein (M97388), TATA binding protein (U72355), CREB-binding protein (U47741), RNA polymerase II subunit (U37689), RNA polymerase II elongation factor (U88629), histone H2B (AJ223353) |

Microarray analyses with vEC$_9$ ([a] and [b]) and vE-2A$_{\Delta 58}$ ([c]) infected HeLa cell RNA samples are described in Methods. Select examples of "increased" or activated transcripts (p-change values of <0.0025 relative to control samples) and "decreased" or inactivated transcripts (p-change values of >0.9985) are listed, along with relevant GenBank accession numbers.

Figure 7:
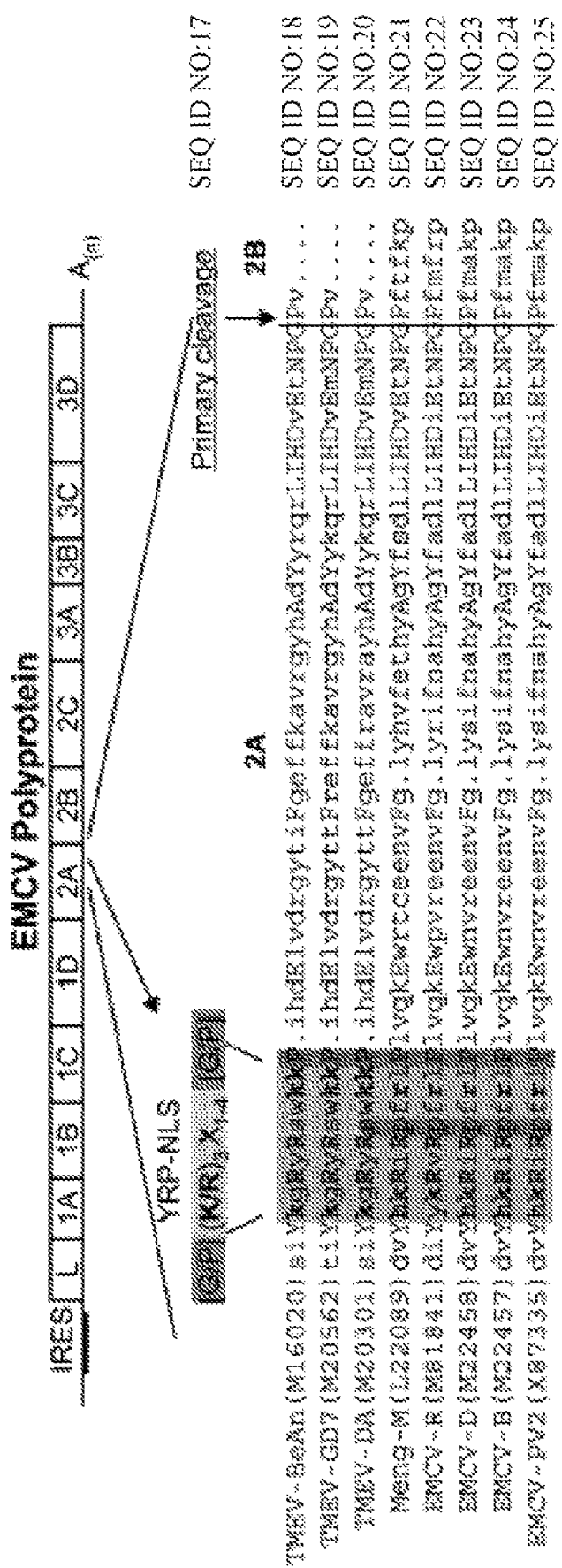
FIG. 7 shows a representative alignment (Palmenberg and Sgro, 2001) of cardiovirus sequences near the COOH termini of the viral 2A proteins is shown. GenBank accession numbers for representative strains of the Theiloviruses (tme) and Encephalomyocarditis viruses (emc and mengo) are given. Co-translational primary cleavage of each viral polyprotein occurs between the Gly-Pro (G/P) of the PCC (EMCV-R: YAGYFADLLIHDIETNPGP). The consensus nuclear localization sequence found in several yeast ribosomal proteins (Stuger et al., 2000) is indicated, and the potential virus cognates are highlighted.

FIG. 7 plots the number of transcripts observed with high-end (decreased) or low end (increased) change p-values, when compared to the control (mock) array. For example, at a cutoff of 0.997 (suggested default for GeneChip software), the arrays registered a significant decrease for 434 genes at 2 hr PI for vEC$_9$, 573 genes at 5 hr PI, 337 genes at 5 hr PI with vE-2A$_{\Delta 58}$, and 258 genes at 5 hr PI for HRV-16, compared to 5036 genes that were "present" in the uninfected cells at the beginning of the experiment. A slightly more liberal cutoff (0.991) increased all values, but especially that of vEC$_9$ which now registered a decrease of 840 genes. This means that by 5 hr PI, nearly 17% of the original HeLa cell transcripts were shut off or turned over, in an infection-dependent manner. HRV-16 was less effective at this process, as was vE-2A$_{\Delta 58}$. At the other end of the scale with a cutoff of 0.003 (Affymetrix default), only 148 (2 hr PI) and 151 (5 hr PI) gene transcripts were significantly increased by vEC$_9$ infection, compared to 258 and 337 genes for HRV-16 and vE-2A$_{\Delta 58}$, respectively. Put simply, wild-type EMCV was very adept at pol-II shutoff, in a 2A-dependent manner, and by 5 hr PI, was perhaps twice as effective as HRV-16. Comparatively few genes were induced by vEC$_9$ infection, unless again, the 2A protein was defective. Table 2 tabulates some examples of activated and inactivated genes from the data sets, with emphasis on possible regulatory factors and transcription factors. Nearly all of the ribosomal protein transcripts, the original premise for this experiment, registered "present" in the mock-infected cells, and "no change" in the infected cells. Therefore, in general the data suggest that nuclear targeting by 2A and 3BCD may be responsible for regulating cellular mRNA and rRNA transcription during infection, perhaps via a proteolytic mechanism catalyzed by the endogenous 3C$^{pro}$ sequence.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

CITED PUBLICATIONS

Agol, V. I. (1991) The 5' untranslated region of picornaviral genomes. Adv. Virus Res. 40:103-180.

Aminev, A. G., Amineva, S. P., and Palmenberg, A. C. (2003) Encephalomycarditis Viral Protein 2A Localizes to Nucleoli and Inhibits CAP-Dependent mRNA Translation. Virus Research, 95:45-57.

Aminev, A. G., Amineva, S. P., and Palmenberg, A. C. (2003). Encephalomyocarditis virus (EMCV) proteins 2A and 3BCD localize to nuclei and inhibit cellular mRNA transcription but not rRNA transcription. Virus Res., 95:59-73.

Amineva, S. P., Aminev, A. G., Palmenberg, A. C., and Gern, J. E. (2003). HRV 3C protease precursors 3CD and 3CD' localize to the nuclei of infected cells and cleave transcriptional factor OCT-1. J. Virol. submitted.

Adachi, Y., Copeland, T. D., Hatanaka, M., and Oroszlan, S. (1993). Nucleolar targeting signal of rex protein of human t-cell leukemia virus type i specifically binds to nucleolar shuttle protein b-23. J. Biol. Chem. 268, 13930-13934.

Ambros, V. and Baltimore, D. (1978). Protein is linked to the 5' end of poliovirus RNA by a phosphodiester linkage to tyrosine. J. Biol. Chem. 253, 5263-5266.

Anderson-Sillman, K., Bartal, S., and Tershak, D. R. (1984). Guanidine-resistant poliovirus mutants produce modified 37-kilodalton proteins. J. Virol. 50, 922-928.

Apriletti, J. W. and Penhoet, E. E. (1978). Cellular RNA synthesis in normal and mengovirus-infected L-929 cells. J. Biol. Chem. 253, 603-611.

Arnold, E., Luo, M., Vriend, G., Rossmann, M. G., Palmenberg, A. C., Parks, G. D., Nicklin, M. J., and Wimmer, E. (1987). Implication of the picornavirus capsid structure for polyprotein processing. Proc. Natl. Acad. Sci. U.S.A. 84, 21-25.

Baltimore, D. and Franklin, R. M. (1962). The effect of mengovirus infection on the activity of the DNA-dependent RNA polymerase of L-cells. Proc. Natl. Acad. Sci. U.S.A. 48, 1383-1390.

Beretta, L., Svitkin, Y., and Sonenberg, N. (1996). Rapamycin stimulates viral protein synthesis and augments the shutoff of host protein synthesis upon picornavirus infecton. J. Virol. 1282, 7903-7911.

Belsham, G. J., and N. Sonenberg, (1996) RNA-protein interactions in regulation of picornavirus RNA translational. Microbiol. Rev. 60:499-511

Bienz, K. and Egger, D. (1995). Immunocytochemistry and in situ hybridization in the electron microscope: combined application in the study of virus-infected cells. Histochem. Cell. Biol. 103, 325-338.

Bienz, K., Egger, D., Pfister, T., and Troxler, M. (1992). Structural and functional characterization of the poliovirus replication complex. J. Virol. 66, 2740-2747.

Bienz, K., Egger, D., Rasser, Y., and Bossart, W. (1983). Intracellular distribution of poliovirus proteins and the induction of virus-specific cytoplasmic structures. Virology 131, 39-48.

Borman, A. M., R. Kirchweger, E. Ziegler, R. E. Rhoads, T. Skern, and K. M. Kean. (1997) eIF4G and its proteolytic cleavage products: effect on initiation of protein synthesis from capped, uncapped, and IRES-containing mRNAs. RNA 3:186-196

Chen, D. and Huang, S. (2001). Nucleolar components involved in ribosome biogenesis cycle between the nucleolus and nucleoplasm in interphase cells. *J Cell Biol* 153, 169-176.

Clark, M. E., Hammerle, T., Wimmer, E., and Dasgupta, A. (1991). *Poliovirus* protease 3C converts an active form of transcription factor IIIC to an inactive form: A mechanism for inhibition of host cell polymerase III transcription by poliovirus. *EMBO Journal* 10, 2941-2948.

Clark, M. E., Lieberman, P. M., Berk, A. J., and Dasgupta, A. (1993). Direct cleavage of human TATA-binding protein by poliovirus 3C in vivo and in vitro. *Mol. and Cell. Biol.* 13, 1232-1237.

Corsi, A. K. and Schekman, R. (1996). Mechanism of polypeptide translocation into the endoplasmic reticulum. *J. Biol. Chem* 271, 30299-30302.

Darnell, J., Lodish, H., and Baltimore, D. (1990). "Molecular Cell Biology." Scientific American Books, Inc., New York.

Detjen, B. M., Lucas, J., and Wimmer, E. (1978). *Poliovirus* single-stranded RNA and double-stranded RNA: differential infectivity in enucleate cells. *J. Virol.* 27, 582-594.

Dingwall, C. and Laskey, R. A. (1991). Nuclear targeting sequences—a consensus? *Trends Biochem. Sci.* 16, 478-481.

Duke, G. M., Hoffman, M. A., and Palmenberg, A. C. (1992). Sequence and structural elements that contribute to efficient encephalomyocarditis viral RNA translation. *J. Virol.* 66, 1602-1609.

Duque, H. and Palmenberg, A. C. (1996). Epitope mapping of monoclonal antibodies raised to recombinant Mengo 3D protein. *Virus Genes* 13, 159-168.

Duque, H. and Palmenberg, A. C. (2001). Phenotypic characterization of three phylogenetically conserved stemloop motifs in the mengovirus 3' untranslated region. *J. Virol.* 73, 3111-3120.

Egger, D., Teterina, N., Ehrenfeld, E., and Bienz, K. (2000). Formation of the poliovirus replication complex requires coupled viral translation, vesicle production, and viral RNA synthesis. *J. Virol.* 74, 6570-6580.

Ehrenfeld, E. (1996) Initiation of translation by picornavirus RNAs, p. 549-573. In J. W. B. Hershey, M. B. Mathews, and N. Sonenberg (ed.), Translational control. Cold Spring Harbor Laboratory Press, Plainview, N.Y.

Flanegan, J. B. and Baltimore, D. (1977). *Poliovirus*-specific primer-dependent RNA polymerase able to copy poly(A). *Proc. Natl. Acad. Sci. U.S.A.* 74, 2677-2680.

Flanegan, J. B. and Baltimore, D. (1979). *Poliovirus* polyuridylic acid polymerase and RNA replicase have the same viral polypeptide. *J. Virol.* 29, 352-360.

Grigera, P. R., Vasquez, C., and Palmenberg, A. C. (1985). Foot-and-mouth disease virus capsid proteins VP0, VP1 and VP3 synthesized by in vitro translation are the major components of 14S particles. *Acta Virol.* 29, 449-454.

Gingras, A. C., Y. Svitkin, G. J. Belsham, A. Pause, and N. Sonenberg. (1996) Activation of the translational suppressor 4E-BP1 following infection with encephalomyocarditis virus and poliovirus. Proc. Natl. Acad. Sci. USA 93:5578-5583

Guarné, A., Tormo, J., Kirchweger, R., Pfistermueller, D., Fita, A., and Skern, T. (1998). Structure of the foot-and-mouth disease virus leader protease: A papain-like fold adapted for self-processing and eIF4G recognition. *EMBO J.* 17, 7469-7479.

Haghighat, A., Svitkin, Y., Novoa, I., Kuechler, E., Skern, T., and Sonenberg, N. (1996). The eIF4G-eIF4E complex is the target for direct cleavage by the rhinovirus 2A proteinase. *J. Virol.* 70, 8444-8450.

Hahn, H. and Palmenberg, A. C. (1995). Encephalomyocarditis viruses with short poly(C) tracts are more virulent than their Mengo virus counterparts. *J. Virol.* 69, 2697-2699.

Hahn, H. and Palmenberg, A. C. (2001). Deletion mapping of the encephalomyocarditis virus 2A protein and the adjacent primary cleavage site. *J. Virol.* 75, 7215-7218.

Hall, D. J. and Palmenberg, A. C. (1996a). Cleavage site mutations in the encephalomyocarditis virus P3 region lethally abrogate the normal processing cascade. *J. Virol.* 70, 5954-5961.

Hall, D. J. and Palmenberg, A. C. (1996). Mengo virus 3C proteinase: Recombinant expression, intergenus substrate cleavage and localization in vivo. *Virus Genes* 13, 99-110.

Hansen, J. L., Long, A. M., and Schultz, S. C. (1997). Structure of the RNA-dependent RNA polymerase of poliovirus. *Struct.* 5, 1109-1122.

Hensold, J. O., Barth-Baus, D., and Stratton, C. A. (1996). Inducers of erythroleukemic differentiation cause messenger RNAs that lack poly(A)-binding protein to accumulate in translationally inactive, salt-labile 80 S ribosomal complexes. *J. Biol. Chem.* 271, 23246-23254.

Hicks, G. R. and Raikhel, N. V. (1995). Protein import into the nucleus: an integrated view. *Annu. Rev. Cell. Dev. Biol.* 11, 155-188.

Hingorani, K., Szebeni, A., and Olson, M. O. (2000). Mapping and functional domains of nucleolar protein B23. *J. Biol. Chem.* 275, 24451-24459.

Hiscox, J. A. (2002). The nucleolus—a gateway to viral infection? *Arch Virol* 147, 1077-1089.

Hu, Y., Fisette, P. L., Denlinger, L. C., Guadarrama, A. G., Sommer, J. A., Proctor, R. A., and Bertics, P. J. (1998). Purinergic receptor modulation of lipopolysaccharide signaling and inducible nitric-oxide synthase expression in raw 264.7 Macrophages. *J. Biol. Chem.* 273, 27170-27175.

Jang, S. K., Krausslich, H. G., Nicklin, M. J. H., Duke, G. M., Palmenberg, A. C., and Wimmer, E. (1988). A segment of the 5' nontranslated region of encephalomyocarditis virus RNA directs internal entry of ribosomes during in vitro translation. *J. Virol.* 62, 2636-2643.

Jen, G., Birge, C. H., and Thach, R. E. (1978). Comparison of initiation rates of encephalomyocarditis virus and host protein synthesis in infected cells. *J. Virol.* 27, 640-647.

Jen, G., Detjen, B. M., and Thach, R. E. (1980). Shutoff of HeLa cell protein synthesis by encephalomyocarditis virus and poliovirus: a comparative study. *J. Virol.* 35, 150-156.

Kiessig, S., Reissmann, J., Rascher, C., Kullertz, G., Fischer, A., and Thunecke, F. (2001). Application of a green fluorescent fusion protein to study protein-protein interactions by electrophoretic methods. *Electrophoresis* 22, 1428-1435.

Ko, Y. G., Kang, Y. S., Kim, E. K., Park, S. G., and Kim, S. (2000). Nucleolar localization of human methionyl-tRNA synthetase and its role in ribosomal RNA synthesis. *J. Cell Biol.* 149, 567-574.

Krausslich, H. G., Nicklin, M. J. H., Toyoda, H., Etchison, D., and Wimmer, E. (1987). *Poliovirus* proteinase 2A induces cleavage of eucaryotic initiation factor 4F polypeptide p 220. *J. Virol.* 61, 2711-2718.

Kuhn, R. J. and Wimmer, E. (1987). The replication of picornaviruses. In "The Molecular Biology of the Positive Strand RNA viruses" (D. J. Rowlands, M. A. Mayo, and B. W. J. Mahy, Eds.), pp. 17-51. Academic Press Inc., London.

Lawrence, C., and R. E. Thach. (1974) Encephalomyocarditis virus infection of mouse plasmacytoma cells. I. Inhibition of cellular protein synthesis. J. Virol. 14:598-610

Lee, W. M., Wang, W., and Rueckert, R. R. (1995). Complete sequence of the RNA genome of human rhinovirus 16, a clinically useful common cold virus belonging to the ICAM-1 receptor group. *Virus Genes* 9, 177-181.

Li, Y. P., Busch, R. K., Valdez, B. C., and Busch, H. (1996). C23 interacts with B23, a putative nucleolar-localization-signal-binding protein. *Eur. J. Biochem.* 273, 153-158.

Liebig, H.-D., Ziegler, E., Yan, R., Hartmuth, K., Klump, H., Kowalski, H., Blaas, D., Sommergruber, W., Frasel, L., Lamphear, B., Rhoads, R., Kuechler, E., and Skern, T. (1993). Purification of two picornaviral 2A proteinases: Interaction with eIF-4y and influence on in vitro translation. *Biochemistry* 32, 7581-7588.

Lischka, P., Sorg, G., Kann, M., Winkler, M., and Stamminger, T. (2003). A nonconventional nuclear localization signal within the UL84 protein of human cytomegalovirus mediates nuclear import via the importin alpha/beta pathway. *J Virol* 77, 3734-3748.

Lloyd, R. E., M. J. Grubman, and E. Ehrenfeld. (1988) Relationship of p 220 cleavage during picornavirus infection to 2A proteinase sequencing. J. Virol. 62:4216-4223

Liu, J. L., Lee, L. F., Ye, Y., Qian, Z., and Kung, H. J. (1997). Nucleolar and nuclear localization properties of a herpesvirus bZIP oncoprotein, MEQ. *J. Virol.* 71, 3188-3196.

Lundquist, R. E., Ehrenfeld, E., and Maizel, J. V. (1974). Isolation of a viral polypeptide associated with the poliovirus replication complex. *Proc. Natl. Acad. Sci. U.S.A.* 71, 4774-4777.

Martin, L. R., Duke, G. M., Osorio, J. E., Hall, D. J., and Palmenberg, A. C. (1996). Mutational analysis of the Mengovirus poly(C) tract and surrounding heteropolymeric sequences. *J. Virol.* 70, 2027-2031.

Martin, L. R., Neal, Z. C., McBride, M. S., and Palmenberg, A. C. (2000). Mengovirus and encephalomyocarditis virus poly(C) tract lengths can affect virus growth in murine cell culture. *J. Virol.* 74, 3074-3081.

Medvedkina, O. A., Scarlat, I. V., Kalinina, N. O., and Agol, V. I. (1974). Virus-specific proteins associated with ribosomes of Krebs-II cells infected with encephalomyocarditis virus. *FEBS Lett.* 39, 4-9.

Melese, T. and Xue, Z. (1995). The nucleolus: an organelle formed by the act of building a ribosome. *Curr. Opin. Cell Biol.* 7, 319-324.

Michael, W. M. (2000). Nucleocytoplasmic shuttling signals: two for the price of one. *Trends Cell Biol.* 10, 46-50.

Molla, A., Paul, A. V., and Wimmer, E. (1991). Cell-free, de novo synthesis of *poliovirus*. *Science* 254, 1647-1651.

Mosenkis, J., S. Daniels-McQueen, S. Janovec, R. Duncan, J. W. Hershey, J. A. Grifo, W. C. Merrick, and R. E. Thach. (1985) Shutoff of host translation by encephalomyocarditis virus infection does not involve cleavage of the eucaryotic initiation factor 4F polypeptide that accompanies poliovirus infection. J. Virol. 54:643-645

Morrow, C. D., Navab, M., Peterson, C., Hocko, J., and Dasgupta, A. (1984). Antibody to poliovirus VPg precipitates in vitro synthesized RNA attached to VPg-precursor polypeptide(s). *Virus Res.* 1, 89-100.

Murre, C., McCaw, P. S., Vaessin, H., Caudy, M., Jan, L. Y., Jan, Y. N., Cabrera, C. V., Buskin, J. N., Hauschka, S. D., Lassar, A. B., and et, a. l. (1989). Interactions between heterologous helix-loop-helix proteins generate complexes that bind specifically to a common DNA sequence. *Cell* 58, 537-544.

Nomoto, A., Lee, Y. F., and Wimmer, E. (1976). The 5'-end of poliovirus mRNA is not capped with $m^7G(5')pppG(5')Np$. *Proc. Natl. Acad. Sci. U.S.A.* 73, 375-380.

Okuwaki, M., Iwamatsu, A., Tsujimoto, M., and Nagata, K. (2001). Identification of nucleophosmin/B23, an acidic nucleolar protein, as a stimulatory factor for in vitro replication of adenovirus DNA complexed with viral basic core proteins. *J. Mol. Biol.* 311, 41-45.

Pallansch, M. A., Kew, O. M., Palmenberg, A. C., Golini, F., Wimmer, E., and Rueckert, R. R. (1980). Picornaviral VPg sequences are contained in the replicase precursor. *J. Virol.* 35, 414-419.

Palmenberg, A. C. (1982). In vitro synthesis and assembly of picornaviral capsid intermediate structures. *J. Virol.* 44, 900-906.

Palmenberg, A. C. and Rueckert, R. R. (1982). Evidence for intramolecular self-cleavage of picornaviral replicase precursors. *J. Virol.* 41, 244-249.

Palmenberg, A. C. (1989). Cleavage specificity of the EMC 3C proteinase. In "Current Communications in Molecular Biology: Viral Proteinases as Targets for Chemotherapy" (H.-G. Krausslich, S. Oroszlan, and E. Wimmer, Eds.), pp. 27-32. Cold Spring Harbor Laboratory Press, Cold Spring Harbor, N.Y.

Palmenberg, A. C. and Sgro, J.-Y. (2001). Alignments and comparative profiles of picornavirus genera. In "Molecular Biology of Picornaviruses" (B. L. Semler and E. Wimmer, Eds.), pp. 149-158. ASM Press, New York.

Parks, G. D., Duke, G. M., and Palmenberg, A. C. (1986). Encephalomyocarditis 3C protease: efficient cell-free expression from clones which link viral 5' non-coding sequences to the P3 region. *J. Virol.* 60, 376-384.

Parks, G. D. and Palmenberg, A. C. (1987). Site-specific mutations at a picornavirus VP3/VP1 cleavage site disrupt in vitro processing and assembly of capsid precursors. *J. Virol.* 61, 3680-3687.

Parks, G. D., Baker, J. C., and Palmenberg, A. C. (1989). Proteolytic cleavage of encephalomyocarditis viral capsid region substrates by precursors to the 3C enzyme. *J. Virol.* 63, 1054-1058.

Pfister, T., Jones, K. W., and Wimmer, E. (2000). A cysteine-rich motif in poliovirus protein 2C(ATPase) is involved in RNA replication and binds zinc in vitro. *J. Virol.* 74, 334-343.

Pincus, S. E., Diamond, D., Emini, E. A., and Wimmer, E. (1986). Guanidine-selected mutants of poliovirus: mapping of point mutations to polypeptide 2C. *J. Virol.* 57, 638-646.

Racaniello, V. R. (2001). Picornaviridae: The viruses and their replication. In "Fields Virology" (D. M. Knipe and P. M. Mowley, Eds.), pp. 685-722. Lippincott Williams and Wilkins, Philadelphia, Pa.

Rothberg, P. G., Harris, T. J. R., Nomoto, A., and Wimmer, E. (1978). 04-(5'-uridylyl)tyrosine is the bond between the genome-linked protein and the RNA of poliovirus. *Proc. Natl. Acad. Sci. U.S.A.* 75, 4868-4872.

Rubinstein, S. J., Hammerle, T., Wimmer, E., and Dasgupta, A. (1992). Infection of HeLa cells with poliovirus results in modification of a complex that binds to the rRNA promoter. *J. Virol.* 66, 3062-3068.

Rueckert, R. R., Palmenberg, A. C., and Pallansch, M. A. (1980). Evidence for a self-cleaving precursor of virus-coded protease, RNA-replicase and VPg. In "Biosynthesis, modification and processing of cellular and viral polyproteins" (G. Koch and D. Richter, Eds.), pp. 263-275. Academic Press, New York.

Rueckert, R. R. and Pallansch, M. A. (1981). Preparation and characterization of encephalomyocarditis virus. *Methods Enzymol.* 78, 315-325.

Rueckert, R. R. ( ) Picornaviridae: the viruses and their replication, p. 609-654. In B. N. Fields (ed.), *Fields virology*, vol. 1. Lippincott-Raven Publishers, Philadelphia, Pa.

Sambrook, J., Fritsch, E. F., and Maniatis, T. (1989). "Molecular Cloning: A Laboratory Manual." Cold Spring Harbor Laboratory, Cold Spring Harbor, N.Y.

Shih, D. S., Shih, C. T., Zimmern, D., Rueckert, R. R., and Kaesberg, P. (1979). Translation of encephalomyocarditis virus RNA in reticulocyte lysates: Kinetic analysis of the formation of virion proteins and a protein required for processing. *J. Virol.* 30, 472-480.

Snedecor, G. W. and Cochran, W. G. (1980). "Statistical Methods." The Iowa State University Press, Ames, Iowa.

Sonenberg, N. (1996) mRNA 5' cap-binding protein eIF4E and control of cell growth, p. 245-269. In J. W. B. Hershey, M. B. Mathews, and N. Sonenberg (ed.), Translational control. Cold Spring Harbor Laboratory Press, Plainview, N.Y.

Stauber, R. H. and Pavlakis, G. N. (1998). Intracellular trafficking and interactions of the HIV-1 Tat protein. *Virology* 252, 126-136.

Stern, R. V. and Frieden, E. (1993). Partial purification of the rat erythrocyte ceruloplasmin receptor monitored by an electrophoresis mobility shift assay. *Anal. Biochem.* 212, 221-228.

Stuger, R., Timmers, A. C. J., Raue, H. A., and van'n Riet, J. (2000). Nuclear import of ribosomal proteins: evidence for a novel type of nucleolar localization signal. In "The Ribosome Structure, Function, Antibiotics and Cellular Interactions" pp. 205-217. ASM Press, Washington.

Svitkin, Y. V., Ginevskaya, V. A., Ugarova, T. Y., and Agol, V. I. (1978). A cell-free model of the encephalomyocarditis virus-induced inhibition of host cell protein synthesis. *Virology* 87, 199-233.

Svitkin, Y. V., Hahn, H., Gingras, A. C., Palmenberg, A. C., and Sonenberg, N. (1998). Rapamycin and wortmannin enhance replication of a defective encephalomyocarditis virus. *J. Virol.* 72, 5811-5819.

Srivastava, M. and Pollard, H. B. (1999). Molecular dissection of nucleolin's role in growth and cell proliferation: new insights. *FASEB J.* 13, 1911-1922.

Szebeni, A., Herrera, J. E., and Olson, M. O. (1995). Interaction of nucleolar protein B23 with peptides related to nuclear localization signals. *Biochemistry* 34, 2037-2042.

Szebeni, A., Mehrotra, B., Baumann, A., Adam, S. A., Wingfield, P. T., and Olson, M. O. (1997). Nucleolar protein B23 stimulates nuclear import of the HIV-1 rev protein and NLS-conjugated albumin. *Biochemistry* 36, 3941-3949.

Valdez, B. C., Perlaky, L., Henning, D., Saijo, Y., Chan, P. K., and Busch, H. (1994). Identification of the nuclear and nucleolar localization signals of the protein p 120. Interaction with translocation protein B23. *J. Biol. Chem.* 269, 23776-23783.

Van Dyke, T. A. and Flanegan, J. B. (1980). Identification of poliovirus polypeptide p63 as a soluble RNA-dependent RNA polymerase. *J. Virol.* 35, 732-740.

Waggoner, S. and Sarnow, P. (1998). Viral ribonucleoprotein complex formation and nucleolar-cytoplasmic relocalization of nucleolin in poliovirus-infected cells. *J. Virol.* 72, 6699-6709.

Weidman, M. K., Yalamanchili, P., Ng, B., Tsai, W., and Dasgupta, A. (2001). *Poliovirus* 3C protease-mediated degradation of transcriptional activator p53 requires a cellular activity. *Virology* 291, 260-271.

Wyckoff, E. E., R. E. Lloyd, and E. Ehrenfeld. (1992) Relationship of eukaryotic initiation factor 3 to poliovirus-induced p220 cleavage activity. J. Virol. 66:2943-2951

Yalamanchili, P., Banejee, R., and Dasgupta, A. (1997a). *Poliovirus*-encoded protease $2A^{pro}$ cleaves the TATA-binding protein but does not inhibit host cell RNA polymerase II transcription in vitro. *J. Virol.* 71, 6881-6886.

Yalamanchili, P., Datta, U., and Dasgupta, A. (1997b). Inhibition of host cell transcription by poliovirus: cleavage of transcription factor CREB by poliovirus-encoded protease 3 Cpro. *J Virol* 71, 1220-1226.

Yalamanchili, P., Weidman, K., and Dasgupta, A. (1997c). Cleavage of transcriptional activator Oct-1 by poliovirus encoded protease $3C^{pro}$. *Virology* 239, 176-185.

Zoll, J., van Kuppeveld, F. J. M., Galama, J. M. D., and Melchers, W. J. G. (1998). Genetic analysis of mengovirus protein 2A: its function in polyprotein processing and virus reproduction. *J. Gen. Virol.* 79, 17-25.

---

We claim:

1. A nucleic acid construct comprising:

a DNA dependent RNA polymerase promoter;

a 2A cardiovirus polynucleotide sequence encoding a 2A polypeptide, wherein the 2A polynucleotide is operably linked to the promoter, wherein the 2A polypeptide is selected from the group consisting of SEQ ID NOs: 43, 44, 45, 46, 47, 48, 49, and 50;

a first foreign polynucleotide encoding a detectable polypeptide, wherein the first foreign polynucleotide is immediately downstream of and operably linked to the 2A polynucleotide;

an IRES polynucleotide sequence, wherein the IRES sequence is immediately downstream of the first foreign polynucleotide; and a second foreign polynucleotide encoding a detectable polypeptide, wherein the second foreign polynucleotide is immediately downstream of and operably linked to the IRES sequence.

2. A nucleic acid construct comprising:

a DNA dependent RNA polymerase promoter;

a first foreign polynucleotide encoding a detectable polypeptide, wherein the first foreign polynucleotide is immediately downstream of and operably linked to the promoter;

an IRES polynucleotide sequence, wherein the IRES sequence is immediately downstream of the first foreign polynucleotide;

a 2A cardiovirus polynucleotide sequence encoding a 2A polypeptide, wherein the 2A polynucleotide is operably linked to the IRES sequence, wherein the 2A polypeptide is selected from the group consisting of SEQ ID NOs: 43, 44, 45, 46, 47, 48, 49, and 50; and a second foreign polynucleotide encoding a detectable polypeptide, wherein the second foreign polynucleotide is immediately downstream of and operably linked to the 2A polynucleotide.

3. A nucleic acid construct comprising:

a DNA dependent RNA polymerase promoter;

a first IRES sequence, wherein the first IRES sequence is immediately downstream of the promoter;

a first foreign polynucleotide encoding a detectable polypeptide, wherein the first foreign polynucleotide is immediately downstream of the first IRES sequence;

a second IRES sequence, wherein the second IRES sequence is immediately downstream of the first foreign polynucleotide;

a 2A cardiovirus polynucleotide sequence encoding a 2A polypeptide, wherein the 2A polynucleotide is operably linked to the second IRES sequence, wherein the 2A polypeptide is selected from the group consisting of SEQ ID NOs: 43, 44, 45, 46, 47, 48, 49, and 50; and a second foreign polynucleotide encoding a detectable polypeptide, wherein the second foreign polynucleotide is immediately downstream of and operably linked to the 2A polynucleotide.

4. A nucleic acid construct comprising:

a DNA dependent RNA polymerase promoter;

a first IRES sequence, wherein the first IRES sequence is immediately downstream of the promoter;

a 2A cardiovirus polynucleotide sequence encoding a 2A polypeptide, wherein the 2A polynucleotide is operably linked to the first IRES sequence, wherein the 2A polypeptide is selected from the group consisting of SEQ ID NOs: 43, 44, 45, 46, 47, 48, 49, and 50;

a first foreign polynucleotide encoding a detectable polypeptide, wherein the first foreign polynucleotide is immediately downstream of the 2A sequence;

a second IRES sequence, wherein the second IRES sequence is immediately downstream of the first foreign polynucleotide; and a second foreign polynucleotide encoding a detectable polypeptide, wherein the second foreign polynucleotide is immediately downstream of and operably linked to the second IRES sequence.

5. A nucleic acid construct comprising:

a first DNA dependent RNA polymerase promoter;

a 2A cardiovirus polynucleotide sequence encoding a 2A polypeptide, wherein the 2A polynucleotide is operably linked to the first promoter, wherein the 2A polypeptide is selected from the group consisting of SEQ ID NOs: 43, 44, 45, 46, 47, 48, 49, and 50;

a first foreign polynucleotide encoding a detectable polypeptide, wherein the first foreign polynucleotide is immediately downstream of and operably linked to the 2A polynucleotide;

a second DNA dependent RNA polymerase promoter, wherein the second promoter is immediately downstream of the first foreign polynucleotide;

an IRES polynucleotide sequence, wherein the IRES sequence is immediately downstream of the second promoter; and a second foreign polynucleotide encoding a detectable polypeptide, wherein the second foreign polynucleotide is immediately downstream of and operably linked to the IRES sequence.

6. A nucleic acid construct comprising:

a DNA dependent RNA polymerase promoter, or both the promoter and an IRES sequence; and a 2A cardiovirus polynucleotide sequence encoding a 2A polypeptide, wherein the expression of the 2A polypeptide in either eukaryotic cells or cell-free systems inhibits either mRNA transcription, or cap-dependent mRNA translation, wherein the 2A polypeptide is selected from the group consisting of SEQ ID NOs: 43, 44, 45, 46, 47, 48, 49, and 50, wherein the 2A cardiovirus polynucleotide sequence includes a mutation located within a nuclear localization signal (NLS) sequence or a carboxyl terminal 2A primary cleavage sequence.

* * * * *

SEQUENCE LISTING

```
<160> NUMBER OF SEQ ID NOS: 50

<210> SEQ ID NO 1
<211> LENGTH: 20
<212> TYPE: PRT
<213> ORGANISM: Encephalomyocarditis virus

<400> SEQUENCE: 1

Gly Pro Tyr Asn Glu Thr Ala Arg Val Lys Pro Lys Thr Leu Gln Leu
1               5                   10                  15

Leu Asp Ile Gln
            20

<210> SEQ ID NO 2
<211> LENGTH: 30
<212> TYPE: DNA
<213> ORGANISM: Artificial
<220> FEATURE:
```

```
<223> OTHER INFORMATION: Synthetic oligonucleotide

<400> SEQUENCE: 2
cgtaccagat aaaacagcac tacgccccac                                              30

<210> SEQ ID NO 3
<211> LENGTH: 16
<212> TYPE: DNA
<213> ORGANISM: Artificial
<220> FEATURE:
<223> OTHER INFORMATION: Synthetic oligonucleotide

<400> SEQUENCE: 3
cccagtggaa accggg                                                             16

<210> SEQ ID NO 4
<211> LENGTH: 29
<212> TYPE: DNA
<213> ORGANISM: Artificial
<220> FEATURE:
<223> OTHER INFORMATION: Synthetic oligonucleotide

<400> SEQUENCE: 4
gtgctgtttt atctggtacg tgaatacgg                                               29

<210> SEQ ID NO 5
<211> LENGTH: 25
<212> TYPE: DNA
<213> ORGANISM: Artificial
<220> FEATURE:
<223> OTHER INFORMATION: Synthetic oligonucleotide

<400> SEQUENCE: 5
ctacgacatc tgttctgcgc attcc                                                   25

<210> SEQ ID NO 6
<211> LENGTH: 30
<212> TYPE: DNA
<213> ORGANISM: Artificial
<220> FEATURE:
<223> OTHER INFORMATION: Synthetic oligonucleotide

<400> SEQUENCE: 6
cgtaccacgt gaaacagcac tacgccccac                                              30

<210> SEQ ID NO 7
<211> LENGTH: 30
<212> TYPE: DNA
<213> ORGANISM: Artificial
<220> FEATURE:
<223> OTHER INFORMATION: Synthetic oligonucleotide

<400> SEQUENCE: 7
agtgctgttt cacgtggtac gtgaatacgg                                              30

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide

<400> SEQUENCE: 8
caacaacaat atcccttgaa a                                                       21

<210> SEQ ID NO 9
```

```
<211> LENGTH: 21
<212> TYPE: DNA
<213> ORGANISM: Artificial
<220> FEATURE:
<223> OTHER INFORMATION: Synthetic oliogonucleotide

<400> SEQUENCE: 9
aactacccgt caatggactc t                                            21

<210> SEQ ID NO 10
<211> LENGTH: 21
<212> TYPE: DNA
<213> ORGANISM: Artificial
<220> FEATURE:
<223> OTHER INFORMATION: Synthetic oliogonucleotide

<400> SEQUENCE: 10
tttcaaggga tattgttgtt g                                            21

<210> SEQ ID NO 11
<211> LENGTH: 21
<212> TYPE: DNA
<213> ORGANISM: Artificial
<220> FEATURE:
<223> OTHER INFORMATION: Synthetic oligonucleotide

<400> SEQUENCE: 11
ttgataaaga tttcccttgc c                                            21

<210> SEQ ID NO 12
<211> LENGTH: 21
<212> TYPE: DNA
<213> ORGANISM: Artificial
<220> FEATURE:
<223> OTHER INFORMATION: Synthetic oligonucleotide

<400> SEQUENCE: 12
gcaaccctac agaacccggt g                                            21

<210> SEQ ID NO 13
<211> LENGTH: 24
<212> TYPE: DNA
<213> ORGANISM: Artificial
<220> FEATURE:
<223> OTHER INFORMATION: Synthetic oligonucleotide

<400> SEQUENCE: 13
gccggtccaa gaatttcacc tcta                                         24

<210> SEQ ID NO 14
<211> LENGTH: 21
<212> TYPE: DNA
<213> ORGANISM: Artificial
<220> FEATURE:
<223> OTHER INFORMATION: Synthetic oligonucleotide

<400> SEQUENCE: 14
gtcgagggct gactttcaat a                                            21

<210> SEQ ID NO 15
<211> LENGTH: 25
<212> TYPE: DNA
<213> ORGANISM: Artificial
<220> FEATURE:
<223> OTHER INFORMATION: Synthetic oligonucleotide

<400> SEQUENCE: 15
```
ccacgatacc aaagttgtca tggat                                    25

<210> SEQ ID NO 16
<211> LENGTH: 11
<212> TYPE: PRT
<213> ORGANISM: Artificial
<220> FEATURE:
<223> OTHER INFORMATION: Synthetic peptide

<400> SEQUENCE: 16

Tyr His Lys Arg Ile Arg Pro Phe Arg Leu Pro
1               5                   10

<210> SEQ ID NO 17
<211> LENGTH: 6
<212> TYPE: PRT
<213> ORGANISM: Artificial
<220> FEATURE:
<223> OTHER INFORMATION: Synthetic peptide

<400> SEQUENCE: 17

Gly Lys Lys Lys Pro Gly
1               5

<210> SEQ ID NO 18
<211> LENGTH: 56
<212> TYPE: PRT
<213> ORGANISM: Theiler's encephalomyelitis virus

<400> SEQUENCE: 18

Ser Ile Tyr Lys Gly Arg Tyr Arg Ser Trp Lys Pro Ile His Asp
1               5                   10                  15

Glu Leu Val Asp Arg Gly Tyr Thr Ile Phe Gly Glu Phe Phe Lys Ala
            20                  25                  30

Val Arg Gly Tyr His Ala Asp Tyr Tyr Arg Gln Arg Leu Ile His Asp
        35                  40                  45

Val Glu Thr Asn Pro Gly Pro Val
    50                  55

<210> SEQ ID NO 19
<211> LENGTH: 56
<212> TYPE: PRT
<213> ORGANISM: Theiler's encephalomyelitis virus

<400> SEQUENCE: 19

Thr Ile Tyr Lys Gly Arg Tyr Arg Ser Trp Lys Pro Ile His Asp
1               5                   10                  15

Glu Leu Val Asp Arg Gly Tyr Thr Thr Phe Arg Glu Phe Phe Lys Ala
            20                  25                  30

Val Arg Gly Tyr His Ala Asp Tyr Tyr Lys Gln Arg Leu Ile His Asp
        35                  40                  45

Val Glu Met Asn Pro Gly Pro Val
    50                  55

<210> SEQ ID NO 20
<211> LENGTH: 56
<212> TYPE: PRT
<213> ORGANISM: Theiler's encephalomyelitis virus

<400> SEQUENCE: 20

Ser Ile Tyr Lys Gly Arg Tyr Arg Ser Trp Lys Pro Ile His Asp
1               5                   10                  15

Glu Leu Val Asp Arg Gly Tyr Thr Thr Phe Gly Glu Phe Phe Arg Ala

```
                    20                  25                  30

Val Arg Ala Tyr His Ala Asp Tyr Tyr Lys Gln Arg Leu Ile His Asp
            35                  40                  45

Val Glu Met Asn Pro Gly Pro Val
        50                  55

<210> SEQ ID NO 21
<211> LENGTH: 60
<212> TYPE: PRT
<213> ORGANISM: Mengo virus

<400> SEQUENCE: 21

Asp Val Tyr His Lys Arg Ile Arg Pro Phe Arg Leu Pro Leu Val Gln
1               5                   10                  15

Lys Glu Trp Arg Thr Cys Glu Glu Asn Val Phe Gly Leu Tyr His Val
                20                  25                  30

Phe Glu Thr His Tyr Ala Gly Tyr Phe Ser Asp Leu Leu Ile His Asp
            35                  40                  45

Val Glu Thr Asn Pro Gly Pro Phe Thr Phe Lys Pro
        50                  55                  60

<210> SEQ ID NO 22
<211> LENGTH: 60
<212> TYPE: PRT
<213> ORGANISM: Encephalomyocarditis virus

<400> SEQUENCE: 22

Asp Ile Tyr Tyr Lys Arg Val Arg Pro Phe Arg Leu Pro Leu Val Gln
1               5                   10                  15

Lys Glu Trp Pro Val Arg Glu Glu Asn Val Phe Gly Leu Tyr Arg Ile
                20                  25                  30

Phe Asn Ala His Tyr Ala Gly Tyr Phe Ala Asp Leu Leu Ile His Asp
            35                  40                  45

Ile Glu Thr Asn Pro Gly Pro Phe Met Phe Arg Pro
        50                  55                  60

<210> SEQ ID NO 23
<211> LENGTH: 60
<212> TYPE: PRT
<213> ORGANISM: Encephalomyocarditis virus

<400> SEQUENCE: 23

Asp Val Tyr His Lys Arg Ile Arg Pro Phe Arg Leu Pro Leu Val Gln
1               5                   10                  15

Lys Glu Trp Asn Val Arg Glu Glu Asn Val Phe Gly Leu Tyr Ser Ile
                20                  25                  30

Phe Asn Ala His Tyr Ala Gly Tyr Phe Ala Asp Leu Leu Ile His Asp
            35                  40                  45

Ile Glu Thr Asn Pro Gly Pro Phe Met Ala Lys Pro
        50                  55                  60

<210> SEQ ID NO 24
<211> LENGTH: 60
<212> TYPE: PRT
<213> ORGANISM: Encephalomyocarditis virus

<400> SEQUENCE: 24

Asp Val Tyr His Lys Arg Ile Arg Pro Phe Arg Leu Pro Leu Val Gln
1               5                   10                  15

Lys Glu Trp Asn Val Arg Glu Glu Asn Val Phe Gly Leu Tyr Ser Ile
```

```
                20                  25                  30

Phe Asn Ala His Tyr Ala Gly Tyr Phe Ala Asp Leu Leu Ile His Asp
        35                  40                  45

Ile Glu Thr Asn Pro Gly Pro Phe Met Ala Lys Pro
    50                  55                  60

<210> SEQ ID NO 25
<211> LENGTH: 60
<212> TYPE: PRT
<213> ORGANISM: Encephalomyocarditis virus

<400> SEQUENCE: 25

Asp Val Tyr His Lys Arg Ile Arg Pro Phe Arg Leu Pro Leu Val Gln
1               5                   10                  15

Lys Glu Trp Asn Val Arg Glu Glu Asn Val Phe Gly Leu Tyr Ser Ile
            20                  25                  30

Phe Asn Ala His Tyr Ala Gly Tyr Phe Ala Asp Leu Leu Ile His Asp
        35                  40                  45

Ile Glu Thr Asn Pro Gly Pro Phe Met Ala Lys Pro
    50                  55                  60

<210> SEQ ID NO 26
<211> LENGTH: 54
<212> TYPE: PRT
<213> ORGANISM: Equine Rhinitis A Virus

<400> SEQUENCE: 26

Ser Val Ala Phe Cys Ser Leu Val Ser Arg Asp Ala Leu Glu Arg Thr
1               5                   10                  15

Leu Pro Gln Lys Gln Gly Asn Val Val Arg Leu Asp Asp Val Arg
            20                  25                  30

Val Ser Val Pro Arg Arg Thr Lys Leu Val Lys Ser Leu Ala Tyr Pro
        35                  40                  45

Val Phe Lys Pro Asp Tyr
    50

<210> SEQ ID NO 27
<211> LENGTH: 55
<212> TYPE: PRT
<213> ORGANISM: Foot-and-mouth disease virus

<400> SEQUENCE: 27

Cys Val Ser Arg Ser Met Leu Leu Lys Met Lys Ala His Ile Asp Pro
1               5                   10                  15

Glu Pro His His Glu Gly Leu Ile Val Asp Thr Arg Asp Val Glu Glu
            20                  25                  30

Arg Val His Val Met Arg Lys Thr Lys Leu Ala Pro Thr Val Ala His
        35                  40                  45

Gly Val Phe Asn Pro Glu Phe
    50                  55

<210> SEQ ID NO 28
<211> LENGTH: 55
<212> TYPE: PRT
<213> ORGANISM: Foot-and-mouth disease virus

<400> SEQUENCE: 28

Cys Val Ser Lys Ser Met Leu Leu Gln Met Lys Ala His Val Asp Pro
1               5                   10                  15

Glu Pro His His Glu Gly Leu Ile Val Asp Thr Arg Asp Val Glu Glu
```

```
                   20                  25                  30
Arg Val His Val Met Arg Lys Thr Lys Leu Ala Pro Thr Val Ala Arg
        35                  40                  45

Gly Val Leu Gln Pro Glu Tyr
        50                  55

<210> SEQ ID NO 29
<211> LENGTH: 50
<212> TYPE: PRT
<213> ORGANISM: Encephalomyocarditis virus

<400> SEQUENCE: 29

Ile Val Ser Gln Glu Met Ile Arg Ala Val Val Asn Ala Phe Glu Pro
1               5                   10                  15

Gln Gly Ala Leu Glu Arg Leu Pro Asp Gly Pro Arg Ile His Val Pro
            20                  25                  30

Arg Lys Thr Ala Leu Arg Pro Thr Val Ala Arg Gln Val Phe Gln Pro
        35                  40                  45

Ala Tyr
    50

<210> SEQ ID NO 30
<211> LENGTH: 50
<212> TYPE: PRT
<213> ORGANISM: Mengo virus

<400> SEQUENCE: 30

Ile Ile Ser Gln Glu Met Ile Asp Ala Val Val Gln Ala Phe Glu Pro
1               5                   10                  15

Gln Gly Ala Leu Glu Arg Leu Pro Asp Gly Pro Arg Ile His Val Pro
            20                  25                  30

Arg Lys Thr Ala Leu Arg Pro Thr Val Ala Arg Gln Val Phe Gln Pro
        35                  40                  45

Ala Phe
    50

<210> SEQ ID NO 31
<211> LENGTH: 53
<212> TYPE: PRT
<213> ORGANISM: Theiler's encephalomyelitis virus

<400> SEQUENCE: 31

Ile Ile Thr Lys Glu Leu Ile Glu Ala Ala Lys Ser Met Leu Ala
1               5                   10                  15

Leu Glu Pro Gln Gly Ala Ile Val Asp Ile Ala Thr Gly Ser Val Val
            20                  25                  30

His Val Pro Arg Lys Thr Lys Leu Arg Arg Thr Val Ala His Asp Val
        35                  40                  45

Phe Gln Pro Lys Phe
        50

<210> SEQ ID NO 32
<211> LENGTH: 51
<212> TYPE: PRT
<213> ORGANISM: Hepatitis A virus

<400> SEQUENCE: 32

Leu Val Thr Gln Glu Met Phe Gln Asn Ile Asp Lys Lys Ile Glu Ser
1               5                   10                  15

Gln Arg Ile Met Lys Val Glu Phe Thr Gln Cys Ser Met Asn Val Val
```

```
            20                  25                  30

Ser Lys Thr Leu Phe Arg Lys Ser Pro Ile Tyr His His Ile Asp Lys
        35                  40                  45

Thr Met Ile
    50

<210> SEQ ID NO 33
<211> LENGTH: 51
<212> TYPE: PRT
<213> ORGANISM: Hepatitis A virus

<400> SEQUENCE: 33

Leu Val Thr Gln Glu Met Phe Gln Asn Ile Glu Lys Lys Ile Glu Ser
1               5                   10                  15

Gln Arg Ile Met Lys Val Glu Phe Thr Gln Cys Ser Met Asn Val Val
            20                  25                  30

Ser Lys Thr Leu Phe Lys Lys Ser Pro Ile His His His Ile Asp Arg
        35                  40                  45

Asn Met Ile
    50

<210> SEQ ID NO 34
<211> LENGTH: 49
<212> TYPE: PRT
<213> ORGANISM: Human poliovirus 1 strain Sabin 1

<400> SEQUENCE: 34

Ala Leu Lys Arg Ser Tyr Phe Thr Gln Ser Gln Gly Glu Ile Gln Trp
1               5                   10                  15

Met Arg Pro Ser Lys Glu Val Gly Tyr Pro Ile Ile Asn Ala Pro Ser
            20                  25                  30

Lys Thr Lys Leu Glu Pro Ser Ala Phe His Tyr Val Phe Glu Gly Val
        35                  40                  45

Lys

<210> SEQ ID NO 35
<211> LENGTH: 45
<212> TYPE: PRT
<213> ORGANISM: Human enterovirus 70

<400> SEQUENCE: 35

Met Leu Leu Gln Asn Tyr Phe Thr Glu Lys Gln Gly Glu Ile Val Ser
1               5                   10                  15

Ile Glu Lys Thr Gly Val Phe Ile Asn Ala Pro Ala Lys Thr Lys Leu
            20                  25                  30

Glu Pro Ser Val Phe His Glu Val Phe Glu Gly Val Lys
        35                  40                  45

<210> SEQ ID NO 36
<211> LENGTH: 49
<212> TYPE: PRT
<213> ORGANISM: Human coxsackievirus B 5

<400> SEQUENCE: 36

Ala Leu Leu Lys His Tyr Phe Asn Asp Glu Gln Gly Glu Ile Glu Phe
1               5                   10                  15

Ile Glu Ser Ser Lys Glu Ala Gly Leu Pro Val Ile Asn Thr Pro Ser
            20                  25                  30

Lys Thr Lys Leu Glu Pro Ser Val Phe His Gln Val Phe Glu Gly Asn
        35                  40                  45
```

Lys

<210> SEQ ID NO 37
<211> LENGTH: 49
<212> TYPE: PRT
<213> ORGANISM: Swine Vesicular Disease Virus

<400> SEQUENCE: 37

Ala Leu Leu Arg His Tyr Phe Asn Glu Glu Gln Gly Glu Ile Glu Phe
1               5                   10                  15

Ile Glu Ser Ser Lys Asp Ala Gly Phe Pro Val Ile Asn Thr Pro Ser
            20                  25                  30

Lys Thr Lys Leu Glu Pro Ser Val Phe His His Val Phe Glu Gly Asn
        35                  40                  45

Lys

<210> SEQ ID NO 38
<211> LENGTH: 49
<212> TYPE: PRT
<213> ORGANISM: Human rhinovirus 2

<400> SEQUENCE: 38

Met Leu Leu Arg Ser Tyr Phe Thr Asp Val Gln Gly Gln Ile Thr Leu
1               5                   10                  15

Ser Lys Lys Thr Ser Glu Cys Asn Leu Pro Ser Ile His Thr Pro Cys
            20                  25                  30

Lys Thr Lys Leu Gln Pro Ser Val Phe Tyr Asp Val Phe Pro Gly Ser
        35                  40                  45

Lys

<210> SEQ ID NO 39
<211> LENGTH: 49
<212> TYPE: PRT
<213> ORGANISM: Human rhinovirus 14

<400> SEQUENCE: 39

Gln Leu Lys Lys Gln Tyr Phe Val Glu Lys Gln Gly Gln Val Ile Ala
1               5                   10                  15

Arg His Lys Val Arg Glu Phe Asn Ile Asn Pro Val Asn Thr Pro Thr
            20                  25                  30

Lys Ser Lys Leu His Pro Ser Val Phe Tyr Asp Val Phe Pro Gly Asp
        35                  40                  45

Lys

<210> SEQ ID NO 40
<211> LENGTH: 49
<212> TYPE: PRT
<213> ORGANISM: Human rhinovirus 16

<400> SEQUENCE: 40

Met Leu Leu Arg Ser Tyr Phe Thr Glu Gln Gln Gly Gln Ile Gln Ile
1               5                   10                  15

Ser Lys His Val Lys Asp Val Gly Leu Pro Ser Ile His Thr Pro Thr
            20                  25                  30

Lys Thr Lys Leu Gln Pro Ser Val Phe Tyr Asp Ile Phe Pro Gly Ser
        35                  40                  45

Lys

```
<210> SEQ ID NO 41
<211> LENGTH: 19
<212> TYPE: PRT
<213> ORGANISM: Encephalomyocarditis virus

<400> SEQUENCE: 41

Tyr Ala Gly Tyr Phe Ala Asp Leu Leu Ile His Asp Ile Glu Thr Asn
1               5                   10                  15

Pro Gly Pro

<210> SEQ ID NO 42
<211> LENGTH: 8
<212> TYPE: PRT
<213> ORGANISM: Encephalomyocarditis virus

<400> SEQUENCE: 42

Pro Arg Lys Thr Ala Leu Arg Pro
1               5

<210> SEQ ID NO 43
<211> LENGTH: 133
<212> TYPE: PRT
<213> ORGANISM: Theiler's encephalomyelitis virus

<400> SEQUENCE: 43

Asn Pro Ala Ala Leu Tyr Arg Ile Asp Leu Phe Ile Thr Phe Thr Asp
1               5                   10                  15

Glu Phe Ile Thr Phe Asp Tyr Lys Val His Gly Arg Pro Val Leu Thr
                20                  25                  30

Phe Arg Ile Pro Gly Phe Gly Leu Thr Pro Ala Gly Arg Met Leu Val
            35                  40                  45

Cys Met Gly Glu Gln Pro Ala His Gly Pro Phe Thr Ser Ser Arg Ser
    50                  55                  60

Leu Tyr His Val Ile Phe Thr Ala Thr Cys Ser Ser Phe Ser Phe Ser
65                  70                  75                  80

Ile Tyr Lys Gly Arg Tyr Arg Ser Trp Lys Lys Pro Ile His Asp Glu
                85                  90                  95

Leu Val Asp Arg Gly Tyr Thr Thr Phe Gly Glu Phe Phe Lys Ala Val
                100                 105                 110

Arg Gly Tyr His Ala Asp Tyr Tyr Arg Gln Arg Leu Ile His Asp Val
            115                 120                 125

Glu Thr Asn Pro Gly
        130

<210> SEQ ID NO 44
<211> LENGTH: 133
<212> TYPE: PRT
<213> ORGANISM: Theiler's encephalomyelitis virus

<400> SEQUENCE: 44

Asn Pro Ala Ser Leu Tyr Arg Ile Asp Leu Phe Ile Thr Phe Thr Asp
1               5                   10                  15

Glu Leu Ile Thr Phe Asp Tyr Lys Val His Gly Arg Pro Val Leu Thr
                20                  25                  30

Phe Arg Ile Pro Gly Phe Gly Leu Thr Pro Ala Gly Arg Met Leu Val
            35                  40                  45

Cys Met Gly Ala Lys Pro Ala His Ser Pro Thr Ser Ser Lys Ser
    50                  55                  60

Leu Tyr His Val Ile Phe Thr Ser Thr Cys Asn Ser Phe Ser Phe Thr
65                  70                  75                  80
```

```
Ile Tyr Lys Gly Arg Tyr Arg Ser Trp Lys Lys Pro Ile His Asp Glu
                85                  90                  95

Leu Val Asp Arg Gly Tyr Thr Thr Phe Arg Glu Phe Lys Ala Val
            100                 105                 110

Arg Gly Tyr His Ala Asp Tyr Tyr Lys Gln Arg Leu Ile His Asp Val
            115                 120                 125

Glu Met Asn Pro Gly
        130

<210> SEQ ID NO 45
<211> LENGTH: 133
<212> TYPE: PRT
<213> ORGANISM: Theiler's encephalomyelitis virus

<400> SEQUENCE: 45

Asn Pro Ala Ala Phe Tyr Arg Ile Asp Leu Phe Ile Thr Phe Ile Asp
1               5                   10                  15

Glu Phe Ile Thr Phe Asp Tyr Lys Val His Gly Arg Pro Val Leu Thr
            20                  25                  30

Phe Arg Ile Pro Gly Phe Gly Leu Thr Pro Ala Gly Arg Met Leu Val
        35                  40                  45

Cys Met Gly Glu Lys Pro Ala His Gly Pro Phe Thr Ser Ser Arg Ser
    50                  55                  60

Leu Tyr His Val Ile Phe Thr Ala Thr Cys Ser Ser Phe Ser Phe Ser
65                  70                  75                  80

Ile Tyr Lys Gly Arg Tyr Arg Ser Trp Lys Lys Pro Ile His Asp Glu
                85                  90                  95

Leu Val Asp Arg Gly Tyr Thr Thr Phe Gly Glu Phe Phe Arg Ala Val
            100                 105                 110

Arg Ala Tyr His Ala Asp Tyr Tyr Lys Gln Arg Leu Ile His Asp Val
            115                 120                 125

Glu Met Asn Pro Gly
        130

<210> SEQ ID NO 46
<211> LENGTH: 143
<212> TYPE: PRT
<213> ORGANISM: Mengo virus

<400> SEQUENCE: 46

Ser Pro Asn Pro Leu Asp Val Ser Lys Thr Tyr Pro Thr Leu His Ile
1               5                   10                  15

Leu Leu Gln Phe Asn His Arg Gly Leu Glu Ala Arg Ile Phe Arg His
            20                  25                  30

Gly Gln Leu Trp Ala Glu Thr His Ala Glu Val Val Leu Arg Ser Lys
        35                  40                  45

Thr Lys Gln Ile Ser Phe Leu Ser Asn Gly Ser Tyr Pro Ser Met Asp
    50                  55                  60

Ala Thr Thr Pro Leu Asn Pro Trp Lys Ser Thr Tyr Gln Ala Val Leu
65                  70                  75                  80

Arg Ala Glu Pro His Arg Val Thr Met Asp Val Tyr His Lys Arg Ile
                85                  90                  95

Arg Pro Phe Arg Leu Pro Leu Val Gln Lys Glu Trp Arg Thr Cys Glu
            100                 105                 110

Glu Asn Val Phe Gly Leu Tyr His Val Phe Glu Thr His Thr Tyr Ala Gly
            115                 120                 125
```

```
Tyr Phe Ser Asp Leu Leu Ile His Asp Val Glu Thr Asn Pro Gly
        130                 135                 140
```

<210> SEQ ID NO 47
<211> LENGTH: 143
<212> TYPE: PRT
<213> ORGANISM: Encephalomyocarditis virus

<400> SEQUENCE: 47

```
Ser Pro Asn Ala Leu Asp Ile Ser Arg Thr Tyr Pro Thr Leu His Val
1               5                   10                  15

Leu Ile Gln Phe Asn His Arg Gly Leu Glu Val Arg Leu Phe Arg His
            20                  25                  30

Gly His Phe Trp Ala Glu Thr Arg Ala Asp Val Ile Leu Arg Ser Lys
        35                  40                  45

Thr Lys Gln Val Ser Phe Leu Ser Asn Gly Asn Tyr Pro Ser Met Asp
    50                  55                  60

Ser Arg Ala Pro Trp Asn Pro Trp Lys Asn Thr Tyr Gln Ala Val Leu
65                  70                  75                  80

Arg Ala Glu Pro Cys Arg Val Thr Met Asp Ile Tyr Tyr Lys Arg Val
                85                  90                  95

Arg Pro Phe Arg Leu Pro Leu Val Gln Lys Glu Trp Pro Val Arg Glu
            100                 105                 110

Glu Asn Val Phe Gly Leu Tyr Arg Ile Phe Asn Ala His Tyr Ala Gly
        115                 120                 125

Tyr Phe Ala Asp Leu Leu Ile His Asp Ile Glu Thr Asn Pro Gly
    130                 135                 140
```

<210> SEQ ID NO 48
<211> LENGTH: 143
<212> TYPE: PRT
<213> ORGANISM: Encephalomyocarditis virus

<400> SEQUENCE: 48

```
Ser Pro Asn Ala Leu Asp Ile Ser Arg Thr Tyr Pro Thr Leu His Ile
1               5                   10                  15

Leu Ile Gln Phe Asn His Gly Gly Leu Glu Ile Arg Leu Phe Arg His
            20                  25                  30

Gly Met Phe Trp Ala Glu Ala His Ala Asp Val Ile Leu Arg Ser Arg
        35                  40                  45

Thr Lys Gln Ile Ser Phe Leu Asn Asn Gly Ser Phe Pro Ser Met Asp
    50                  55                  60

Ala Arg Ala Pro Trp Asn Pro Trp Lys Asn Thr Tyr His Ala Val Leu
65                  70                  75                  80

Arg Ala Glu Pro Tyr Arg Val Thr Met Asp Val Tyr His Lys Arg Ile
                85                  90                  95

Arg Pro Phe Arg Leu Pro Leu Val Gln Lys Glu Trp Asn Val Arg Glu
            100                 105                 110

Glu Asn Val Phe Gly Leu Tyr Gly Ile Phe Asn Ala His Tyr Ala Gly
        115                 120                 125

Tyr Phe Ala Asp Leu Leu Ile His Asp Ile Glu Thr Asn Pro Gly
    130                 135                 140
```

<210> SEQ ID NO 49
<211> LENGTH: 143
<212> TYPE: PRT
<213> ORGANISM: Encephalomyocarditis virus

<400> SEQUENCE: 49

-continued

```
Ser Pro Asn Ala Leu Asp Ile Ser Gly Thr Tyr Pro Thr Leu His Ile
1               5                   10                  15

Leu Ile Gln Phe Asn His Gly Gly Leu Glu Ile Arg Leu Phe Arg His
            20                  25                  30

Gly Met Phe Trp Ala Glu Ala His Ala Asp Val Ile Leu Arg Ser Arg
            35                  40                  45

Thr Lys Gln Ile Ser Phe Leu Asn Asn Gly Ser Phe Pro Ser Met Asp
        50                  55                  60

Ala Arg Ala Pro Trp Asn Pro Trp Lys Asn Thr Tyr His Ala Val Leu
65                  70                  75                  80

Arg Ala Glu Pro Tyr Arg Val Thr Met Asp Val Tyr His Lys Arg Ile
                85                  90                  95

Arg Pro Phe Arg Leu Pro Leu Val Gln Lys Glu Trp Asn Val Arg Glu
                100                 105                 110

Glu Asn Val Phe Gly Leu Tyr Gly Ile Phe Asn Ala His Tyr Ala Gly
                115                 120                 125

Tyr Phe Ala Asp Leu Leu Ile His Asp Ile Glu Thr Asn Pro Gly
                130                 135                 140

<210> SEQ ID NO 50
<211> LENGTH: 143
<212> TYPE: PRT
<213> ORGANISM: Encephalomyocarditis virus

<400> SEQUENCE: 50

Ser Pro Asn Ala Leu Asp Ile Ser Arg Thr Tyr Pro Thr Leu His Ile
1               5                   10                  15

Leu Ile Gln Phe Asn His Gly Gly Leu Glu Ile Arg Leu Phe Arg His
            20                  25                  30

Gly Gln Phe Trp Ala Glu Ala His Ala Asp Val Ile Leu Arg Ser Arg
            35                  40                  45

Thr Lys Gln Ile Ser Phe Leu Asn Asn Gly Ser Phe Pro Ser Met Asp
        50                  55                  60

Ala Arg Ala Pro Trp Asn Pro Trp Lys Asn Thr Tyr His Ala Val Leu
65                  70                  75                  80

Arg Ala Glu Pro Tyr Arg Val Thr Met Asp Val Tyr His Lys Arg Ile
                85                  90                  95

Arg Pro Phe Arg Leu Pro Leu Val Gln Lys Glu Trp Asn Val Arg Glu
                100                 105                 110

Glu Asn Val Phe Gly Leu Tyr Ser Ile Phe Asn Ala His Tyr Ala Gly
                115                 120                 125

Tyr Phe Ala Asp Leu Leu Ile His Asp Ile Glu Thr Asn Pro Gly
                130                 135                 140
```